US012479921B2

(12) United States Patent
Li et al.

(10) Patent No.: US 12,479,921 B2
(45) **Date of Patent: *Nov. 25, 2025**

(54) ANTI-PD-L1 ANTIBODY AND USE THEREOF

(71) Applicant: Oricell Therapeutics Co., Ltd., Shanghai (CN)

(72) Inventors: Bohua Li, Shanghai (CN); Huajing Wang, Shanghai (CN); Xiaowen He, Shanghai (CN)

(73) Assignee: Oricell Therapeutics Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/637,522

(22) Filed: Apr. 17, 2024

(65) Prior Publication Data

US 2024/0317863 A1 Sep. 26, 2024

Related U.S. Application Data

(63) Continuation of application No. 17/046,265, filed as application No. PCT/CN2018/102584 on Aug. 27, 2018, now Pat. No. 11,993,655.

(30) Foreign Application Priority Data

Apr. 9, 2018 (CN) ........................ 201810309302.5

(51) Int. Cl.

| | |
|---|---|
| ***C07K 16/28*** | (2006.01) |
| ***A61K 31/713*** | (2006.01) |
| ***A61P 35/00*** | (2006.01) |
| ***C12N 5/10*** | (2006.01) |
| ***C12N 15/63*** | (2006.01) |
| *A61K 39/00* | (2006.01) |

(52) U.S. Cl.

CPC ........ *C07K 16/2827* (2013.01); *A61K 31/713* (2013.01); *A61P 35/00* (2018.01); *C07K 16/2878* (2013.01); *C07K 16/2896* (2013.01); *C12N 5/10* (2013.01); *C12N 15/63* (2013.01); *A61K 2039/505* (2013.01); *C07K 2317/21* (2013.01); *C07K 2317/31* (2013.01); *C07K 2317/33* (2013.01); *C07K 2317/565* (2013.01); *C07K 2317/622* (2013.01); *C07K 2317/73* (2013.01); *C07K 2317/76* (2013.01)

(58) Field of Classification Search

None

See application file for complete search history.

(56) References Cited

U.S. PATENT DOCUMENTS

| | | | | |
|---|---|---|---|---|
| 9,789,183 | B1 | 10/2017 | Wang et al. | |
| 10,059,769 | B2 | 8/2018 | Fang et al. | |
| 2016/0244528 | A1 * | 8/2016 | Gray | A61P 13/12 |
| 2017/0319690 | A1 | 11/2017 | Wang et al. | |
| 2017/0355756 | A1 | 12/2017 | Julien | |
| 2018/0002423 | A1 | 1/2018 | Wang et al. | |
| 2018/0169232 | A1 | 6/2018 | Andrews | |

FOREIGN PATENT DOCUMENTS

| | | | |
|---|---|---|---|
| CN | 105669862 | A | 6/2016 |
| CN | 107428832 | A | 12/2017 |
| CN | 107488229 | A | 12/2017 |
| JP | 2018-508475 | A | 3/2018 |
| WO | WO 2007/005874 | A2 | 1/2007 |
| WO | 2008-068048 | | 6/2008 |
| WO | WO 2012/032433 | | 3/2012 |
| WO | WO 2014/055897 | A2 | 4/2014 |
| WO | WO 2015/119923 | A1 | 8/2015 |
| WO | WO 2017/132562 | A1 | 8/2017 |
| WO | WO 2017/215590 | A1 | 12/2017 |
| WO | WO 2018/056821 | A1 | 3/2018 |

OTHER PUBLICATIONS

Claus C, Ferrara-Koller C, Klein C. The emerging landscape of novel 4-1BB (CD137) agonistic drugs for cancer immunotherapy. MAbs. Jan.-Dec. 2023;15(1):2167189. (Year: 2023).*
Melero I, Sanmamed MF, Glez-Vaz J, Luri-Rey C, Wang J, Chen L. CD137 (4-1BB)-Based Cancer Immunotherapy on Its 25th Anniversary. Cancer Discov. Mar. 1, 2023;13(3):552-569. (Year: 2023).*
International Search Report issued on Jan. 14, 2019 in PCT/CN2018/102584 filed on Aug. 27, 2018, 5 pages.
Extended European Search Report issued Jan. 3, 2022, in corresponding European Patent Application No. 18914556.8, 6 pages.
Tan et al., "Distinct PD-L1 binding characteristics of therapeutic monoclonal antibody durvalumab", Protein Cell, Vo. 9, No. 1, 2018, pp. 135-139.
Almagro JC, Fransson J. Humanization of antibodies. Front Biosci. Jan. 1, 2008 ;13:1619-33. (Year: 2008).
Chen et al., Enhancement and destruction of antibody function by somatic mutation: unequal occurrence is controlled by V gene combinatorial associations. EMBO J. Jun. 15, 1995;14(12):2784-94. (Year: 1995).
Koenig et al. Mutational landscape of antibody variable domains reveals a switch modulating the interdomain conformational dynamics and antigen binding. PNAS Jan. 24, 2017 114(4)E486-E495;f irstpublished Jan. 5, 2017. (Year: 2017).

(Continued)

*Primary Examiner* — Aurora M Fontainhas
*Assistant Examiner* — Jennifer A Benavides
(74) *Attorney, Agent, or Firm* — Merchant & Gould P.C.; Daniel J. Pereira

(57) ABSTRACT

An antibody that binds to the PD-L1 protein or CD137 protein, an antigen-binding fragment or a variant thereof, as well as a bispecific antibody that can bind to both the PD-L1 protein and the CD137 protein. The bispecific antibody has a strong ability to specifically recognize the PD-L1 protein and the CD137 protein, and can enhance T-cell activity. The antibody or the antigen-binding fragment or the variant thereof and the bispecific antibody may be used in the prevention and treatment of tumors.

12 Claims, 15 Drawing Sheets

Specification includes a Sequence Listing.

(56) References Cited

OTHER PUBLICATIONS

Kussie et al. A single engineered amino acid substitution changes antibody fine specificity.J Immunol .Jan. 1, 1994 ;152(1 ): 146-52. ( Year: 1994).

Edwards et al. The remarkable flexibility of the human antibody repertoire;isolation of over one thousand different antibodies to a single protein,BLyS. J Mol Biol Nov. 14, 2003;334(1):103-18. (Year: 2003).

Eurasian Search Report issued Mar. 27, 2024, in corresponding Eurasian Application No. 202391538.

Ling Yi, et al. “Human and Mouse CD137 Have Predominantly Different Binding CRDs to Their Respective Ligands,”, *PLOS ONE*, vol. 9, Issue 1, Jan. 2014 (pp. 1-10).

Cariad Chester, et al., “Immunotherapy Targeting 4-1BB: Mechanistic Rationale, Clinical Results, and Future Strategies,” *Blood*, Jan. 4, 2018, vol. 131, No. 1 (p. 49-57).

Elisabeth Perez-Ruiz, et al., “Anti-CD137 and PD-1/PD-L1 Antibodies En Route Toward Clinical Synergy”, *Clin. Cancer Res.*, 23(18), Sep. 15, 2017, pp. 5326-5328.

* cited by examiner

Heavy chain variable region (CDR is underlined)

| | |
|---|---|
| Germline IGHV 1-69 | QVQLVQSGAEVKKPGSSVKVSCKASGGTFSSYAISWVRQAPGQGLEWMGRIIPILGIANYA<br>QKFQGRVTITADKSTSTAYMELSSLRSEDTAVYYCAR---GYSYGNFDYWGQGTLVTVSS |
| YN-002VH | QVQLVQSGAEVRKPGSSVKVSCKASGGTFSSYAISWVRQAPGQGLEWMGRIIPILGIANYA<br>QKFQGRVTITADKSTSTAYMELSSLRSEDTAVYYCARTMDGYSYGNFDYWGQGTLVTVSS |
| YN-003VH | QVQLVQSGAEVKKPGSSVKVSCKASGGTFSSYAISWVRQAPGQGLEWMGRIIPILGIANYA<br>QKFQGRVTITADKSTSTAYMELSSLRSEDTAVYYCARTMDGYSYGNFDYWGQGTLVTVSS |

Light chain variable region (CDR is underlined)

| | |
|---|---|
| Germline IGLV2-14 | QSALTQPASVSGSPGQSITISCTGTSSDVGGYNYVSWYQQHPGKAPKLMIYEVSNRPSGV<br>SNRFSGSKSGNTASLTISGLQAEDEADYYCSSYTSS----VFGGGTKLTVLG |
| YN-002VL | QSALTQPASVSGSPGQSITISCTGTSSDVGGYNYVSWYQQHPGKAPKLLIYGNSNRPSGV<br>PDRFSGSKSGTSASLAITGLQAEDEADYYCQSYDSSLSGSVFGGGTKLTVLG |
| YN-003VL | QSALTQPASVSGSPGQSITISCTGTSSDVGGYNYVSWYQQHPGKAPKLMIYGNSNRPSGV<br>SNRFSGSKSGNTASLTISGLQAEDEADYYCQSYDSSLSGSVFGGGTKLTVLG |

Fig. 1

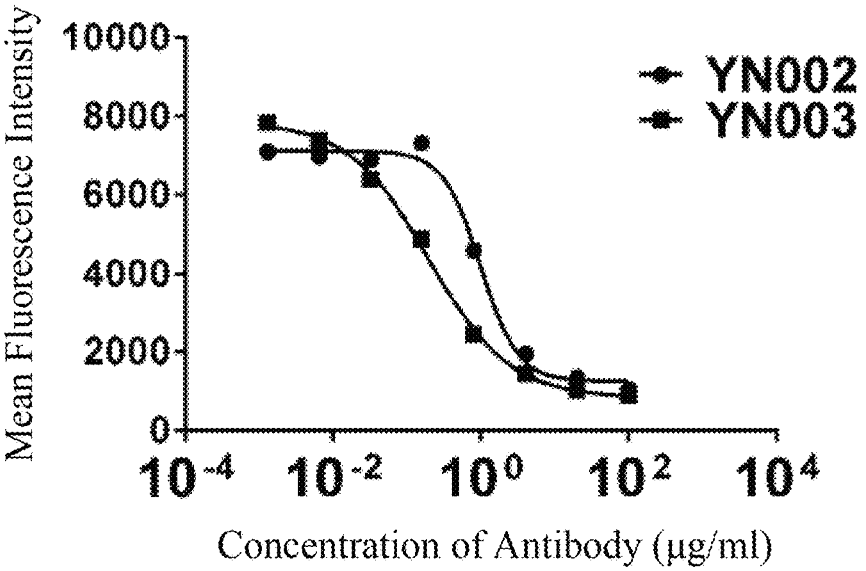

Fig. 2

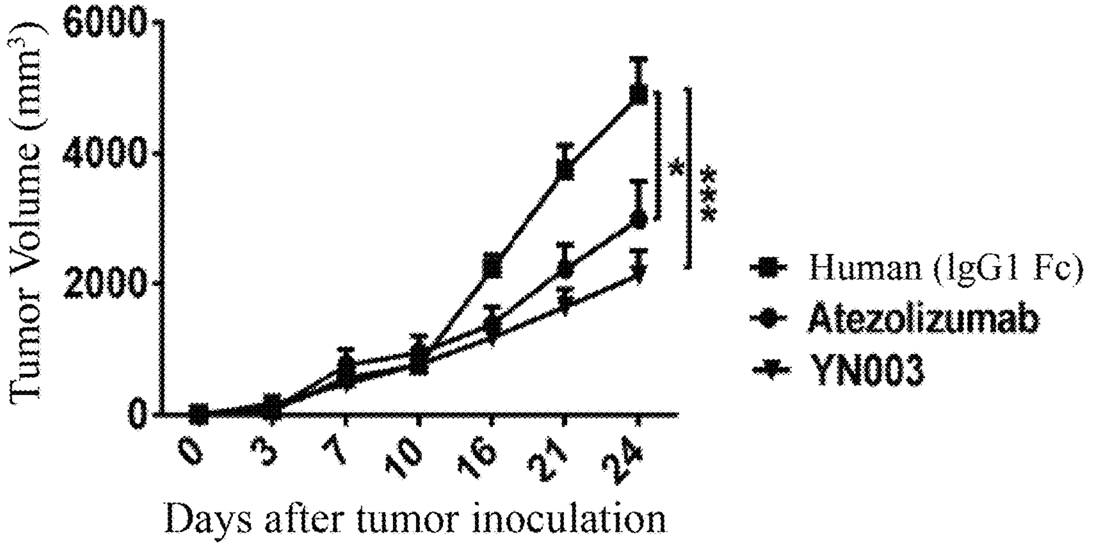

Fig. 5

Heavy chain variable region (CDR is underlined)

| | |
|---|---|
| Germline IGHV 3-23 | QVQLVESGGGLVQPGGSLRLSCAASGFTFSSYAMSWVRQAPGKGLEWVSAISGSGGSTYYAD<br>SVKGRFTISRDNSKNTLYLQMNSLRAEDTAVYYCAKTNWG--DAFDIWGQGTMVTVSS |
| YN-005VH | QVQLV**Q**SGGGLVQPGGSLRLSCAASGFTFSSYAMSWVRQAPGKGLEWVSAISGSGGSTYYAD<br>SVKGRFTISRDNSKNTLYLQMNSLRAEDTAVYYCAKTNWG**PS**DAFDIWGQGTMVTVSS |
| YN-006VH | QVQLVESGGGLVQPGGSLRLSCAASGFTFSSYAMSWVRQAPGKGLEWVSAISGSGGSTYYAD<br>SVKGRFTISRDNSKNTLYLQMNSLRAEDTAVYYCAKTNWG**PS**DAFDIWGQGTMVTVSS |

Light chain variable region (CDR is underlined)

| | |
|---|---|
| Germline IGLV1-44 | QSVLTQPPSASGTPGQRVTISCSGSSSNIGSNTVNWYQQLPGTAPKLLIYSNNQRPSGVPDR<br>FSGSKSGTSASLAISGLQSEDEADYYCAAWDDSLNGYVFGTGTKLTVLG |
| YN-005VL | QSVLTQPPSASGTPGQRVTISCSGS**TSD**IGS**YS**VNWYQQLPGTAPKLLIYSNNQRPSGVPDR<br>FSGSKSGTSASLAISGLQSEDEADYYCAAWDDSLNGYVFGTGTKLTVLG |
| YN-006VL | QSVLTQPPSASGTPGQRVTISCSGS**TSD**IGS**YS**VNWYQQLPGTAPKLLIYSNNQRPSGVPDR<br>FSGSKSGTSASLAISGLQSEDEADYYCAAWDDSLNGYVFGTGTKLTVLG |

Fig. 6

Fig. 8

Heavy chain variable region (CDR is underlined)

| | |
|---|---|
| Germline IGHV1-69 | QVQLVQSGAEVKKPGSSVKVSCKASGGTFSSYAISWVRQAPGQGLEWMGRIIPILGIANYAQKFQGRVTITADKSTSTAYMELSSLRSEDTAVYYCAR---YYSYGMDYWGQGTLVTVSS |
| YN003VH | QVQLVQSGAEVKKPGSSVKVSCKASGGTFSSYAISWVRQAPGQGLEWMGRIIPILGIANYAQKFQGRVTITADKSTSTAYMELSSLRSEDTAVYYCARTNDYYSYGMDYWGQGTLVTVSS |

Light chain variable region (CDR is underlined)

| | |
|---|---|
| Germline IGLV2-14 | QSALTQPASVSGSPGQSITISCTGTSSDVGGYNYVSWYQQHPGKAPKLMIYEVSNRPSGVSNRFSGSKSGNTASLTISGLQAEDEADYYCSSYTSS----VFGGGTKLTVLG |
| YN003VL | QSALTQPASVSGSPGQSITISCTGTSSDVGGYNYVSWYQQHPGKAPKLMIYGNSNRPSGVSNRFSGSKSGNTASLTISGLQAEDEADYYCQSYDSSLSGSVFGGGTKLTVLG |

Heavy chain variable region (CDR is underlined)

SEQUENCE LISTING

```
Sequence total quantity: 96
SEQ ID NO: 1            moltype = DNA  length = 363
FEATURE                 Location/Qualifiers
misc_feature            1..363
                        note = Nucleotide sequence encoding PD-L1 antibody YN-002 VH
source                  1..363
                        mol_type = other DNA
                        organism = synthetic construct
SEQUENCE: 1
caggtgcagc tggtgcagtc tggggctgag gtgaggaagc ctgggtcctc ggtgaaggtc  60
tcctgcaagg cttctggagg caccttcagc agctatgcta tcagctgggt gcgacaggcc  120
cctggacaag ggcttgagtg gatgggaagg atcatcccta tccttggtat agcaaactac  180
gcacagaagt tccagggcag agtcacgatt accgcggaca aatccacgag cacagcctac  240
atggagctga gcagcctgag atctgaggac acggccgtgt attactgtgc gagaacgatg  300
gacggataca gctatggcaa ctttgactac tggggccagg gaaccctggt cactgtctcc  360
tca                                                               363

SEQ ID NO: 2            moltype = AA  length = 121
FEATURE                 Location/Qualifiers
REGION                  1..121
                        note = VH of PD-L1 antibody YN-002
source                  1..121
                        mol_type = protein
                        organism = synthetic construct
SEQUENCE: 2
QVQLVQSGAE VRKPGSSVKV SCKASGGTFS SYAISWVRQA PGQGLEWMGR IIPILGIANY  60
AQKFQGRVTI TADKSTSTAY MELSSLRSED TAVYYCARTM DGYSYGNFDY WGQGTLVTVS  120
S                                                                 121

SEQ ID NO: 3            moltype = DNA  length = 336
FEATURE                 Location/Qualifiers
misc_feature            1..336
                        note = Nucleotide sequence encoding PD-L1 antibody YN-002 VL
source                  1..336
                        mol_type = other DNA
                        organism = synthetic construct
SEQUENCE: 3
cagtctgccc tgactcagcc tgcctccgtg tctgggtctc ctggacagtc gatcaccatc  60
tcctgcaccg gaaccagcag tgacgttggt ggttataact atgtctcctg gtaccaacag  120
cacccaggca aagcccccaa actcctcatc tatggtaaca gcaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtggttcg  300
gtattcggcg gagggaccaa gctgaccgtc ctaggc                           336

SEQ ID NO: 4            moltype = AA  length = 112
FEATURE                 Location/Qualifiers
REGION                  1..112
                        note = VL of PD-L1 antibody YN-002
source                  1..112
                        mol_type = protein
                        organism = synthetic construct
SEQUENCE: 4
QSALTQPASV SGSPGQSITI SCTGTSSDVG GYNYVSWYQQ HPGKAPKLLI YGNSNRPSGV  60
PDRFSGSKSG TSASLAITGL QAEDEADYYC QSYDSSLSGS VFGGGTKLTV LG          112
```

```
SEQ ID NO: 5            moltype = DNA  length = 1353
FEATURE                 Location/Qualifiers
misc_feature            1..1353
                        note = Nucleotide sequence encoding the heavy chain of
                         PD-L1 antibodyYN-002
source                  1..1353
                        mol_type = other DNA
                        organism = synthetic construct
SEQUENCE: 5
caggtgcagc tggtgcagtc tggggctgag gtgaggaagc ctgggtcctc ggtgaaggtc  60
tcctgcaagg cttctggagg caccttcagc agctatgcta tcagctgggt gcgacaggcc  120
cctggacaag ggcttgagtg gatgggaagg atcatcccta tccttggtat agcaaactac  180
gcacagaagt tccagggcag agtcacgatt accgcggaca aatccacgag cacagcctac  240
atggagctga gcagcctgag atctgaggac acggccgtgt attactgtgc gagaacgatg  300
gacggataca gctatggcaa ctttgactac tggggccagg gaaccctggt cactgtctcc  360
tcagcgtcga ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggat  1080
gagctgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                              1353

SEQ ID NO: 6            moltype = AA  length = 451
FEATURE                 Location/Qualifiers
REGION                  1..451
                        note = Heavy chain of PD-L1 antibody YN-002
source                  1..451
                        mol_type = protein
                        organism = synthetic construct
SEQUENCE: 6
QVQLVQSGAE VRKPGSSVKV SCKASGGTFS SYAISWVRQA PGQGLEWMGR IIPILGIANY  60
AQKFQGRVTI TADKSTSTAY MELSSLRSED TAVYYCARTM DGYSYGNFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 7            moltype = DNA  length = 651
FEATURE                 Location/Qualifiers
misc_feature            1..651
                        note = Nucleotide sequence encoding the light chain of
                         PD-L1 antibodyYN-002
source                  1..651
                        mol_type = other DNA
                        organism = synthetic construct
SEQUENCE: 7
cagtctgccc tgactcagcc tgcctccgtg tctgggtctc ctggacagtc gatcaccatc  60
tcctgcaccg gaaccagcag tgacgttggt ggttataact atgtctcctg gtaccaacag  120
cacccaggca aagcccccaa actcctcatc tatggtaaca gcaatcggcc ctcaggggtc  180
cctgaccgat tctctggctc caagtctggc acctcagcct ccctggccat cactgggctc  240
caggctgagg atgaggctga ttattactgc cagtcctatg acagcagcct gagtggttcg  300
gtattcggcg gagggaccaa gctgaccgtc ctaggccagc ccaaggctgc cccctcggtc  360
actctgttcc caccctcctc tgaggagctt caagccaaca aggccacact ggtgtgtctc  420
ataagtgact tctacccggg agccgtgaca gtggcctgga aggcagatag cagccccgtc  480
aaggcgggag tggagaccac cacaccctcc aaacaaagca acaacaagta cgcggccagc  540
agctacctga gcctgacgcc tgagcagtgg aagtcccaca gaagctacag ctgccaggtc  600
acgcatgaag ggagcaccgt ggagaagaca gtggccccta cagaatgttc a           651

SEQ ID NO: 8            moltype = AA  length = 217
FEATURE                 Location/Qualifiers
REGION                  1..217
                        note = Light chain of PD-L1 antibody YN-002
source                  1..217
                        mol_type = protein
                        organism = synthetic construct
```

```
SEQUENCE: 8
QSALTQPASV SGSPGQSITI SCTGTSSDVG GYNYVSWYQQ HPGKAPKLLI YGNSNRPSGV  60
PDRFSGSKSG TSASLAITGL QAEDEADYYC QSYDSSLSGS VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 9            moltype = AA  length = 121
FEATURE                 Location/Qualifiers
REGION                  1..121
                        note = VH of PD-L1 antibody YN-003
source                  1..121
                        mol_type = protein
                        organism = synthetic construct
SEQUENCE: 9
QVQLVQSGAE VKKPGSSVKV SCKASGGTFS SYAISWVRQA PGQGLEWMGR IIPILGIANY  60
AQKFQGRVTI TADKSTSTAY MELSSLRSED TAVYYCARTM DGYSYGNFDY WGQGTLVTVS  120
S                                                                  121

SEQ ID NO: 10           moltype = DNA  length = 363
FEATURE                 Location/Qualifiers
misc_feature            1..363
                        note = Nucleotide sequence encoding PD-L1 antibody YN-003 VH
source                  1..363
                        mol_type = other DNA
                        organism = synthetic construct
SEQUENCE: 10
caggtgcagc tggtgcagtc tggggctgag gtgaagaagc ctgggtcctc ggtgaaggtc  60
tcctgcaagg cttctggagg caccttcagc agctatgcta tcagctgggt gcgacaggcc  120
cctggacaag ggcttgagtg gatgggaagg atcatcccta tccttggtat agcaaactac  180
gcacagaagt tccagggcag agtcacgatt accgcggaca aatccacgag cacagcctac  240
atggagctga gcagcctgag atctgaggac acggccgtgt attactgtgc gagaacgatg  300
gacggataca gctatggcaa ctttgactac tggggccagg gaaccctggt cactgtctcc  360
tca                                                                363

SEQ ID NO: 11           moltype = AA  length = 112
FEATURE                 Location/Qualifiers
REGION                  1..112
                        note = VL of PD-L1 antibody YN-003
source                  1..112
                        mol_type = protein
                        organism = synthetic construct
SEQUENCE: 11
QSALTQPASV SGSPGQSITI SCTGTSSDVG GYNYVSWYQQ HPGKAPKLMI YGNSNRPSGV  60
SNRFSGSKSG NTASLTISGL QAEDEADYYC QSYDSSLSGS VFGGGTKLTV LG          112

SEQ ID NO: 12           moltype = DNA  length = 336
FEATURE                 Location/Qualifiers
misc_feature            1..336
                        note = Nucleotide sequence encoding PD-L1 antibody YN-003 VL
source                  1..336
                        mol_type = other DNA
                        organism = synthetic construct
SEQUENCE: 12
cagtctgccc tgactcagcc tgcctccgtg tctgggtctc ctggacagtc gatcaccatc  60
tcctgcaccg gaaccagcag tgacgttggt ggttataact atgtctcctg gtaccaacag  120
cacccaggca aagcccccaa actcatgatc tatggtaaca gcaatcggcc ctcaggggtc  180
tctaatcgat tctctggctc caagtctggc aacacggcct ccctgaccat ctctgggctc  240
caggctgagg atgaggctga ttattactgc cagtcctatg acagcagcct gagtggttcg  300
gtattcggcg gagggaccaa gctgaccgtc ctaggc                           336

SEQ ID NO: 13           moltype = AA  length = 451
FEATURE                 Location/Qualifiers
REGION                  1..451
                        note = Heavy chain of PD-L1 antibody YN-003
source                  1..451
                        mol_type = protein
                        organism = synthetic construct
SEQUENCE: 13
QVQLVQSGAE VKKPGSSVKV SCKASGGTFS SYAISWVRQA PGQGLEWMGR IIPILGIANY  60
AQKFQGRVTI TADKSTSTAY MELSSLRSED TAVYYCARTM DGYSYGNFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 14           moltype = DNA  length = 1353
FEATURE                 Location/Qualifiers
```

```
misc_feature          1..1353
                      note = Nucleotide sequence encoding the heavy chain of
                       PD-L1 antibodyYN-003
source                1..1353
                      mol_type = other DNA
                      organism = synthetic construct
SEQUENCE: 14
caggtgcagc tggtgcagtc tggggctgag gtgaagaagc ctgggtcctc ggtgaaggtc  60
tcctgcaagg cttctggagg caccttcagc agctatgcta tcagctgggt gcgacaggcc  120
cctggacaag ggcttgagtg gatgggaagg atcatcccta tccttggtat agcaaactac  180
gcacagaagt tccagggcag agtcacgatt accgcggaca aatccacgag cacagcctac  240
atggagctga gcagcctgag atctgaggac acggccgtgt attactgtgc gagaacgatg  300
gacggataca gctatggcaa ctttgactac tggggccagg gaaccctggt cactgtctcc  360
tcagcgtcga ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggat  1080
gagctgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                              1353

SEQ ID NO: 15         moltype = AA  length = 217
FEATURE               Location/Qualifiers
REGION                1..217
                      note = Light chain of PD-L1 antibody YN-003; The second
                       polypeptide ofPD-L1/4-1BB bispecific antibody YN-007
source                1..217
                      mol_type = protein
                      organism = synthetic construct
SEQUENCE: 15
QSALTQPASV SGSPGQSITI SCTGTSSDVG GYNYVSWYQQ HPGKAPKLMI YGNSNRPSGV  60
SNRFSGSKSG NTASLTISGL QAEDEADYYC QSYDSSLSGS VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 16         moltype = DNA  length = 651
FEATURE               Location/Qualifiers
misc_feature          1..651
                      note = Nucleotide sequence encoding the light chain of
                       PD-L1 antibodyYN-003; Nucleotide sequence encoding the
                       second polypeptide ofYN-007
source                1..651
                      mol_type = other DNA
                      organism = synthetic construct
SEQUENCE: 16
cagtctgccc tgactcagcc tgcctccgtg tctgggtctc ctggacagtc gatcaccatc  60
tcctgcaccg gaaccagcag tgacgttggt ggttataact atgtctcctg gtaccaacag  120
cacccaggca aagcccccaa actcatgatc tatggtaaca gcaatcggcc ctcaggggtc  180
tctaatcgat tctctggctc caagtctggc aacacggcct ccctgaccat ctctgggctc  240
caggctgagg atgaggctga ttattactgc cagtcctatg acagcagcct gagtggttcg  300
gtattcggcg gagggaccaa gctgaccgtc ctaggccagc ccaaggctgc cccctcggtc  360
actctgttcc caccctcctc tgaggagctt caagccaaca aggccacact ggtgtgtctc  420
ataagtgact tctacccggg agccgtgaca gtggcctgga aggcagatag cagccccgtc  480
aaggcgggag tggagaccac cacaccctcc aaacaaagca acaacaagta cgcggccagc  540
agctacctga gcctgacgcc tgagcagtgg aagtcccaca gaagctacag ctgccaggtc  600
acgcatgaag ggagcaccgt ggagaagaca gtggccccta cagaatgttc a          651

SEQ ID NO: 17         moltype = DNA  length = 360
FEATURE               Location/Qualifiers
misc_feature          1..360
                      note = Nucleotide sequence encoding 4-1BB antibody YN-005 VH
source                1..360
                      mol_type = other DNA
                      organism = synthetic construct
SEQUENCE: 17
caggtccagc tggtgcagtc tgggggaggc ttggtacagc ctgggggtc cctgagactc  60
tcctgtgcag cctctggatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
```

```
cttcaaatga acagcctgag agccgaggac acggccgtgt attactgtgc gaaaactaac  300
tggggcccct ctgatgcttt tgatatctgg ggccaaggga caatggtcac cgtctcctca  360

SEQ ID NO: 18          moltype = AA  length = 120
FEATURE                Location/Qualifiers
REGION                 1..120
                       note = VH of 4-1BB antibody YN-005
source                 1..120
                       mol_type = protein
                       organism = synthetic construct
SEQUENCE: 18
QVQLVQSGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKTN WGPSDAFDIW GQGTMVTVSS  120

SEQ ID NO: 19          moltype = DNA  length = 333
FEATURE                Location/Qualifiers
misc_feature           1..333
                       note = Nucleotide sequence encoding 4-1BB antibody YN-005
                        VL; Nucleotidesequence encoding YN-006 VL
source                 1..333
                       mol_type = other DNA
                       organism = synthetic construct
SEQUENCE: 19
cagagcgtct tgactcagcc accctcagcg tctgggaccc ccgggcagag ggtcaccatc  60
tcttgttctg gaagcacctc cgacatcgga agttacagcg taaactggta ccagcagctc  120
ccaggaacgg cccccaaact cctcatctat agtaataatc agcggccctc aggggtccct  180
gaccgattct ctggctccaa gtctggcacc tcagcctccc tggccatcag tgggctccag  240
tctgaggatg aggctgatta ttactgtgca gcatgggatg acagcctgaa tggttatgtc  300
ttcggaactg ggaccaagct gaccgtccta ggt                              333

SEQ ID NO: 20          moltype = AA  length = 111
FEATURE                Location/Qualifiers
REGION                 1..111
                       note = VL of human 4-1BB antibody YN-006; VL of YN-005
source                 1..111
                       mol_type = protein
                       organism = synthetic construct
SEQUENCE: 20
QSVLTQPPSA SGTPGQRVTI SCSGSTSDIG SYSVNWYQQL PGTAPKLLIY SNNQRPSGVP  60
DRFSGSKSGT SASLAISGLQ SEDEADYYCA AWDDSLNGYV FGTGTKLTVL G           111

SEQ ID NO: 21          moltype = AA  length = 446
FEATURE                Location/Qualifiers
REGION                 1..446
                       note = Heavy chain of 4-1BB antibody YN-005
source                 1..446
                       mol_type = protein
                       organism = synthetic construct
SEQUENCE: 21
QVQLVQSGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKTN WGPSDAFDIW GQGTMVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                      446

SEQ ID NO: 22          moltype = DNA  length = 1338
FEATURE                Location/Qualifiers
misc_feature           1..1338
                       note = Nucleotide sequence encoding the heavy chain of
                        4-1BB antibodyYN-005
source                 1..1338
                       mol_type = other DNA
                       organism = synthetic construct
SEQUENCE: 22
caggtccagc tggtgcagtc tgggggaggc ttggtacagc ctggggggtc cctgagactc  60
tcctgtgcag cctctggatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
cttcaaatga acagcctgag agccgaggac acggccgtgt attactgtgc gaaaactaac  300
tggggcccct ctgatgcttt tgatatctgg ggccaaggga caatggtcac cgtctcctca  360
gcgtcgacca agggcccatc ggtcttcccc ctggcgccct gctccaggag cacctccgag  420
agcacagcgg ccctgggctg cctggtcaag gactacttcc ccgaaccagt gacggtgtcg  480
tggaactcag gcgctctgac cagcggcgtg cacaccttcc cggctgtcct acagtcctca  540
ggactctact ccctcagcag cgtagtgacc gtgccctcca gcaacttcgg cacccagacc  600
tacacctgca acgtagatca caagcccagc aacaccaagg tggacaagac agttgagcgc  660
aaatgttgtg tcgagtgccc accgtgccca gcaccacctg tggcaggacc gtcagtcttc  720
```

```
ctcttccccc caaaacccaa ggacaccctc atgatctccc ggacccctga ggtcacgtgc  780
gtggtggtgg acgtgagcca cgaagacccc gaggtccagt tcaactggta cgtggacggc  840
gtggaggtgc ataatgccaa gacaaagcca cgggaggagc agttcaacag cacgttccgt  900
gtggtcagcg tcctcaccgt cgtgcaccag gactggctga acggcaagga gtacaagtgc  960
aaggtctcca acaaaggcct cccagccccc atcgagaaaa ccatctccaa aaccaaaggg  1020
cagccccgag aaccacaggt gtacaccctg cccccatccc gggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacac ctcccatgct ggactccgac  1200
ggctccttct tcctctacag caagctcacc gtggacaaga gcaggtggca gcaggggaac  1260
gtcttctcat gctccgtgat gcatgaggct ctgcacaacc actacacaca gaagagcctc  1320
tccctgtctc cgggtaaa                                              1338

SEQ ID NO: 23          moltype = AA  length = 216
FEATURE                Location/Qualifiers
REGION                 1..216
                       note = Light chain of 4-1BB antibody YN-005; YN-006 light
                        chain
source                 1..216
                       mol_type = protein
                       organism = synthetic construct
SEQUENCE: 23
QSVLTQPPSA SGTPGQRVTI SCSGSTSDIG SYSVNWYQQL PGTAPKLLIY SNNQRPSGVP  60
DRFSGSKSGT SASLAISGLQ SEDEADYYCA AWDDSLNGYV FGTGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                          216

SEQ ID NO: 24          moltype = DNA  length = 648
FEATURE                Location/Qualifiers
misc_feature           1..648
                       note = The nucleotide sequence of the light chain of 4-1BB
                        antibodyYN-005; Nucleotide sequence encoding YN-006 light
                        chain
source                 1..648
                       mol_type = other DNA
                       organism = synthetic construct
SEQUENCE: 24
cagagcgtct tgactcagcc accctcagcg tctgggaccc ccgggcagag ggtcaccatc  60
tcttgttctg gaagcacctc cgacatcgga agttacagcg taaactggta ccagcagctc  120
ccaggaacgg cccccaaact cctcatctat agtaataatc agcggccctc aggggtccct  180
gaccgattct ctggctccaa gtctggcacc tcagcctccc tggccatcag tgggctccag  240
tctgaggatg aggctgatta ttactgtgca gcatgggatg acagcctgaa tggttatgtc  300
ttcggaactg ggaccaagct gaccgtccta ggtcagccca aggctgcccc ctcggtcact  360
ctgttcccac cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca acaagtacgc ggccagcagc  540
tacctgagcc tgacgcctga gcagtggaag tcccacagaa gctacagctg ccaggtcacg  600
catgaaggga gcaccgtgga gaagacagtg gcccctacag aatgttca              648

SEQ ID NO: 25          moltype = AA  length = 120
FEATURE                Location/Qualifiers
REGION                 1..120
                       note = VH of human 4-1BB antibody YN-006
source                 1..120
                       mol_type = protein
                       organism = synthetic construct
SEQUENCE: 25
QVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKTN WGPSDAFDIW GQGTMVTVSS  120

SEQ ID NO: 26          moltype = DNA  length = 360
FEATURE                Location/Qualifiers
misc_feature           1..360
                       note = Nucleotide sequence encoding 4-1BB antibody YN-006 VH
source                 1..360
                       mol_type = other DNA
                       organism = synthetic construct
SEQUENCE: 26
caggtccagc tggtggaatc tgggggaggc ttggtacagc ctggggggtc cctgagactc  60
tcctgtgcag cctctggatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
cttcaaatga acagcctgag agccgaggac acggccgtgt attactgtgc gaaaactaac  300
tggggcccct ctgatgcttt tgatatctgg ggccaaggga caatggtcac cgtctcctca  360

SEQ ID NO: 27          moltype = AA  length = 446
FEATURE                Location/Qualifiers
REGION                 1..446
                       note = Heavy chain of 4-1BB antibody YN-006
source                 1..446
```

```
                        mol_type = protein
                        organism = synthetic construct
SEQUENCE: 27
QVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKTN WGPSDAFDIW GQGTMVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                      446

SEQ ID NO: 28           moltype = DNA  length = 1338
FEATURE                 Location/Qualifiers
misc_feature            1..1338
                        note = Nucleotide sequence encoding heavy chain of 4-1BB
                         antibody YN-006
source                  1..1338
                        mol_type = other DNA
                        organism = synthetic construct
SEQUENCE: 28
caggtccagc tggtggaatc tggggaggc ttggtacagc ctggggggtc cctgagactc  60
tcctgtgcag cctctggatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
cttcaaatga acagcctgag agccgaggac acggccgtgt attactgtgc gaaaactaac  300
tggggcccct ctgatgcttt tgatatctgg ggccaaggga caatggtcac cgtctcctca  360
gcgtcgacca agggcccatc ggtcttcccc ctggcgccct gctccaggag cacctccgag  420
agcacagcgg ccctgggctg cctggtcaag gactacttcc ccgaaccagt gacggtgtcg  480
tggaactcag gcgctctgac cagcggcgtg cacaccttcc cggctgtcct acagtcctca  540
ggactctact ccctcagcag cgtagtgacc gtgccctcca gcaacttcgg cacccagacc  600
tacacctgca acgtagatca caagcccagc aacaccaagg tggacaagac agttgagcgc  660
aaatgttgtg tcgagtgccc accgtgccca gcaccacctg tggcaggacc gtcagtcttc  720
ctcttccccc caaaacccaa ggacaccctc atgatctccc ggacccctga ggtcacgtgc  780
gtggtggtgg acgtgagcca cgaagacccc gaggtccagt tcaactggta cgtggacggc  840
gtggaggtgc ataatgccaa gacaaagcca cgggaggagc agttcaacag cacgttccgt  900
gtggtcagcg tcctcaccgt cgtgcaccag gactggctga acggcaagga gtacaagtgc  960
aaggtctcca acaaaggcct cccagccccc atcgagaaaa ccatctccaa aaccaaaggg  1020
cagccccgag aaccacaggt gtacaccctg cccccatccc gggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacac ctcccatgct ggactccgac  1200
ggctccttct tcctctacag caagctcacc gtggacaaga gcaggtggca gcaggggaac  1260
gtcttctcat gctccgtgat gcatgaggct ctgcacaacc actacacaca gaagagcctc  1320
tccctgtctc cgggtaaa                                               1338

SEQ ID NO: 29           moltype = DNA  length = 2139
FEATURE                 Location/Qualifiers
misc_feature            1..2139
                        note = Nucleotide sequence encoding the first polypeptide
                         of PD-L1/CD137bispecific antibody YN-007
source                  1..2139
                        mol_type = other DNA
                        organism = synthetic construct
SEQUENCE: 29
caggtgcagc tggtgcagtc tggggctgag gtgaagaagc ctgggtcctc ggtgaaggtc  60
tcctgcaagg cttctggagg caccttcagc agctatgcta tcagctgggt gcgacaggcc  120
cctggacaag ggcttgagtg gatgggaagg atcatcccta tccttggtat agcaaactac  180
gcacagaagt tccagggcag agtcacgatt accgcggaca aatccacgag cacagcctac  240
atggagctga gcagcctgag atctgaggac acggccgtgt attactgtgc gagaacgatg  300
gacggataca gctatggcaa ctttgactac tggggccagg gaaccctggt cactgtctcc  360
tcagcgtcga ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca ccctcatgat ctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
gcaagcacgt accgtgtggt cagcgtcctc accgtcctgc accaggactg gctgaatggc  960
aaggagtaca agtgcaaggt ctccaacaaa gccctcccag cccccatcga gaaaaccatc  1020
tccaaagcca aagggcagcc ccgagaacca caggtgtaca ccctgccccc atcccgggaa  1080
gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt ggcggtggaa gcggcggtgg cggaagcggc  1380
ggtggcggca gccaggtcca gctggtggaa tctgggggag gcttggtaca gcctgggggg  1440
tccctgagac tctcctgtgc agcctctgga ttcaccttta gcagctatgc catgagctgg  1500
```

-continued

```
gtccgccagg ctccagggaa ggggctggag tgggtctcag ctattagtgg tagtggtggt  1560
agcacatact acgcagactc cgtgaagggc cggttcacca tctccagaga caattccaag  1620
aacacgctgt atcttcaaat gaacagcctg agagccgagg acacggccgt gtattactgt  1680
gcgaaaacta actggggccc ctctgatgct tttgatatct ggggccaagg gacaatggtc  1740
accgtctcct cagcctccac cggtggcggt ggaagcggcg gtggcggaag cggcggtggc  1800
ggcagccaga gcgtcttgac tcagccaccc tcagcgtctg ggacccccgg gcagagggtc  1860
accatctctt gttctggaag cacctccgac atcggaagtt acagcgtaaa ctggtaccag  1920
cagctcccag gaacggcccc caaactcctc atctatagta ataatcagcg gccctcaggg  1980
gtccctgacc gattctctgg ctccaagtct ggcacctcag cctccctggc catcagtggg  2040
ctccagtctg aggatgaggc tgattattac tgtgcagcat gggatgacag cctgaatggt  2100
tatgtcttcg gaactgggac caagctgacc gtcctaggt                         2139

SEQ ID NO: 30          moltype = AA  length = 713
FEATURE                Location/Qualifiers
REGION                 1..713
                       note = The first polypeptide of PD-L1/CD137 bispecific
                        antibody YN-007
source                 1..713
                       mol_type = protein
                       organism = synthetic construct
SEQUENCE: 30
QVQLVQSGAE VKKPGSSVKV SCKASGGTFS SYAISWVRQA PGQGLEWMGR IIPILGIANY  60
AQKFQGRVTI TADKSTSTAY MELSSLRSED TAVYYCARTM DGYSYGNFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
ASTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG GGGSGGGGSG GGGSQVQLVE SGGGLVQPGG  480
SLRLSCAASG FTFSSYAMSW VRQAPGKGLE WVSAISGSGG STYYADSVKG RFTISRDNSK  540
NTLYLQMNSL RAEDTAVYYC AKTNWGPSDA FDIWGQGTMV TVSSASTGGG GSGGGGSGGG  600
GSQSVLTQPP SASGTPGQRV TISCSGSTSD IGSYSVNWYQ QLPGTAPKLL IYSNNQRPSG  660
VPDRFSGSKS GTSASLAISG LQSEDEADYY CAAWDDSLNG YVFGTGTKLT VLG         713

SEQ ID NO: 31          moltype = AA  length = 121
FEATURE                Location/Qualifiers
REGION                 1..121
                       note = YN-035VH
source                 1..121
                       mol_type = protein
                       organism = synthetic construct
SEQUENCE: 31
QVQLVQSGAE VKKPGSSVKV SCKASRGPFS TYAISWVRQA PGQGLEWMGR IIPILGIANY  60
AQKFQGRVTI TADKSTSTAY MELSSLRSED TAVYYCARTM EGYGFGNFDY WGQGTLVTVS  120
S                                                                  121

SEQ ID NO: 32          moltype = AA  length = 451
FEATURE                Location/Qualifiers
REGION                 1..451
                       note = heavy chain of YN-035
source                 1..451
                       mol_type = protein
                       organism = synthetic construct
SEQUENCE: 32
QVQLVQSGAE VKKPGSSVKV SCKASRGPFS TYAISWVRQA PGQGLEWMGR IIPILGIANY  60
AQKFQGRVTI TADKSTSTAY MELSSLRSED TAVYYCARTM EGYGFGNFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 33          moltype = AA  length = 112
FEATURE                Location/Qualifiers
REGION                 1..112
                       note = YN-035VL/YN-036VL
source                 1..112
                       mol_type = protein
                       organism = synthetic construct
SEQUENCE: 33
QSALTQPASV SGSPGQSITI SCTGTVSEVG GYNEVSWYQQ HPGKAPKLMI YGNSNRPSGV  60
SNRFSGSKSG NTASLTISGL QAEDEADYYC QSYDSSLSGT VFGGGTKLTV LG          112

SEQ ID NO: 34          moltype = AA  length = 217
FEATURE                Location/Qualifiers
REGION                 1..217
                       note = light chain of YN-035; light chain of YN-036; second
                        polypeptideof YN-051; second polypeptide of YN-052
```

```
source                  1..217
                        mol_type = protein
                        organism = synthetic construct
SEQUENCE: 34
QSALTQPASV SGSPGQSITI SCTGTVSEVG GYNEVSWYQQ HPGKAPKLMI YGNSNRPSGV  60
SNRFSGSKSG NTASLTISGL QAEDEADYYC QSYDSSLSGT VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 35           moltype = AA  length = 121
FEATURE                 Location/Qualifiers
REGION                  1..121
                        note = YN-036VH/YN-037VH/YN-038VH/YN-039VH
source                  1..121
                        mol_type = protein
                        organism = synthetic construct
SEQUENCE: 35
QVQLVQSGAE VKKPGSSVKV SCKASRGPFS TYAISWVRQA PGQGLEWMGR IIPILGIANY  60
AQKFQGRVTI TADKSTSTAY MELSSLRSED TAVYYCARTM GEYSYGNYDY WGQGTLVTVS  120
S                                                                 121

SEQ ID NO: 36           moltype = AA  length = 451
FEATURE                 Location/Qualifiers
REGION                  1..451
                        note = YN-036/YN-037/YN-038/YN-039 heavy chain
source                  1..451
                        mol_type = protein
                        organism = synthetic construct
SEQUENCE: 36
QVQLVQSGAE VKKPGSSVKV SCKASRGPFS TYAISWVRQA PGQGLEWMGR IIPILGIANY  60
AQKFQGRVTI TADKSTSTAY MELSSLRSED TAVYYCARTM GEYSYGNYDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 37           moltype = AA  length = 112
FEATURE                 Location/Qualifiers
REGION                  1..112
                        note = YN-037VL
source                  1..112
                        mol_type = protein
                        organism = synthetic construct
SEQUENCE: 37
QSALTQPASV SGSPGQSITI SCTGTSSSVG GYREVSWYQQ HPGKAPKLMI YENSIRPSGV  60
SHRFSGSKSG NTASLTISGL QAEDEADYYC QSYDSSLSGT VFGGGTKLTV LG         112

SEQ ID NO: 38           moltype = AA  length = 217
FEATURE                 Location/Qualifiers
REGION                  1..217
                        note = YN-037 light chain
source                  1..217
                        mol_type = protein
                        organism = synthetic construct
SEQUENCE: 38
QSALTQPASV SGSPGQSITI SCTGTSSSVG GYREVSWYQQ HPGKAPKLMI YENSIRPSGV  60
SHRFSGSKSG NTASLTISGL QAEDEADYYC QSYDSSLSGT VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 39           moltype = AA  length = 112
FEATURE                 Location/Qualifiers
REGION                  1..112
                        note = YN-038VL
source                  1..112
                        mol_type = protein
                        organism = synthetic construct
SEQUENCE: 39
QSALTQPASV SGSPGQSITI SCTGTRSDVG GYNEVSWYQQ HPGKAPKLMI YENSIRPSGV  60
SHRFSGSKSG NTASLTISGL QAEDEADYYC QSYDSSLSGT VFGGGTKLTV LG         112

SEQ ID NO: 40           moltype = AA  length = 217
FEATURE                 Location/Qualifiers
REGION                  1..217
                        note = YN-038 light chain
source                  1..217
                        mol_type = protein
```

```
                          organism = synthetic construct
SEQUENCE: 40
QSALTQPASV SGSPGQSITI SCTGTRSDVG GYNEVSWYQQ HPGKAPKLMI YENSIRPSGV  60
SHRFSGSKSG NTASLTISGL QAEDEADYYC QSYDSSLSGT VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 41             moltype = AA  length = 112
FEATURE                   Location/Qualifiers
REGION                    1..112
                          note = YN-039VL
source                    1..112
                          mol_type = protein
                          organism = synthetic construct
SEQUENCE: 41
QSALTQPASV SGSPGQSITI SCTGTVSDVG GYNEVSWYQQ HPGKAPKLMI YENSIRPSGV  60
SHRFSGSKSG NTASLTISGL QAEDEADYYC QSYDSSLSGT VFGGGTKLTV LG          112

SEQ ID NO: 42             moltype = AA  length = 217
FEATURE                   Location/Qualifiers
REGION                    1..217
                          note = YN-039 light chain
source                    1..217
                          mol_type = protein
                          organism = synthetic construct
SEQUENCE: 42
QSALTQPASV SGSPGQSITI SCTGTVSDVG GYNEVSWYQQ HPGKAPKLMI YENSIRPSGV  60
SHRFSGSKSG NTASLTISGL QAEDEADYYC QSYDSSLSGT VFGGGTKLTV LGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                           217

SEQ ID NO: 43             moltype = AA  length = 713
FEATURE                   Location/Qualifiers
REGION                    1..713
                          note = first polypeptide of YN-051
source                    1..713
                          mol_type = protein
                          organism = synthetic construct
SEQUENCE: 43
QVQLVQSGAE VKKPGSSVKV SCKASRGPFS TYAISWVRQA PGQGLEWMGR IIPILGIANY  60
AQKFQGRVTI TADKSTSTAY MELSSLRSED TAVYYCARTM EGYGFGNFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
ASTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG GGGSGGGGSG GGGSQVQLVE SGGGLVQPGG  480
SLRLSCAASG FTFSSYAMSW VRQAPGKGLE WVSAISGSGG STYYADSVKG RFTISRDNSK  540
NTLYLQMNSL RAEDTAVYYC AKTNWGPSDA FDIWGQGTMV TVSSASTGGG GSGGGGSGGG  600
GSQSVLTQPP SASGTPGQRV TISCSGSTSD IGSYSVNWYQ QLPGTAPKLL IYSNNQRPSG  660
VPDRFSGSKS GTSASLAISG LQSEDEADYY CAAWDDSLNG YVFGTGTKLT VLG         713

SEQ ID NO: 44             moltype = AA  length = 713
FEATURE                   Location/Qualifiers
REGION                    1..713
                          note = first polypeptide of YN-052
source                    1..713
                          mol_type = protein
                          organism = synthetic construct
SEQUENCE: 44
QVQLVQSGAE VKKPGSSVKV SCKASRGPFS TYAISWVRQA PGQGLEWMGR IIPILGIANY  60
AQKFQGRVTI TADKSTSTAY MELSSLRSED TAVYYCARTM GEYSYGNYDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
ASTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG GGGSGGGGSG GGGSQVQLVE SGGGLVQPGG  480
SLRLSCAASG FTFSSYAMSW VRQAPGKGLE WVSAISGSGG STYYADSVKG RFTISRDNSK  540
NTLYLQMNSL RAEDTAVYYC AKTNWGPSDA FDIWGQGTMV TVSSASTGGG GSGGGGSGGG  600
GSQSVLTQPP SASGTPGQRV TISCSGSTSD IGSYSVNWYQ QLPGTAPKLL IYSNNQRPSG  660
VPDRFSGSKS GTSASLAISG LQSEDEADYY CAAWDDSLNG YVFGTGTKLT VLG         713

SEQ ID NO: 45             moltype = AA  length = 5
FEATURE                   Location/Qualifiers
REGION                    1..5
                          note = HCDR1 of PD-L1 antibody
SITE                      1
                          note = X1 - X1 is S or T
```

```
source                  1..5
                        mol_type = protein
                        organism = synthetic construct
SEQUENCE: 45
XYAIS                                                                      5

SEQ ID NO: 46           moltype = AA  length = 5
FEATURE                 Location/Qualifiers
REGION                  1..5
                        note = HCDR1 of YN-002; HCDR1 of YN-003
source                  1..5
                        mol_type = protein
                        organism = synthetic construct
SEQUENCE: 46
SYAIS                                                                      5

SEQ ID NO: 47           moltype = AA  length = 5
FEATURE                 Location/Qualifiers
REGION                  1..5
                        note = HCDR1 of YN-035; HCDR1 of YN-036; HCDR1 of YN-037;
                         HCDR1 ofYN-038; HCDR1 of YN-039
source                  1..5
                        mol_type = protein
                        organism = synthetic construct
SEQUENCE: 47
TYAIS                                                                      5

SEQ ID NO: 48           moltype = AA  length = 17
FEATURE                 Location/Qualifiers
REGION                  1..17
                        note = HCDR2 of YN-002; HCDR2 of YN-003 ; HCDR2 of YN-035 ;
                         HCDR2 ofYN-036 ; HCDR2 of YN-037 ; HCDR2 of YN-038 ; HCDR2
                         of YN-039 ;HCDR2 of PD-L1 antibody
source                  1..17
                        mol_type = protein
                        organism = synthetic construct
SEQUENCE: 48
RIIPILGIAN YAQKFQG                                                         17

SEQ ID NO: 49           moltype = AA  length = 12
FEATURE                 Location/Qualifiers
REGION                  1..12
                        note = HCDR3 of PD-L1 antibody
SITE                    3
                        note = X1 - X1is DE or G
SITE                    4
                        note = X2 - X2 is G or E
SITE                    6
                        note = X3 - X3 is S or G
SITE                    7
                        note = X4 - X4 is Y or F
SITE                    10
                        note = X5 - X5 is F or Y
source                  1..12
                        mol_type = protein
                        organism = synthetic construct
SEQUENCE: 49
TMXXYXXGNX DY                                                              12

SEQ ID NO: 50           moltype = AA  length = 12
FEATURE                 Location/Qualifiers
REGION                  1..12
                        note = HCDR3 of YN-002; HCDR3 of YN-003
source                  1..12
                        mol_type = protein
                        organism = synthetic construct
SEQUENCE: 50
TMDGYSYGNF DY                                                              12

SEQ ID NO: 51           moltype = AA  length = 12
FEATURE                 Location/Qualifiers
REGION                  1..12
                        note = HCDR3 of YN-035
source                  1..12
                        mol_type = protein
                        organism = synthetic construct
SEQUENCE: 51
TMEGYGFGNF DY                                                              12
```

```
SEQ ID NO: 52           moltype = AA  length = 12
FEATURE                 Location/Qualifiers
REGION                  1..12
                        note = HCDR3 of YN-036 ; HCDR3 of YN-037 ; HCDR3 of YN-038
                         ; HCDR3 ofYN-039
source                  1..12
                        mol_type = protein
                        organism = synthetic construct
SEQUENCE: 52
TMGEYSYGNY DY                                                             12

SEQ ID NO: 53           moltype = AA  length = 14
FEATURE                 Location/Qualifiers
REGION                  1..14
                        note = LCDR1 of PD-L1 antibody
SITE                    4
                        note = X1 - X1 is SR or V
SITE                    6
                        note = X2 - X2 is DE or S
SITE                    11
                        note = X3 - X3 is N or R
SITE                    12
                        note = X4 - X4 is Y or E
source                  1..14
                        mol_type = protein
                        organism = synthetic construct
SEQUENCE: 53
TGTXSXVGGY XXVS                                                           14

SEQ ID NO: 54           moltype = AA  length = 14
FEATURE                 Location/Qualifiers
REGION                  1..14
                        note = LCDR1 of YN-002; LCDR1 of YN-003
source                  1..14
                        mol_type = protein
                        organism = synthetic construct
SEQUENCE: 54
TGTSSDVGGY NYVS                                                           14

SEQ ID NO: 55           moltype = AA  length = 14
FEATURE                 Location/Qualifiers
REGION                  1..14
                        note = LCDR1 of YN-035 ; LCDR1 of YN-036
source                  1..14
                        mol_type = protein
                        organism = synthetic construct
SEQUENCE: 55
TGTVSEVGGY NEVS                                                           14

SEQ ID NO: 56           moltype = AA  length = 14
FEATURE                 Location/Qualifiers
REGION                  1..14
                        note = LCDR1 of YN-037
source                  1..14
                        mol_type = protein
                        organism = synthetic construct
SEQUENCE: 56
TGTSSSVGGY REVS                                                           14

SEQ ID NO: 57           moltype = AA  length = 14
FEATURE                 Location/Qualifiers
REGION                  1..14
                        note = LCDR1 of YN-038
source                  1..14
                        mol_type = protein
                        organism = synthetic construct
SEQUENCE: 57
TGTRSDVGGY NEVS                                                           14

SEQ ID NO: 58           moltype = AA  length = 14
FEATURE                 Location/Qualifiers
REGION                  1..14
                        note = LCDR1 of YN-039
source                  1..14
                        mol_type = protein
                        organism = synthetic construct
SEQUENCE: 58
TGTVSDVGGY NEVS                                                           14
```

```
SEQ ID NO: 59          moltype = AA  length = 7
FEATURE                Location/Qualifiers
REGION                 1..7
                       note = LCDR2 of PD-L1 antibody
SITE                   1
                       note = X1 - X1 is G or E
SITE                   4
                       note = X2 - X2 is N or I
source                 1..7
                       mol_type = protein
                       organism = synthetic construct
SEQUENCE: 59
XNSXRPS                                                             7

SEQ ID NO: 60          moltype = AA  length = 7
FEATURE                Location/Qualifiers
REGION                 1..7
                       note = LCDR2of YN-002; LCDR2of YN-003 ; LCDR2of YN-035 ;
                        LCDR2ofYN-036
source                 1..7
                       mol_type = protein
                       organism = synthetic construct
SEQUENCE: 60
GNSNRPS                                                             7

SEQ ID NO: 61          moltype = AA  length = 7
FEATURE                Location/Qualifiers
REGION                 1..7
                       note = LCDR2of YN-037 ; LCDR2of YN-038 ; LCDR2of YN-039
source                 1..7
                       mol_type = protein
                       organism = synthetic construct
SEQUENCE: 61
ENSIRPS                                                             7

SEQ ID NO: 62          moltype = AA  length = 11
FEATURE                Location/Qualifiers
REGION                 1..11
                       note = LCDR3 of PD-L1 antibody
SITE                   10
                       note = X1 - X1 is S or T
source                 1..11
                       mol_type = protein
                       organism = synthetic construct
SEQUENCE: 62
QSYDSSLSGX V                                                        11

SEQ ID NO: 63          moltype = AA  length = 11
FEATURE                Location/Qualifiers
REGION                 1..11
                       note = LCDR3 of YN-002 ; LCDR3 of YN-003
source                 1..11
                       mol_type = protein
                       organism = synthetic construct
SEQUENCE: 63
QSYDSSLSGS V                                                        11

SEQ ID NO: 64          moltype = AA  length = 11
FEATURE                Location/Qualifiers
REGION                 1..11
                       note = LCDR3 of YN-035 ; LCDR3 of YN-036 ; LCDR3 of YN-037
                        ; LCDR3 ofYN-038 ; LCDR3 of YN-039
source                 1..11
                       mol_type = protein
                       organism = synthetic construct
SEQUENCE: 64
QSYDSSLSGT V                                                        11

SEQ ID NO: 65          moltype = AA  length = 30
FEATURE                Location/Qualifiers
REGION                 1..30
                       note = H-FR1 of YN-002
source                 1..30
                       mol_type = protein
                       organism = synthetic construct
SEQUENCE: 65
QVQLVQSGAE VRKPGSSVKV SCKASGGTFS                                    30

SEQ ID NO: 66          moltype = AA  length = 30
```

```
FEATURE                Location/Qualifiers
REGION                 1..30
                       note = H-FR1 of YN-003
source                 1..30
                       mol_type = protein
                       organism = synthetic construct
SEQUENCE: 66
QVQLVQSGAE VKKPGSSVKV SCKASGGTFS                                  30

SEQ ID NO: 67          moltype = AA  length = 30
FEATURE                Location/Qualifiers
REGION                 1..30
                       note = H-FR1 of YN-035~YN-039
source                 1..30
                       mol_type = protein
                       organism = synthetic construct
SEQUENCE: 67
QVQLVQSGAE VKKPGSSVKV SCKASRGPFS                                  30

SEQ ID NO: 68          moltype = AA  length = 14
FEATURE                Location/Qualifiers
REGION                 1..14
                       note = H-FR2 of YN-002; H-FR2 of YN-003; H-FR2 of
                        YN-035~YN-039
source                 1..14
                       mol_type = protein
                       organism = synthetic construct
SEQUENCE: 68
WVRQAPGQGL EWMG                                                   14

SEQ ID NO: 69          moltype = AA  length = 32
FEATURE                Location/Qualifiers
REGION                 1..32
                       note = H-FR3 of YN-002; H-FR3 of YN-003; H-FR3 of
                        YN-035~YN-039
source                 1..32
                       mol_type = protein
                       organism = synthetic construct
SEQUENCE: 69
RVTITADKST STAYMELSSL RSEDTAVYYC AR                               32

SEQ ID NO: 70          moltype = AA  length = 11
FEATURE                Location/Qualifiers
REGION                 1..11
                       note = H-FR4 of YN-002; H-FR4 of YN-003; H-FR4 of
                        YN-035~YN-039
source                 1..11
                       mol_type = protein
                       organism = synthetic construct
SEQUENCE: 70
WGQGTLVTVS S                                                      11

SEQ ID NO: 71          moltype = AA  length = 22
FEATURE                Location/Qualifiers
REGION                 1..22
                       note = L-FR1 of YN-002; L-FR1 of YN-003; L-FR1 of
                        YN-035~YN-039
source                 1..22
                       mol_type = protein
                       organism = synthetic construct
SEQUENCE: 71
QSALTQPASV SGSPGQSITI SC                                          22

SEQ ID NO: 72          moltype = AA  length = 15
FEATURE                Location/Qualifiers
REGION                 1..15
                       note = L-FR2 of YN-002; L-FR2 of YN-003; L-FR2 of
                        YN-035~YN-039
source                 1..15
                       mol_type = protein
                       organism = synthetic construct
SEQUENCE: 72
WYQQHPGKAP KLMIY                                                  15

SEQ ID NO: 73          moltype = AA  length = 32
FEATURE                Location/Qualifiers
REGION                 1..32
                       note = L-FR3 of YN-002
source                 1..32
```

```
                         mol_type = protein
                         organism = synthetic construct
SEQUENCE: 73
GVPDRFSGSK SGTSASLAIT GLQAEDEADY YC                                    32

SEQ ID NO: 74            moltype = AA  length = 32
FEATURE                  Location/Qualifiers
REGION                   1..32
                         note = L-FR3 of YN-003; L-FR3 of YN-035~YN-036
source                   1..32
                         mol_type = protein
                         organism = synthetic construct
SEQUENCE: 74
GVSNRFSGSK SGNTASLTIS GLQAEDEADY YC                                    32

SEQ ID NO: 75            moltype = AA  length = 32
FEATURE                  Location/Qualifiers
REGION                   1..32
                         note = L-FR3 of YN-037~YN-039
source                   1..32
                         mol_type = protein
                         organism = synthetic construct
SEQUENCE: 75
GVSHRFSGSK SGNTASLTIS GLQAEDEADY YC                                    32

SEQ ID NO: 76            moltype = AA  length = 11
FEATURE                  Location/Qualifiers
REGION                   1..11
                         note = L-FR4 ofYN-002; L-FR4 of YN-003; L-FR4 of
                          YN-035~YN-039
source                   1..11
                         mol_type = protein
                         organism = synthetic construct
SEQUENCE: 76
FGGGTKLTVL G                                                           11

SEQ ID NO: 77            moltype = AA  length = 5
FEATURE                  Location/Qualifiers
REGION                   1..5
                         note = 4-1BB antibody YN-005/006 H-CDR1
source                   1..5
                         mol_type = protein
                         organism = synthetic construct
SEQUENCE: 77
SYAMS                                                                  5

SEQ ID NO: 78            moltype = AA  length = 17
FEATURE                  Location/Qualifiers
REGION                   1..17
                         note = 4-1BB antibody YN-005/006 H-CDR2
source                   1..17
                         mol_type = protein
                         organism = synthetic construct
SEQUENCE: 78
AISGSGGSTY YADSVKG                                                     17

SEQ ID NO: 79            moltype = AA  length = 11
FEATURE                  Location/Qualifiers
REGION                   1..11
                         note = 4-1BB antibody YN-005/006 H-CDR3
source                   1..11
                         mol_type = protein
                         organism = synthetic construct
SEQUENCE: 79
TNWGPSDAFD I                                                           11

SEQ ID NO: 80            moltype = AA  length = 13
FEATURE                  Location/Qualifiers
REGION                   1..13
                         note = 4-1BB antibody YN-005/006 L-CDR1
source                   1..13
                         mol_type = protein
                         organism = synthetic construct
SEQUENCE: 80
SGSTSDIGSY SVN                                                         13

SEQ ID NO: 81            moltype = AA  length = 7
FEATURE                  Location/Qualifiers
REGION                   1..7
```

```
                        note = 4-1BB antibody YN-005/006 L-CDR2
source                  1..7
                        mol_type = protein
                        organism = synthetic construct
SEQUENCE: 81
SNNQRPS                                                       7

SEQ ID NO: 82           moltype = AA  length = 11
FEATURE                 Location/Qualifiers
REGION                  1..11
                        note = 4-1BB antibody YN-005/006 L-CDR3
source                  1..11
                        mol_type = protein
                        organism = synthetic construct
SEQUENCE: 82
AAWDDSLNGY V                                                  11

SEQ ID NO: 83           moltype = AA  length = 249
FEATURE                 Location/Qualifiers
REGION                  1..249
                        note = 4-1BB antibody scFv
source                  1..249
                        mol_type = protein
                        organism = synthetic construct
SEQUENCE: 83
QVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKTN WGPSDAFDIW GQGTMVTVSS  120
ASTGGGGSGG GGSGGGGSQS VLTQPPSASG TPGQRVTISC SGSTSDIGSY SVNWYQQLPG  180
TAPKLLIYSN NQRPSGVPDR FSGSKSGTSA SLAISGLQSE DEADYYCAAW DDSLNGYVFG  240
TGTKLTVLG                                                     249

SEQ ID NO: 84           moltype = AA  length = 30
FEATURE                 Location/Qualifiers
REGION                  1..30
                        note = 4-1BB antibody YN-005 H-FR1
source                  1..30
                        mol_type = protein
                        organism = synthetic construct
SEQUENCE: 84
QVQLVQSGGG LVQPGGSLRL SCAASGFTFS                              30

SEQ ID NO: 85           moltype = AA  length = 30
FEATURE                 Location/Qualifiers
REGION                  1..30
                        note = 4-1BB antibody YN-006 H-FR1
source                  1..30
                        mol_type = protein
                        organism = synthetic construct
SEQUENCE: 85
QVQLVESGGG LVQPGGSLRL SCAASGFTFS                              30

SEQ ID NO: 86           moltype = AA  length = 14
FEATURE                 Location/Qualifiers
REGION                  1..14
                        note = 4-1BB antibody YN-005/006 H-FR2
source                  1..14
                        mol_type = protein
                        organism = synthetic construct
SEQUENCE: 86
WVRQAPGKGL EWVS                                               14

SEQ ID NO: 87           moltype = AA  length = 32
FEATURE                 Location/Qualifiers
REGION                  1..32
                        note = 4-1BB antibody YN-005/006 H-FR3
source                  1..32
                        mol_type = protein
                        organism = synthetic construct
SEQUENCE: 87
RFTISRDNSK NTLYLQMNSL RAEDTAVYYC AK                           32

SEQ ID NO: 88           moltype = AA  length = 11
FEATURE                 Location/Qualifiers
REGION                  1..11
                        note = 4-1BB antibody YN-005/006 H-FR4
source                  1..11
                        mol_type = protein
                        organism = synthetic construct
SEQUENCE: 88
```

```
WGQGTMVTVS S                                                11

SEQ ID NO: 89           moltype = AA  length = 22
FEATURE                 Location/Qualifiers
REGION                  1..22
                        note = 4-1BB antibody YN-005/006 L-FR1
source                  1..22
                        mol_type = protein
                        organism = synthetic construct
SEQUENCE: 89
QSVLTQPPSA SGTPGQRVTI SC                                    22

SEQ ID NO: 90           moltype = AA  length = 15
FEATURE                 Location/Qualifiers
REGION                  1..15
                        note = 4-1BB antibody YN-005/006 L-FR2
source                  1..15
                        mol_type = protein
                        organism = synthetic construct
SEQUENCE: 90
WYQQLPGTAP KLLIY                                            15

SEQ ID NO: 91           moltype = AA  length = 32
FEATURE                 Location/Qualifiers
REGION                  1..32
                        note = 4-1BB antibody YN-005/006 L-FR3
source                  1..32
                        mol_type = protein
                        organism = synthetic construct
SEQUENCE: 91
GVPDRFSGSK SGTSASLAIS GLQSEDEADY YC                         32

SEQ ID NO: 92           moltype = AA  length = 11
FEATURE                 Location/Qualifiers
REGION                  1..11
                        note = 4-1BB antibody YN-005/006 L-FR4
source                  1..11
                        mol_type = protein
                        organism = synthetic construct
SEQUENCE: 92
FGTGTKLTVL G                                                11

SEQ ID NO: 93           moltype = AA  length = 118
FEATURE                 Location/Qualifiers
source                  1..118
                        mol_type = protein
                        organism = synthetic construct
REGION                  1..118
                        note = Germline IGHV 1-69
SEQUENCE: 93
QVQLVQSGAE VKKPGSSVKV SCKASGGTFS SYAISWVRQA PGQGLEWMGR IIPILGIANY  60
AQKFQGRVTI TADKSTSTAY MELSSLRSED TAVYYCARGY SYGNFDYWGQ GTLVTVSS    118

SEQ ID NO: 94           moltype = AA  length = 108
FEATURE                 Location/Qualifiers
source                  1..108
                        mol_type = protein
                        organism = synthetic construct
REGION                  1..108
                        note = Germline IGLV 2-14
SEQUENCE: 94
QSALTQPASV SGSPGQSITI SCTGTSSDVG GYNYVSWYQQ HPGKAPKLMI YEVSNRPSGV  60
SNRFSGSKSG NTASLTISGL QAEDEADYYC SSYTSSVFGG GTKLTVLG            108

SEQ ID NO: 95           moltype = AA  length = 118
FEATURE                 Location/Qualifiers
source                  1..118
                        mol_type = protein
                        organism = synthetic construct
REGION                  1..118
                        note = Germline IGHV 3-23
SEQUENCE: 95
QVQLVESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKTN WGDAFDIWGQ GTMVTVSS    118

SEQ ID NO: 96           moltype = AA  length = 111
FEATURE                 Location/Qualifiers
source                  1..111
                        mol_type = protein
```

-continued

```
                     organism = synthetic construct
REGION               1..111
                     note = Germline IGLV 1-44
SEQUENCE: 96
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYCA AWDDSLNGYV FGTGTKLTVL G          111
```

ANTI-PD-L1 ANTIBODY AND USE THEREOF

CROSS-REFERENCE TO RELATED APPLICATIONS

The present application is a continuation application of non-provisional U.S. application Ser. No. 17/046,265, file Oct. 8, 2020, which is a 35 U.S.C. § 371 national stage patent application of International patent application PCT/CN2018/102584, filed on Aug. 27, 2018, which is based on and claims the benefits of priority to Chinese Application No. 201810309302.5, filed on Apr. 9, 2018. The entire contents of all of the above applications are incorporated herein by reference.

REFERENCE TO A SEQUENCE LISTING

In accordance with 37 CFR § 1.833-1835 and 37 CFR § 1.77(b)(5), the specification makes reference to a Sequence Listing submitted electronically as a .xml file named "20250609_0065-PA-015USDIV2_Sequence_Listing.xml". The .xml file was generated on Jun. 24, 2025 and is 145,000 bytes in size. The entire contents of the Sequence Listing are hereby incorporated by reference.

TECHNICAL FIELD

The present application relates to the biomedical field, especially to an anti-PD-L1 antibody, further relates to a method of treating cancers by using such antibody in combination with an anti-CD137 antibody, and further relates to a bispecific antibody formed by such antibody and an anti-CD137 antibody.

BACKGROUND

Programmed death-1 (PD-1, also known as CD279) and its ligands PD-L1 (also known as B7-H1, CD274) and PD-L2 (also known as B7-DC, CD273) cooperate to provide a negative co-stimulatory signal to regulate the activation of T cells. In the absence of the co-stimulatory signal, T cells are hard to feel antigenic stimulation, cannot provide an effective immune response, and can also result in exhaustion or tolerance to heterogeneous antigens. PD-1 can be expressed in T cells, B cells, natural killer T cells, activated mononuclear cells and dendritic cells (DCs). PD-1 can be expressed by activated, but not stimulated human $CD4^+$ and $CD8^+$ T cells, B cells and bone marrow cells. PD-L1 and PD-L2 are different from each other in their expression modes. PD-L1 can be expressed in not only hematopoietic cells, but also in a variety of non-hematopoietic cells, wherein the expression of PD-L2 is primarily limited in dendritic cells and macrophages. B7.1 (CD80) is also a PD-L1 receptor that is expressed in activated B cells, T cells, macrophages and dendritic cell. As the ligands of PD-1 and B7.1, PD-L1 is also selectively expressed in a variety of tumor cells. Inhibition of PD-L1 signal transduction includes blocking the interaction between PD-L1 and either or both of PD-1 and B7.1, thereby preventing PD-L1 from sending a negative co-stimulatory signal to T cells and other antigen-presenting cells. It may enhance the immune to infection (e.g., acute or chronic) response and the tumor immune.

CD137 (also known as 4-1BB, TNERSF9, etc.) is a transmembrane protein of tumor necrosis factor superfamily (TNFRS). Studies indicate that CD137-activated monoclonal antibody increases the expression of co-stimulatory molecules in many models, significantly enhances the response of cytolytic T lymphocytes, and plays an antitumor role. The antitumor effect of CD137-targeted therapies is demonstrated by studies involving the antitumor therapeutic effect of activated anti-mouse CD137 monoclonal antibody in mice.

Currently, PD-L1 antibodies have been approved for use in treating some cancers, and the existing CD137 antibodies exhibit a potential of treating a variety of tumors. It has been reported that the antitumor therapeutic effect of PD-1 antibody in combination with CD137 antibody is studied by use of tumor-bearing mouse model. The results show that the two antibodies used in combination exhibit a significantly enhanced tumor-inhibiting activity as compared with them used alone, but from the viewpoint of compliance and pain, the combination therapy brings inconvenience to patients and increases treatment costs. Development of bispecific antibody (BsAb) of the two monoclonal antibodies can solve the aforesaid problem due to the presence of two specific antigen-binding sites in the bispecific antibody. Thus, there is an urgent need of developing a novel anti-PD-L1 antibody having better pharmaceutical efficacy and lower immunogenicity and a PD-L1/CD137 bispecific antibody to give a better antitumor effect.

SUMMARY OF THE INVENTION

The present application provides a PD-L1 antibody, an antigen binding fragment or a variant thereof which have one or more of the following properties: 1) capable of binding the PD-L1 protein with high affinity and specificity: 2) capable of inhibiting the binding of the PD-1 protein to the PD-L1 protein; and 3) capable of relieving or treating tumors. The present application further provides a bispecific antibody having one or more of the following properties: 1) capable of binding to the PD-L1 protein with high affinity and specificity; 2) capable of binding to the CD137 protein with high affinity and specificity: 3) capable of enhancing the functions of T cells, and 4) capable of relieving or treating tumor. The present application further provides a preparation method and use of the PD-L1 antibody, the antigen binding fragment or the variant thereof, bispecific antibody.

In one aspect, the present application provides an antibody, an antigen binding fragment or a variant thereof which binds to the PD-L1 protein with a $K_D$ of $3\times10^{-9}$ M or less.

In some embodiments, the antibody includes an antibody light chain or a fragment thereof which includes a LCDR1, and the LCDR1 includes an amino acid sequence shown in SEQ ID NO: 53: $TGTX_1SX_2VGGYX_3X_4VS$; wherein $X_1$ is S, R or V; $X_2$ is D, E or S; $X_3$ is N or R; $X_4$ is Y or E, and wherein the LCDR1 is determined according to the index of the antibody Kabat number.

In some embodiments, the LCDR1 includes an amino acid sequence selected from the group consisting of SEQ ID NO: 54-58. In some embodiments, the antibody light chain or the fragment thereof includes a LCDR2 including an amino acid sequence shown in SEQ ID NO: 59; $X_1NSX_2RPS$, wherein $X_1$ is G or E; $X_2$ is N or I, and wherein the LCDR2 is determined according to the index of the antibody Kabat number. In some embodiments, the LCDR2 includes an amino acid sequence selected from the group consisting of SEQ ID NO: 60-61. In some embodiments, the antibody light chain or the fragment thereof includes a LCDR3 including an amino acid sequence shown in SEQ ID NO: 62: $QSYDSSLSOX_1V$, wherein $X_1$ is S or T, and wherein the LCDR3 is determined according to the index of the antibody Kabat number.

In some embodiments, the antibody light chain or a fragment thereof further includes framework regions L-FR1, L-FR2, L-FR3, and L-FR4. In some embodiments, the framework regions are selected from the group consisting of human consensus framework sequences and human germline sequences. In some embodiments, a C-terminus of the L-PR1 is directly or indirectly linked to an N-terminus of the LCDR1, and the L-FR1 includes an amino acid sequence selected from the group consisting of SEQ ID NO: 71. In some embodiments, the L-FR2 is located between the LCDR1 and the LCDR2, and the L-FR2 includes an amino acid sequence selected from the group consisting of SEQ ID NO: 72. In some embodiments, the L-FR3 is located between the LCDR2 and the LCDR3, and the L-FR3 includes an amino acid sequence selected from the group consisting of SEQ ID NO: 73-75. In some embodiments, the N-terminus of the L-FR4 is directly or indirectly linked to the C-terminus of the LCDR3, and the L-FR4 includes an amino acid sequence selected from the group consisting of SEQ ID NO: 76.

In some embodiments, the antibody light chain or the fragment thereof includes a light chain variable region VL, and the light chain variable region VL includes an amino acid sequence selected from the group consisting of SEQ ID NO: 4, SEQ ID NO: 11, SEQ ID NO: 33, SEQ ID NO: 37, SEQ ID NO: 39 and SEQ ID NO: 41.

In some embodiments, the antibody light chain or the fragment thereof further includes a human constant region, and the human constant region includes a human Igλ constant region.

In some embodiments, the antibody light chain or the fragment thereof includes an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

In some embodiments, the antibody includes an antibody heavy chain or a fragment thereof which includes a HCDR1, and the HCDR1 includes an amino acid sequence selected from the group consisting of those shown in SEQ ID NO: 45; $X_1$YA1S, wherein $X_1$ is S or T, and wherein the HCDR1 is determined according to the index of the antibody Kabat number. In some embodiments, the antibody heavy chain or a fragment thereof includes a HCDR2, the HCDR2 includes an amino acid sequence shown in SEQ ID NO: 48, and wherein the HCDR2 is determined according to the index of the antibody Kabat number. In some embodiments, the antibody heavy chain or a fragment thereof includes a HCDR3, and the HCDR3 includes an amino acid sequence selected from the group consisting of those shown in SEQ ID NO: 49: TM$X_1X_2$Y$X_3X_4$GN$X_5$DY, wherein $X_1$ is D, E or G, $X_2$ is G or E, $X_3$ is S or G, $X_4$ is Y or F, $X_5$ is F or Y, and wherein the HCDR3 is determined according to the index of the antibody Kabat number. In some embodiments, the HCDR3 includes an amino acid sequence shown in the group of SEQ ID NO: 50-52.

In some embodiments, the antibody heavy chain or the fragment thereof further includes framework regions H-FR1, H-FR2, H-FR3, and H-FR4. In some embodiments, the framework regions are selected from the group consisting of human consensus framework sequences and human germline sequences. In some embodiments, a C-terminus of H-FR1 is directly or indirectly linked to an N-terminus of HCDR1, and the H-FR1 includes an amino acid sequence selected from the group consisting of SEQ ID NO: 65-67. In some embodiments, the H-FR2 is located between the HCDR1 and the HCDR2, and the H-FR2 includes an amino acid sequence selected from the group consisting of SEQ ID NO: 68. In some embodiments, the H-FR3 is located between the HCDR2 and the HCDR3, and the H-FR3 includes an amino acid sequence selected from the group consisting of SEQ ID NO: 69. In some embodiments, the N-terminus of H-FR4 is directly or indirectly linked to the C-terminus of HCDR3, and the H-FR4 includes an amino acid sequence selected from the group consisting of SEQ ID NO: 70.

In some embodiments, the antibody heavy chain or the fragment thereof includes a heavy chain variable region VH, and the heavy chain variable region VH includes an amino acid sequence selected from the group consisting of SEQ ID NO: 2, SEQ ID NO: 9, SEQ ID NO: 31 and SEQ ID NO: 35.

In some embodiments, the antibody heavy chain or the fragment thereof further includes a human constant region, and the human constant region includes a human IgG1 constant region.

In some embodiments, the antibody heavy chain or the fragment thereof includes an amino acid sequence selected from the group consisting of SEQ ID NO: 6, SEQ ID NO: 13, SEQ ID NO: 32 and SEQ ID NO: 36.

In some embodiments, the PD-L1 protein is selected from the group consisting of human PD-L1 protein, monkey PD-L1 protein and murine PD-L1 protein.

In another aspect, the present application provides an antibody, an antigen binding fragment or a variant thereof which binds to a CD137 protein with a $K_D$ of $5\times10^{-9}$ M or less.

In some embodiments, the antibody, the antigen binding fragment or the variant thereof binds to a CD137 protein with a $K_D$ of $3\times10^{-9}$ M or less.

In some embodiments, the antibody, the antigen binding fragment or the variant thereof may relieve or treat tumors. In some embodiments, the antibody, the antigen binding fragment or the variant thereof may relieve or treat colon cancer.

In some embodiments, the antibody includes an antibody light chain or a fragment, thereof. In some embodiments, the light chain or the fragment thereof includes LCDR1-3, and the amino acid sequences of LCDR1-3 are sequentially shown in SEQ ID NO: 80-82. In some embodiments, the antibody light chain or the fragment thereof further includes framework regions L-FR1, L-FR2, L-FR3 and L-FR4, In some embodiments, the framework regions are selected from the group consisting of human consensus framework sequences and human germline sequences. In some embodiments, a C-terminus of the L-FR1 is directly or indirectly linked to an N-terminus of the LCDR1, and the L-FR1 includes an amino acid sequence shown in SEQ ID NO: 89. In some embodiments, the L-FR2 is located between the LCDR1 and the LCDR2, and the L-FR2 includes an amino acid sequence shown in SEQ ID NO: 90. In some embodiments, the L-FR3 is located between the LCDR2 and the LCDR3, and the L-FR3 includes an amino acid sequence shown in SEQ ID NO: 91. In some embodiments, the N-terminus of the L-FR4 is directly or indirectly linked to the C-terminus of the LCDR3, and the L-FR4 includes an amino acid sequence shown in SEQ ID NO: 92.

In some embodiments, the antibody light chain or the fragment thereof includes a light chain variable region VL, and the light chain variable region VL includes an amino acid sequence shown in SEQ ID NO: 20.

In some embodiments, the antibody light chain or the fragment thereof further includes a human constant region and the human constant region includes a human Igλ constant region.

In some embodiments, the antibody light chain or the fragment thereof includes an amino acid sequence shown in SEQ ID NO: 23.

In some embodiments, the antibody includes an antibody heavy chain or a fragment thereof, wherein the heavy chain or the fragment thereof includes HCDR1-3, and the amino acid sequences of the HCDR1-3 are sequentially shown in SEQ ID NO: 77-79. In some embodiments, the antibody heavy chain or the fragment thereof further includes framework regions H-FR1, H-FR2, H-FR3 and H-FR4. In some embodiments, the framework regions are selected from the group consisting of human consensus framework sequences and human germline sequences. In some embodiments, a C-terminus of H-FR1 is directly or indirectly linked to an N-terminus of HCDR1, and the H-FR1 includes an amino acid sequence shown in SEQ ID NO: 84-85. In some embodiments, the H-FR2 is located between the HCDR1 and the HCDR2, and the H-FR2 includes an amino acid sequence shown in SEQ ID NO: 86. In some embodiments, the H-FR3 is located between the HCDR2 and the HCDR3, and the H-FR3 includes an amino acid sequence shown in SEQ ID NO: 87. In some embodiments, the N-terminus of H-FR4 is directly or indirectly linked to the C-terminus of HCDR3, and the H-FR4 includes an amino acid sequence shown in SEQ ID NO: 88.

In some embodiments, the antibody heavy chain or the fragment thereof includes a heavy chain variable region VH, and the heavy chain variable region VH includes an amino acid sequence selected from the group consisting of SEQ ID NO: 18 and SEQ ID NO: 25.

In some embodiments, the antibody heavy chain or the fragment thereof further includes a human constant region, and the human constant region includes a human IgG constant region.

In some embodiments, the antibody heavy chain or the fragment thereof includes an amino acid sequence selected from the group consisting of SEQ ID NO: 21 and SEQ ID NO: 27.

In some embodiments, the CD137 protein includes a human CD137 protein.

In another aspect, the present application provides a bispecific antibody which binds to a PD-L1 protein with a $K_D$ of $2\times10^{-9}$ M or less and binds to a CD137 protein with a $K_D$ of $8\times10^{-9}$ M or less.

In some embodiments, the bispecific antibody includes a first targeting moiety that specifically binds to the PD-L1 protein, wherein the first targeting moiety includes the antibody, the antigen binding fragment or the variant thereof.

In some embodiments, the bispecific antibody includes a second targeting moiety that specifically binds to the CD137 protein, wherein the second targeting moiety includes an antibody, an antigen binding fragment or a variant thereof which binds to the CD137 protein. In some embodiments, the antibody that binds to the CD137 protein includes a scFv, and the scFv includes an amino acid sequence shown in SEQ ID NO: 83. In some embodiments, the bispecific antibody includes a first polypeptide chain and a second polypeptide chain, wherein the first polypeptide chain includes the heavy chain variable region of the antibody that binds to the PD-L1 protein, the heavy chain variable region of the antibody that binds to the CD137 protein, and the light chain variable region of the antibody that binds to the CD137 protein; and the second polypeptide chain includes the light chain variable region of the antibody that binds to the PD-L1 protein.

In some embodiments, in the first polypeptide chain, the heavy chain variable region of the antibody that binds to the PD-L1 protein is located at an N-terminus of the heavy chain variable region of the antibody that binds to the CD137 protein, and the heavy chain variable region of the antibody that binds to the CD137 protein is located at the N-terminus of the light chain variable region of the antibody that binds to the CD137 protein; alternatively, the heavy chain variable region of the antibody that binds to the PD-L1 protein is located at the N-terminus of the light chain variable region of the antibody that binds to the CD137 protein, and the light chain variable region of the antibody that binds to the CD137 protein is located at the N-terminus of the heavy chain variable region of the antibody that binds to the CD137 protein.

In some embodiments, the light chain variable region of the antibody that binds to the CD137 protein and the heavy chain variable region of the antibody that binds to the CD137 protein in the first polypeptide chain constitute scFv.

In some embodiments, the first polypeptide chain further includes a human IgG constant region, and the human IgG constant region is located at a C-terminus of the heavy chain variable region of the antibody that binds to the PD-L1 protein and located at an N-terminus of the light chain variable region of the antibody that binds to the CD137 protein; alternatively, the human IgG constant region is located at the C-terminus of the heavy chain variable region of the antibody that binds to the PD-L1 protein and located at the N-terminus of the heavy chain variable region of the antibody that binds to the CD137 protein.

In some embodiments, the first polypeptide chain includes an amino acid sequence selected from the group consisting of SEQ ID NO: 30, SEQ ID NO: 43 and SEQ ID NO: 44. In some embodiments, the second polypeptide chain includes an amino acid sequence selected from the group consisting of SEQ ID NO: 15 and SEQ ID NO: 34.

In another aspect, the present application provides one or more nucleic acid molecules which encode the antibody, the antigen binding fragment or the variant thereof, or the bispecific antibody.

In another aspect, the present application provides a vector which includes the nucleic acid molecule.

In another aspect, the present application provides a cell which includes the nucleic acid molecule or the vector.

In another aspect, the present application provides a method of preparing the antibody, the antigen binding fragment of the variant thereof, or the bispecific antibody, including culturing the cells under conditions that allow the expression of the antibody, the antigen binding fragment or the variant thereof, or the bispecific antibody.

In another aspect, the present application provides a pharmaceutical composition which includes the antibody, the antigen binding fragment or the variant thereof, or the bispecific antibody, the nucleic acid molecule, the vector and/or the cell, and optionally a pharmaceutical acceptable adjuvant.

In another aspect, the present application provides use of the antibody, the antigen binding fragment or the variant thereof, or the bispecific antibody, the nucleic acid molecule, the vector, the cell and/or the pharmaceutical composition in manufacture of a drug for relieving or treating tumors.

In another aspect, the present application provides a method of inhibiting the binding of a PD-L1 protein to a PD-1 protein, including administering the antibody, the antigen binding fragment or the variant thereof, or the bispecific antibody, the nucleic acid molecule, the vector, the cell and/or the pharmaceutical composition.

In the present application, the CDR position of the antibody is determined in accordance with the antibody Kabat definition method.

Persons skilled in the art can easily recognize other aspects and advantages of the present disclosure from the detailed description below. The following detailed description only shows and describes exemplary embodiments of the present disclosure. For example, persons skilled in the art will recognize that the content of the present disclosure enables persons skilled in the art to make variations to the disclosed embodiments without departing from the spirit and scope of the invention to which the present application relates. Correspondingly, the accompanying drawings and the description in the specification of the present application are only exemplary, rather than restrictive.

BRIEF DESCRIPTION OF THE DRAWINGS

The specific features of the inventions involved in the present application are shown in the appended claims. By reference to the detailed exemplary embodiments and the accompanying drawings hereinafter, the features and the advantages of the inventions involved in the present application can be better understood. A brief description of the accompanying drawings is as follows:

FIG. 1 shows the amino acid sequence alignment between the PD-L1 antibody heavy chain variable regions (YN-002VH(SEQ ID NO: 2); YN-003VH(SEQ ID NO: 9)) and light chain variable regions (YN-002VL(SEQ ID NO: 4); YN-003VL(SEQ ID NO: 11)) of the present application and the related germline sequences(Germline IGHV 1-69(SEQ ID NO: 93); Germline IGLV 2-14(SEQ ID NO: 94)). The underlined are the CDRs determined in accordance with the Kabat definition method.

FIG. 2 shows the results of the PD-L1 antibody of the present application inhibiting the binding of the human PD-L1 to the human PD-1.

FIG. 5 shows the effect of various antibodies of the present application on the MC38 tumor growth in C57BL/6 mouse (*, P<0.05; ***, P<0.001; Unpaired (t-test).

FIG. 6 shows the amino acid sequence alignment between the CD137 antibody heavy chain variable regions (YN-005VH(SEQ ID NO: 18); YN-006VH(SEQ ID NO: 25)) and light chain variable regions (YN-005VL(SEQ ID NO: 20); YN-006VL(SEQ ID NO: 20)) of the present application and related germline sequences (Germline IGHV 3-23(SEQ ID NO: 95); Germline IGLV 1-44(SEQ ID NO: 96)), wherein the underlined are the CDRs determined in accordance with the Kabat definition method.

FIG. 8 shows the amino acid sequence alignment between the PD-L1 antibody heavy chain variable regions (YN-003VH(SEQ ID NO: 9)) and light chain variable regions (YN 003VL(SEQ ID NO: 11)) in the present application and related germline sequences Germline IGHV 1-69(SEQ ID NO: 93); Germline IGLV 2-14(SEQ ID NO: 94)), wherein the underlined are the CDRs determined in accordance with the Kabat definition method, and the shaded parts are the CDRs determined in accordance with the IMGT definition method. The amino acid residues in various CDR regions of YN-003 (including some amino acid residues in the CDR regions and several amino acid residues in the FR regions adjacent to the CDR regions) which are randomly targeted when performing affinity maturation are indicated in italics.

FIG. 21A, non-reduced; FIG. 21B reduced.

DETAILED DESCRIPTION OF THE EMBODIMENTS

Figure 3:
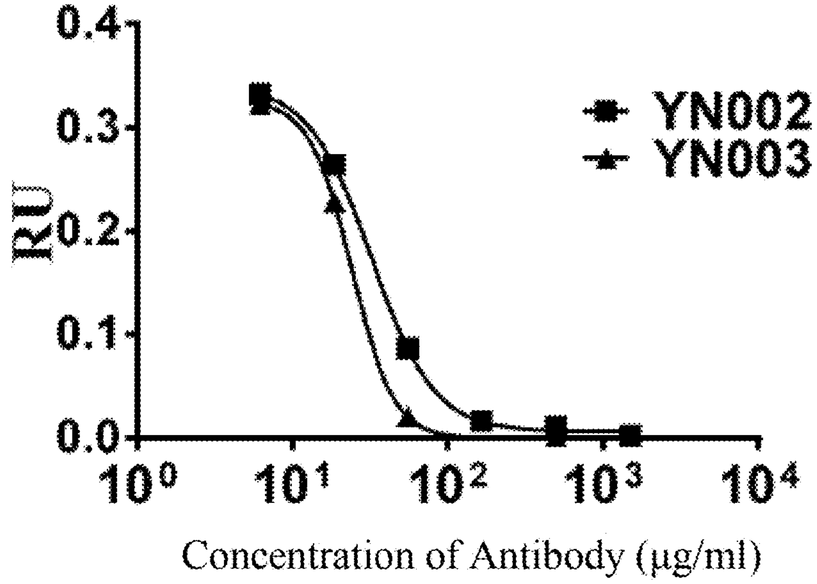
FIG. 3 shows the results of the PD-L1 antibody of the present application inhibiting the binding of Macaca fascicularis PD-L1 to the Macaca fascicularis PD-1.

Hereinafter the embodiments of the invention involved in the present application are illustrated by specific examples. Those of ordinary skills in the art can easily understand other advantages and effects of the invention disclosed in the present application from the disclosure of the description.

In the present application, the term "antibody" generally refers to a polypeptide molecule capable of specifically recognizing and/or neutralizing a specific antigen. For example, the antibody can include an immunoglobulin composed of at least two heavy (H) chains and two light (L) chains linked via a disulfide bond, and include any molecule including its antigen binding portion. The term "antibody" includes monoclonal antibodies, antibodies fragment or antibodies derivative, including but not limited to, human antibodies, humanized antibodies, chimeric antibodies, single-strand antibodies (e.g., scFv), and antigen-binding fragments of antibodies (e.g., Fab, Fab' and $(Fab)_2$ fragments). The term "antibody" further includes all the recombinants of an antibody, such as, antibodies expressed in prokaryotic cells, unglycosylated antibodies and any antigen-binding fragment of the antibody as described herein and their derivatives. Each heavy chain can be composed of a heavy chain variable region (VH) and a heavy chain constant region. Each light chain can be composed of light chain variable regions (VLs) and light chain constant regions. VH and VL regions can be further divided to highly variable regions called complementary determinant regions (CDR) which are dispersed in more conserved regions called framework regions (FR). Each VH and VL can be composed of three CDRs and four FRs which can be arranged from the amino terminal to the carboxy terminal in an order of FR1, CDR1, FR2, CDR2, FR3, CDR3 and FR4. The variable regions in the heavy chains and the light chains include binding domains that interact with an antigen. The constant region of the antibody can mediate the binding of the immunoglobulin to a host tissue or factor which includes various cells of immune systems (e.g., effector cells) and the first component of a classical complement system (Clq).

In the present application, the term "PD-L1 protein" generally refers to a ligand of programmed death-1 (PD-1) protein. PD-1 is a receptor of an Ig superfamily which interacts with the specific ligand (PD-L) to negatively regulate the signal transduction of T cells antigen receptor, and is recommended to play a role in maintenance of self tolerance. In the absence of the co-stimulatory signal, T cells are hard to feel the antigen stimulation, cannot produce an effective immune response, and can further cause the exhaustion or tolerance of heterologous antigen. PD-L1 may be expressed in either bematopoietic cells, or in a variety of non-hematopoietic cells. B7.1 (CD80) is also a PD-L1 receptor, which is expressed in activated B cells, T cells, macrophages and dendritic cells. As the ligand of PD-1 and B7.1, PD-L1 is further selectively expressed in a variety of tumor cells. Inhibition of the PD-L1 signal transduction includes blocking the interactions of PD-L1 with either or both of PD-1 and B7.1, thereby preventing PD-L1 from sending a negative co-stimulatory signal to T cells and other antigen-presenting cells. It may enhance the immune for infection (e.g., acute and chronic) response and tumor immune.

In the present application, the term "CD137 protein", also known as 4-1BB or TNFRS9, generally refers to a transmembrane protein of the tumor necrosis factor receptor superfamily (TNFRS), which is an activation-induced co-stimulatory molecule and an important regulator of immune responses. Studies have shown that CD137-activated monoclonal antibodies increase the expression of costimulatory molecules in many models, and significantly enhance the cytolytic T lymphocyte response and exert anti-tumor effects The anti-tumor effect of CD137-targeted therapy may be demonstrated by the anti-tumor efficacy study in mice by use of activated anti-mouse CD137 monoclonal antibody. CD137 has become a powerful activator of immune cells and an important candidate antigen for the treatment of various diseases. (See Vinay, Dass S., and Byoung S. Kwon. "4-1BB (CD137), an inducible costimulatory receptor, as a specific target for cancer therapy." BMB reports 47.3 (2014): 122.)

In the present application, the term "NFκB" refers to nuclear factor kappa-light-chain-enhancer of activated B cells (NFκB). This is a protein complex that controls DNA transcription. NFκB exists in almost all types of animal cells and participates in the cell's responses to many stimuli, including stress, cytokines, free radicals, UV radiation, oxidation of LDL, and microbial or viral antigens. In the immune response to infection, NFκB plays an important regulatory role (κ light chain is an important part of immunoglobulin). The abnormal regulation of NFκ B is associated with cancers, inflammations and autoimmune diseases, septic shocks, viral infections and abnormal immune development. NFκB is also closely associated with synaptic plasticity and memory processes. The main target cells of NFκB are chemokines, immune receptors, adhesion molecules, stress response genes, apoptosis regulators, transcription factors, growth factors, enzymes and cell cycle regulators. In addition, NFκB has an important influence on the transcription of several viral promoters/enhancers (e.g., HIV-1 and CMV) (see Tergaonkar, Vinay, "NFκB pathway: A good signaling paradigm and therapeutic target." The international journal of biochemistry & cell biology 38.10 (2006); 1647-1653.).

In the present application, the term "$K_D$" can be used interchangeably with "KD", and generally refers to the dissociation equilibrium constant of a specific antibody-antigen interaction with the unit of M (mol/L). KD may be calculated from the concentrations of substance AB and substances A and B obtained by dissociation of AB: KD=c(A)*c(B)/c(AB). It can be seen from this formula that the larger the KD value, the more the dissociation, and the weaker the affinity between the substances A and B; on the contrary, the smaller the KD value, the less the dissociation, and the stronger the affinity between the substances A and B.

In the present application, the term "monoclonal antibody" generally refers to a group of antibodies that are substantially homologous, that is, each antibody included in the group is the same except for possible naturally occurring mutations in trace amounts. Monoclonal antibodies are highly specific and are directed against a single antigenic site. In addition, in contrast to polyclonal antibody preparations that include different antibodies directed against different determinants (epitopes), each monoclonal antibody directed against a single determinant on the antigen is not interpreted as requiring any special method to produce antibodies. For example, the monoclonal antibodies may be prepared by hybridoma technology or produced in bacteria, eukaryotic animals or plant cells by recombinant DNA methods. Alternatively, the monoclonal antibodies may be also obtained from a phage antibody library, by using a technology as described in, e.g., Clackson et al., Nature, 352:624-628 (1991) and Marks et al., Mol. Biol., 222:581-597 (1991).

In the present application, the term "single chain antibody (scFv)" usually refers to a molecule formed by linking the variable region of the heavy chain of the antibody to the variable region of the light chain via a short peptide linker (linker).

In the present application, the term "chimeric antibody" generally refers to an antibody in which a portion of the amino acid sequence of each heavy or light chain is homologous to the corresponding amino acid sequence in an antibody from a specific species, or belongs to a specific class, and the rest of the chain is homologous to the corresponding sequence in another species. For example, the variable regions of both the light chain and the heavy chain are derived from the variable region of an antibody from one animal species (e.g., mouse, rat, etc.), while the constant part is homologous to an antibody sequence from another species (e.g., human). For example, for obtaining the chimeric antibodies, non-human B cells or hybridoma cells can be used to generate variable regions, and the constant regions combined therewith are derived from humans. The variable region bas an easy-to-prepare advantage, and its specificity is not affected by the source of the constant region combined therewith. At the same time, since the constant region of the chimeric antibody may be derived from humans, the possibility of the chimeric antibody inducing an immune response when injected is lower than that of an antibody of which the constant region is derived from a non-human origin.

In the present application, the term "humanized antibody" generally refers to an engineered antibody obtained by reducing the immunogenicity of the antibodies, immunoglobulin binding proteins and polypeptides derived from non-human species (e.g., mice or rats) to humans, while still retaining the antigen-binding properties of the original antibody. For example, it is feasible to use technical means including CDR grafting (Jones et al., Nature 321:522 (1986) and a variant thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co. et al., 1991 Proc Natl Acad Sci USA 88:2869-2873; Co. et al., 1992 J Immunol 148:1149-1154) and "veneering", (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312) or the like to humanize the non-human binding domain. If other regions, such as the hinge region and the constant region domains, are also derived from non-human sources, these regions can also be humanized.

In the present application, the term "fully human antibody" generally means that all parts of the antibody (including the constant regions, CH and CL regions of the antibody) are encoded by genes derived from human. The fully human antibody can significantly reduce the immune side effects caused by heterogeneous antibodies on the human body.

In the present application, the term "bispecific antibody (BsAbs)" generally refers to an antibody or antibody construct with dual specificity in its binding arm. Naturally occurring antibodies are monospecific and have the same specificity in their antigen binding arms. Bispecific antibodies are obtained from two different sources and constructed by recombinant DNA or cell fusion technology, so that they retain the two specificities of the original antibody. Bispecific antibodies carry two different antigen binding sites. The Fc part of a bispecific antibody is different from the Fc part of any parental monospecific antibody. Since the bispecific antibodies have dual specificity for both drugs and tumor cells, they may theoretically cause that the drug accumulation in tumors is higher than that in non-tumor sites in the body. Most of the bispecific new antibodies may redirect cytotoxic effector cells (e.g., Tc cells, NK cells, neutrophils) to the targeted cells (e.g., tumor cells). Bispecific antibodies can simultaneously block two different mediators/pathways that play a unique or overlapping role in pathogenesis, and may also increase the binding specificity by interacting with two, instead of one, different cell surface antigens. (Fanger, Michael W., and Paul M. Guyre, "Bispecific antibodies for targeted cellular cytotoxicity." Trends in biotechnology, 1991: 375-380), (Fan, Gaowei, et al. "Bispecific antibodies and their applications." Journal of hematology & oncology, 2015: 130)

In the present application, the term "sequence homology" generally means that the amino acid sequences of homologous proteins have a significant similarity.

In the present application, the term "epitope" usually refers to an antigenic determinant, that is, a part of a molecule that is recognized by the immune system (e.g., recognized by an antibody). For example, epitopes are discrete three-dimensional sites on an antigen recognized by the immune system. An epitope is usually composed of chemically active surface groups of molecules (e.g., amino acids or sugar side chains), and usually has specific three-dimensional structural characteristics and specific charge characteristics. Epitopes can be divided into conformational epitopes and non-conformational epitopes (linear epitopes) according to their structures. The difference between conformational epitopes and non-conformational epitopes is that the former will lose binding in the presence of denaturing solvents, while the latter does not. Epitopes that are only on the surface of antigenic substances and easily bind to the antigen recognition receptors or antibodies can be called functional epitopes; and epitopes that are located within the molecule and are not immunogenic can be called hidden epitopes. Epitopes may be composed of continuous residues, or formed by discontinuous residues that are close to each other due to the folding of the antigenic polymer. Epitopes formed by consecutive amino acids in proteins are usually maintained when exposed to denaturing solvents, but epitopes formed by discontinuous amino acids are usually lost after the exposure.

In the present application, the term "antigen-binding fragment" generally refers to a part of an intact antibody, e.g., the antigen-binding region and/or the variable region of the intact antibody. In some embodiments, the antigen-binding fragment may include Fab, Fab', $F(ab)_2$, $F(ab')_2$, and Fv fragments. In some embodiments, the antibodies of the present application may include double strand antibodies, linear antibodies, single-stand antibody molecules, and multispecific antibodies formed from antibody fragments. The two identical antigen-binding fragments obtained by digesting an antibody having an intact structure with papain (e.g., by removing the Fc region and the hinge region) are called "Fab" fragments. The Fab fragment is composed of an intact light chain, a variable region of the heavy chain (VH) and a first constant domain (CHI) of the heavy chain. Each Fab fragment is monovalent with respect to the antigen binding, that is, it has a single antigen binding site. $F(ab)_2$ antibody fragments were initially produced as pairs of Fab fragments linked via a cysteine. The single and large $F(ab')_2$ fragment obtained by digesting an antibody having an intact structure with pepsin is roughly equal to two Fab fragments linked via disulfide and having different antigen binding activities, and is still capable of cross-linking the antigen. Fab' fragments differ from Fab fragments in that they have several additional residues at the carboxy terminus of the CH1 domain, including one or more cysteines from the hinge region of an antibody. The Fv fragment is composed of the VL and VH domains of one arm of the antibody.

In the present application, the term "variant" generally refers to an amino acid sequence that has substantially the same function (e.g., a capacity of specifically binding to the PD-L1) and at least 85% (e.g., at least 85%, at least 90%, at least 91%, at least 92%, at least 93%, at least 94%, at least 95%, at least 96%, at least 97%, at least 98%, at least 99%, or at least 100%) sequence identity. In some embodiments, the variant of an amino acid sequence is an amino acid sequence that has substantially the same function (e.g., capable of specifically binding to PD-L1), and includes one or more (e.g., 1-2, 1-3, 1-4, 1-5, 1-6, 1-7, 1-8, 1-9, 1-10 or more) amino acid substitutions, deletion, or additions.

In the present application, the term "identity" generally refers to the percent of the number of the same amino acid residues in the number of all the amino acid residues when comparing the candidate sequence with the specific peptide or polypeptide sequence.

In the present application, the term "IgG" generally refers to an immunoglobulin G. IgG is one of the human immunoglobulins, and others include IgA, Ig M, IgD and IgE. IgG is the main antibody component of serum, accounting for about 75% of serum Ig. According to the antigenity difference in the γ chain of the IgG molecule, the human IgG has four subtypes: IgG1, IgG2, IgG3, and IgG4. IgG plays an important role in immunity. In the present application, the term "IgG1" generally refers to the subtype with the highest proportion of IgG, which has a higher affinity for Fc receptors.

In the present application, the term "nucleic acid molecule" generally refers to an isolated form of nucleotides, deoxyribonucleotides or ribonucleotides or their analogs of any length isolated from their natural environment or artificially synthesized.

In the present application, the term "vector" generally refers to a nucleic acid molecule capable of self-replication in a suitable host, which transfers the inserted nucleic acid molecule into the host cells and/or between the host cells. The vector may include a vector mainly used for inserting DNA or RNA into cells, a vector mainly used for replicating DNA or RNA, and a vector mainly used for expression of the transcription and/or translation of DNA or RNA. The vector also includes a vector having multiple functions described above. The vector can be a polynucleotide that can be transcribed and translated into a polypeptide when introduced into a suitable host cell. Generally, by culturing a suitable host cell containing the vector, the vector may produce the desired expression product.

In the present application, the term "host cell" generally refers to plasmid or vector which can include or has included the nucleic acid molecule of the present application, or individual cell, cell line or cell culture which can express the antibody or the antigen-binding fragment thereof of the present application. The host cell may include the progeny of a single host cell. Due to natural, accidental and deliberate mutations, the progeny cells cannot be exactly the same as the original parental cells in morphology or genome, as long as they can express the antibody or the antigen-binding fragment thereof of the present application. The host cell may be obtained by transfecting cells in vitro by use of the vector of the present application. The host cell may be prokaryotic cells (e.g., *E. Coli*), and can also be eukaryotic cells (e.g., yeast cells, such as, COS cells, Chinese hamster ovary (CHO) cells, Hela cells, HEK293 cells, COS-1 cells, NS0 cells or myeloma cells). In some embodiments, the host cell is a mammalian cell. For example, the mammalian cell may be CHO-K1 cell. In the present application, the term "recombinant host cell" usually refers to a cell to which a recombinant expression vector is introduced. The recombinant host cell not only includes a specific cell, but also includes the progeny of such cells.

In the present application, the term "cancer" generally refers to or describes a physiological status of mammal which is typically characterized in disorders of cell proliferation or survival. Examples of cancers include, but are not limited to, cancer, lymphoma, maternal cell tumor, sarcoma and leukemia and lymphoid malignant tumor. For example, it may be lymphoma.

In the present application, the term "between" generally means that the C-terminus of a certain amino acid fragment is directly or indirectly linked to the N-terminus of the first amino acid fragment, and the N-terminus thereof is directly or indirectly linked to the C-terminus of the second amino acid fragment. In the light chain, for example, the N-terminus of the L-FR2 is directly or indirectly linked to the C-terminus of the LCDR1, and the C-terminus of the L-FR2 is directly or indirectly linked to the N-terminus of the LCDR2. For another example, the N-terminus of the L-FR3 is directly or indirectly linked to the C-terminus of the LCDR2, and the C-terminus of the L-FR3 is directly or indirectly linked to the N-terminus of the LCDR3. In the heavy chain, for example, the N-terminus of the H-FR2 is directly or indirectly linked to the C-terminus of the HCDR1, and the C-terminus of the H-FR2 is directly or indirectly linked to the N-terminus of the HCDR2. For another example, the N-terminus of the H-FR3 is directly or indirectly linked to the C-terminus of the HCDR2, and the C-terminus of the H-FR3 is directly or indirectly linked to the N-terminus of the HCDR3.

In the present application, the term "about" generally refers to a variation in a range of the given value ±0.5%-±10%, such as, a variation in a range of the given value ±0.5%, ±1%, ±1.5%, ±2%, ±2.5%, ±3%, ±3.5%, ±4%, ±4.5%, ±5%, ±5.5%, ±6%, ±6.5%, ±7%, ±7.5%, ±8%, ±8.5%, ±9%, ±9.5%, or ±10%.

In the present application, the term "includes" generally refers to the meaning of include, sum up, have or contain. In some instances, it is also expressed as a meaning of "be" or "consist of".

Antibody or Antibody Binding Fragment Thereof

In one aspect, the present application provides an antibody or an antigen binding fragment or a variant thereof which binds to a PD-L1 protein with a $K_D$ value of $3\times10^{-9}$ M or less (e.g., the $K_D$ value is not higher than about $3\times10^{-9}$ M, not higher than about $2\times10^{-9}$ M, not higher than about $1\times10^{-9}$ M, not higher than about $9\times10^{-10}$ M, not higher than about $8\times10^{-10}$ M, not higher than about $7\times10^{-10}$ M, not higher than about $6\times10^{-10}$ M, not higher than about $5\times10^{-10}$ M, not higher than about $4\times10^{-10}$ M, not higher than about $3\times10^{-10}$ M, not higher than about $2\times10^{-10}$ M, not higher than $1\times10^{-10}$ M, not higher than about $9\times10^{-11}$ M, not higher than about $8\times10^{-11}$ M, not higher than about $7\times10^{-11}$ M, not higher than about $6\times10^{-11}$ M, not higher than about $1\times10^{-11}$ M or less). For example, the antibody, the antigen binding fragment or the variant thereof may bind to a PD-L1 protein with a $K_D$ value lower than $8\times10^{-11}$ M.

The antibody or the antigen binding fragment or the variant thereof of the present application may inhibit the binding of PD-L1 to PD-1.

The antibody or the antigen binding fragment or the variant thereof of the present application may relieve or treat tumor-associated diseases. The tumor includes colon cancer.

In the present application, the antibody may be selected from the group consisting of monoclonal antibody, single-strand antibody, chimeric antibody, humanized antibody and fully human antibody.

In the present application, the antigen-binding fragment may be selected from the group consisting of Fab, Fab', $F(ab)_2$ and Fv fragment.

In the present application, the variant may be an amino acid sequence which has substantially the same functions (e.g., can specifically bind to PD-L1) thereto, and has at least 85% or more (e.g., at least about 85%, about 90%, about 91%, about 92%, about 93%, about 94%, about 95%, about 96%, about 97%, about 98%, about 99% or more) of sequence identity. In some embodiments, the variant of the amino acid sequence has basically the same function (e.g., capable of specifically binding to PD-L1), and includes an amino acid sequence obtained by the addition, deletion or substitute of one or more (e.g., 1-2, 1-3, 1-4, 1-5, 1-6, 1-7, 1-8, 1-9, 1-10 or more) amino acids. For another example, the variant of the present application may be selected from the following group: a protein or polypeptide which undergoes substitution, deletion or addition of one or more amino acids in the antibody or the fragment for antigen-binding thereof; and a protein or polypeptide which has more than 85(e.g., at least about 85%, about 90%, about 91%, about 92%, about 93%, about 94%, about 95%, about 96%, about 97%, about 98%, about 99% or more) sequence identity to the antibody or the fragment for antigen-binding thereof.

In some embodiments, the antibody of the present application may include an antibody light chain or a fragment thereof which includes a LCDR1, and the LCDR1 includes an amino acid sequence shown in SEQ ID NO: 53: $TGTX_1SX_2VGGYX_3X_4VS$; wherein $X_1$ is S, R or V; $X_2$ is D, E or S; $X_3$ is N or R; $X_4$ is Y or E, and wherein the LCDR1 is determined according to the index of the antibody Kabat number. For example, the antibody light chain or the fragment thereof may include LCDR1, and the LCDR1 includes the following amino acid sequence or a variant thereof; SEQ ID NO: 54-58.

In some embodiments, the antibody light chain or the fragment thereof may include LCDR2 including an amino acid sequence shown in SEQ ID NO: 59: $X_1NSX_2RPS$, wherein $X_1$ is G or E; $X_2$ is N or I, and wherein the LCDR2 is determined according to the index of the antibody Kabat number. For example, the antibody light chain or the fragment thereof can include LCDR2 including the following amino acid sequence of a variant thereof; SEQ ID NO: 60-61.

In some embodiments, the antibody light chain or the fragment thereof may include LCDR3 including an amino acid sequence shown in SEQ ID NO: 62; $QSYDSSLSGX_1V$, wherein $X_1$ is S or T, and wherein the LCDR3 is determined according to the index of the antibody Kabat number. For example, the antibody light chain or the fragment thereof may include LCDR3 including an amino acid sequence or a variant thereof selected from the group consisting of SEQ ID NO: 63 and SEQ ID NO: 64.

In some embodiments, the antibody light chain or the fragment thereof may further include framework regions L-FR1, L-FR2, L-FR3, and L-FR4. For example, the C-terminus of the L-FR1 can be directly or indirectly linked to the N-terminus of the LCDR1, and the L-FR1 includes an amino acid sequence shown in SEQ ID NO: 71. The L-FR2 is located between the LCDR1 and the LCDR2, and the L-FR2 includes an amino acid sequence shown in SEQ ID NO: 72. The L-FR3 is located between the LCDR2 and the LCDR3, and the L-FR3 includes an amino acid sequence shown in SEQ ID NO: 73-75, The N-terminus of the L-FR4 is directly or indirectly linked to the C-terminus of the LCDR3, and the L-FR4 includes an amino acid sequence shown in SEQ ID NO: 76. In some embodiments, the framework regions are selected from the group consisting of human consensus framework sequences and human germline sequences.

In some embodiments, the light chain or the fragment thereof of the antibody of the present application includes a light chain variable region VL, and the light chain variable region VL includes an amino acid sequence or a variant thereof selected from the group consisting of SEQ ID NO: 4. SEQ ID NO: 11, SEQ ID NO: 33, SEQ ID NO: 37, SEQ ID NO: 39 and SEQ ID NO: 41.

In the antibody or the antigen binding fragment or the variant thereof of the present application, the antibody light chain or a fragment thereof can further include a human constant region, and the human constant region includes a human Igλ constant region.

In the present application, the antibody light chain or the fragment thereof may include an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

In the present application, the antibody of the present application can include an antibody heavy chain or a fragment thereof, wherein the antibody heavy chain or the fragment thereof may include HCDR1, and the HCDR1 can include an amino acid sequence selected from the group consisting of those shown in SEQ ID NO: 45: $X_1YAIS$, wherein $X_1$ is S or T, and wherein the HCDR1 is determined according to the index of the antibody Kabat number. For example, the antibody heavy chain or the fragment thereof may include HCDR1, and the HCDR1 includes an amino acid sequence or a variant thereof selected from the group consisting of SEQ ID NO: 46 and SEQ ID NO: 47.

In the present application, the antibody heavy chain or the fragment thereof may include HCDR2, and the HCDR2 includes the following amino acid sequence or a variant thereof; SEQ ID NO: 48, and wherein the HCDR2 is determined according to the index of the antibody Kabat number.

In the present application, the antibody heavy chain or the fragment thereof may include HCDR3, and the HCDR3 includes an amino acid sequence selected from the group consisting of those shown in SEQ ID NO: 49: $TMX_1X_2YX_3X_4GNX_5DY$, wherein $X_1$ is D, E or G, $X_2$ is G or E, $X_3$ is S or G, $X_4$ is Y or F, $X_5$ is F or Y, and wherein the HCDR3 is determined according to the index of the antibody Kabat number. For example, the antibody heavy chain or the fragment thereof may include HCDR3, and the HCDR3 includes the following amino acid sequence or a variant thereof; SEQ ID NO: 50-52.

In some embodiments, the antibody heavy chain or the fragment thereof further includes framework regions H-FR1, H-FR2, H-FR3, and H-FR4. For example, the C-terminus of H-FR1 is directly or indirectly linked to the N-terminus of HCDR1, and the H-FR1 may include an amino acid sequence selected from the group consisting of SEQ ID NO: 65, SEQ ID NO: 66 and SEQ ID NO: 67. The H-FR2 is located between the HCDR1 and the HCDR2, and the H-FR2 can include an amino acid sequence shown in SEQ ID NO: 68. The H-FR3 is located between the HCDR2 and the HCDR3, and the H-FR3 may include an amino acid sequence shown in SEQ ID NO: 69. The N-terminus of H-FR4 is directly or indirectly linked to the C-terminus of HCDR3, and the H-FR4 may include an amino acid sequence shown in SEQ ID NO: 70. In some embodiments, the framework regions are selected from the group consisting of human consensus framework sequences and human germline sequences.

The antibody heavy chain or the fragment thereof of the present application can include a heavy chain variable region VH, and the heavy chain variable region VH can include an amino acid sequence or a variant thereof selected from the group consisting of SEQ ID NO: 2, SEQ ID NO: 9, SEQ ID NO: 31, and SEQ ID NO: 35. In the antibody, the antigen binding fragment or the variant thereof of the present application, the antibody heavy chain or a fragment thereof may further include a human constant region. For example, the human constant region may include a human IgG constant region. For example, the human IgG constant region may include a human IgG1 constant region.

In some embodiments, the antibody heavy chain or a fragment thereof may include an amino acid sequence or a variant thereof selected from the group consisting of SEQ ID NO: 6, SEQ ID NO: 13, SEQ ID NO: 32, and SEQ ID NO: 36.

In some embodiments, the antibody of the present application includes an antibody light chain or a fragment thereof which includes LCDR1, and the LCDR1 includes an amino acid sequence shown in SEQ ID NO: 53: TGTX$_1$SX$_2$VGGYX$_3$X$_4$VS; wherein X$_1$ is S, R or V; X$_2$ is D, E or S; X$_3$ is N or R; X$_4$ is Y or E, and wherein the LCDR1 is determined according to the index of the antibody Kabat number. For example, the antibody light chain or the fragment thereof may include LCDR1, and the LCDR1 includes an amino acid sequence or a variant thereof selected from the group consisting of SEQ ID NO: 54-58. The antibody light chain or the fragment thereof includes LCDR2 including an amino acid sequence shown in SEQ ID NO: 59: X$_1$NSX$_2$RPS, wherein X$_1$ is G or E; X$_2$ is N or I, and wherein the LCDR2 is determined according to the index of the antibody Kabat number. For example, the antibody light chain or the fragment thereof can include LCDR2 including an amino acid sequence or a variant thereof selected from the group consisting of SEQ ID NO: 60-61. The antibody light chain or the fragment thereof includes LCDR3 including an amino acid sequence shown in SEQ ID NO: 62: QSYDSSLSGX$_1$V, wherein X$_1$ is S or T, and wherein the LCDR3 is determined according to the index of the antibody Kabat number. For example, the antibody light chain or the fragment thereof may include LCDR3 including an amino acid sequence or a variant thereof selected from the group consisting of SEQ ID NO: 63-64. Moreover, the antibody of the present application includes an antibody heavy chain or a fragment thereof which includes a HCDR1, and the HCDR1 includes an amino acid sequence selected from the group consisting of those shown in SEQ ID NO: 45: X$_1$YAIS, wherein X$_1$ is S or T, and wherein the HCDR1 is determined according to the index of the antibody Kabat number. For example, the antibody heavy chain of the fragment thereof may include HCDR1, and the HCDR1 includes an amino acid sequence or a variant thereof selected from the group consisting of SEQ ID NO: 46 and SEQ ID NO: 47. For example, the antibody heavy chain or the fragment thereof may include HCDR2, and the HCDR2 includes the following amino acid sequence or a variant thereof; SEQ ID NO: 48, and wherein the HCDR2 is determined according to the index of the antibody Kabat number. For another example, the antibody heavy chain or the fragment thereof includes HCDR3, and the HCDR3 includes an amino acid sequence selected from that shown in SEQ ID NO: 49: TMX$_1$X$_2$YX$_3$X$_4$GNX$_5$DY, wherein X$_1$ is D, E or G, X$_2$ is G or E, X$_3$ is S or G, X$_4$ is Y or F, X$_5$ is F or Y, and wherein the HCDR3 is determined according to the index of the antibody Kabat number. The antibody heavy chain or the fragment thereof may include HCDR3, and the HCDR3 includes the following amino acid sequence or a variant thereof; SEQ ID NO: 50-52.

The amino acid sequence of the LCDR1 of the antibody, the antigen binding fragment or the variant thereof of the present application may include SEQ ID NO: 54 of a variant thereof, the amino acid sequence of the LCDR2 may include SEQ ID NO: 60 or a variant thereof; the amino acid sequence of the LCDR3 may include SEQ ID NO: 63 or a variant thereof; and the amino acid sequence of the HCDR1 may include SEQ ID NO: 46; the amino acid sequence of the HCDR2 may include SEQ ID NO: 48 of a variant thereof; the amino acid sequence of the HCDR3 may include SEQ ID NO: 50 or a variant thereof. For example, the antibody, the antigen binding fragment or the variant thereof may include the antibody YN-002 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 73 or a variant thereof, the amino acid sequence of the L-FR4 may include SEQ ID NO: 76 or a variant thereof; and the amino acid sequence of the H-FR1 may include SEQ ID NO: 65 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include an antibody having the same LCDR1-3, HCDR1-3, L-FR 1-4 and H-FR1-4 as the antibody YN-002. In some embodiments, the light chain of the antibody, the antigen binding fragment or the variant thereof of the present application may include a light chain variable region, the amino acid sequence of the light chain variable region may include SEQ ID NO: 4 or a variant thereof; and wherein the heavy chain may include a heavy chain variable region, and the amino acid sequence of the heavy chain variable region may include SEQ ID NO: 2 or a variant thereof. For example, the antibody, the antigen binding fragment or the variant thereof may include the antibody YN-002 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 8 and the amino acid sequence of the heavy chain is shown in SEQ ID NO: 6. For example, the antibody, the antigen binding fragment or the variant thereof may include the antibody YN-002 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 54 or a variant thereof; the amino acid sequence of the LCDR2 may include SEQ ID NO: 60 or a variant thereof; the amino acid sequence of the LCDR3 may include SEQ ID NO: 63 or a variant thereof; and the amino acid sequence of the HCDR1 may include SEQ ID NO: 46 or a variant thereof the amino acid sequence of the HCDR2 may include SEQ ID NO: 48 or a variant thereof; the amino acid sequence of the HCDR3 may include SEQ ID NO: 50 or a variant thereof. In some embodiments, the reference antibody can include the antibody YN-002 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof, the amino acid sequence of the L-FR2 may include SEQ ID NO: 72 or a variant thereof; the amino acid sequence of the L-FR3 may include SEQ ID NO: 73 or a variant thereof; the amino acid sequence of the L-FR4 may include SEQ ID NO: 76 or a variant thereof; and the amino acid sequence of the H-FR1 may include SEQ ID NO: 65 or a variant thereof; the amino acid sequence of the H-FR2 may include SEQ ID NO: 68 or a variant thereof; the amino acid sequence of the H-FR3 may include SEQ ID NO: 69 or a variant thereof; the amino acid sequence of the H-FR4 may include SEQ ID NO: 70 or a variant thereof. For example, the antibody or the antigen-binding fragment thereof may include the antibody YN-002 or an antibody with the same LCDR1-3, HCDR1-3, L-FR1-4 and H-FR1-4 therewith. In some embodiments, the reference antibody can include a light chain variable region and a heavy chain variable region, the amino acid sequence of the light chain variable region may include SEQ ID NO: 4 or a variant thereof; and the amino acid sequence of the heavy chain variable region may include SEQ ID NO: 2 or a variant thereof. For example, the reference antibody may include the antibody YN-002 or an antibody having the same light chain variable region and heavy chain variable region therewith. In some embodiments, the reference antibody may include a light chain and a heavy chain, the amino acid sequence of the light chain may be shown in SEQ ID NO: 8, and the heavy chain amino acid sequence may be shown in SEQ ID NO: 6. For example, the reference antibody may include the antibody YN-002 or have the same light chain and heavy chain therewith.

In some embodiments, the amino acid sequence of the LCDR1 of the antibody, the antigen binding fragment or the variant thereof of the present application may include SEQ ID NO: 54 or a variant thereof; the amino acid sequence of the LCDR2 may include SEQ ID NO: 60 or a variant thereof the amino acid sequence of the LCDR3 may include SEQ ID NO: 63 or a variant thereof; and the amino acid sequence of the HCDR1 may include SEQ ID NO: 46 or a variant thereof; the amino acid sequence of the HCDR2 can include SEQ ID NO: 48 or a variant thereof; the amino acid sequence of the HCDR3 may include SEQ ID NO: 50 or a variant thereof. For example, the antibody, the antigen binding fragment or the variant thereof can include the antibody YN-003 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 66 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include the antibody YN-003 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 11 or a variant thereof; and wherein the heavy chain may include a heavy chain variable region, and the amino acid sequence of the heavy chain variable region can include SEQ ID NO: 9 or a variant thereof. For example, the antibody, the antigen binding fragment or the variant thereof may include the antibody YN-003 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 15 and the amino acid sequence of the heavy chain is shown in SEQ ID NO: 13. For example, the antibody, the antigen binding fragment or the variant thereof may include the antibody YN-003 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody can include LCDR1-3 and HCDR1-3, and the amino acid sequence of the LCDR1 may include SEQ ID NO: 54 or a variant thereof; the amino acid sequence of the LCDR2 may include SEQ ID NO: 60 or a variant thereof; the amino acid sequence of the LCDR3 may include SEQ ID NO: 63 or a variant thereof; and the amino acid sequence of the HCDR1 may include SEQ ID NO: 46 or a variant thereof; the amino acid sequence of the HCDR2 may include SEQ ID NO: 48 or a variant thereof; the amino acid sequence of the HCDR3 may include SEQ ID NO: 50 or a variant thereof. In some embodiments, the reference antibody can include the antibody YN-003 or an antibody with the same LCDR1-3 and HCDR1-3 therewith. In some embodiments, the reference antibody includes L-FR1-4 and H-FR1-4, and the amino acid sequence of the L-FR1 may include SEQ ID NO. 71 or a variant thereof; the amino acid sequence of the L-FR2 may include SEQ ID NO: 72 or a variant thereof the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 66 or a variant thereof, the amino acid sequence of the H-FR2 may include SEQ ID NO: 68 or a variant thereof; the amino acid sequence of the H-FR3 may include SEQ ID NO: 69 or a variant thereof; the amino acid sequence of the H-FR4 may include SEQ ID NO: 70 or a variant thereof. For example, the antibody or the antigen-binding fragment thereof may include the antibody YN-003 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 11 or a variant thereof; and the amino acid sequence of the heavy chain variable region may include SEQ ID NO: 9 or a variant thereof. For example, the reference antibody may include the antibody YN-003 or an antibody having the same light chain variable region and heavy chain variable region therewith. In some embodiments, the reference antibody may include a light chain and a heavy chain, the amino acid sequence of the light chain may be shown in SEQ ID NO: 15 and the heavy chain amino acid sequence may be shown in SEQ ID NO: 13. For example, the reference antibody may include the antibody YN-003 or have the same light chain and heavy chain therewith.

In some embodiments, the amino acid sequence of the LCDR1 of the antibody, the antigen binding fragment or the variant thereof of the present application may include SEQ ID NO: 55 or a variant thereof; the amino acid sequence of the LCDR2 may include SEQ ID NO: 60 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; the amino acid sequence of the HCDR3 may include SEQ ID NO: 51 or a variant thereof. For example, the antibody, the antigen binding fragment or the variant thereof may include the antibody YN-035 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include the antibody YN-035 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 33 or a variant thereof; and wherein the heavy chain may include a heavy chain variable region, and the amino acid sequence of the heavy chain variable region may include SEQ ID NO: 31 or a variant thereof. For example, the antibody, the antigen binding fragment or the variant thereof may include the antibody YN-035 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 34 and the amino acid sequence of the heavy chain is shown in SEQ ID NO: 32. For example, the antibody, the antigen binding fragment or the variant thereof may include the antibody YN-035 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 55 or a variant thereof; the amino acid sequence of the LCDR2 may include SEQ ID NO: 60 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; the amino acid sequence of the HCDR3 may include SEQ ID NO: 51 or a variant thereof. In some embodiments, the reference antibody may include the antibody YN-035 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof; the amino acid sequence of the L-FR2 may include SEQ ID NO: 72 or a variant thereof, the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; the amino acid sequence of the H-FR4 may include SEQ ID NO: 70 or a variant thereof. For example, the antibody or the antigen-binding fragment thereof may include the antibody YN-035 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 33 or a variant thereof; and the amino acid sequence of the heavy chain variable region may include SEQ ID NO: 31 or a variant thereof. For example, the reference antibody may include the antibody YN-035 or an antibody having the same light chain variable region and heavy chain variable region therewith. In some embodiments, the reference antibody can include a light chain and a heavy chain, the amino acid sequence of the light chain may be shown in SEQ ID NO: 34 and the heavy chain amino acid sequence may be shown in SEQ ID NO: 32. For example, the reference antibody may include the antibody YN-035 or have the same light chain and heavy chain therewith.

In some embodiments, the amino acid sequence of the LCDR1 of the antibody, the antigen binding fragment or the variant thereof of the present application may include SEQ ID NO: 55 or a variant thereof; the amino acid sequence of the LCDR2 may include SEQ ID NO: 60 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; the amino acid sequence of the HCDR3 may include SEQ ID NO: 52 or a variant thereof. For example, the antibody, the antigen binding fragment or the variant thereof may include the antibody YN-036 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include the antibody YN-036 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 33 or a variant thereof; and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-036 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 34 and the amino acid sequence of the heavy chain is shown in SEQ ID NO: 36. For example, the antibody, the antigen binding fragment or the variant thereof may include the antibody YN-036 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 55 or a variant thereof; the amino acid sequence of the LCDR2 may include SEQ ID NO: 60 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. In some embodiments, the reference antibody may include the antibody YN-036 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof; the amino acid sequence of the L-FR2 may include SEQ ID NO: 72 or a variant thereof; the amino acid sequence of the L-FR3 may include SEQ ID NO: 74 or a variant thereof; the amino acid sequence of the L-FR4 may include SEQ ID NO: 76 or a variant thereof; and the amino acid sequence of the H-FR1 may include SEQ ID NO: 67 or a variant thereof, the amino acid sequence of the H-FR2 may include SEQ ID NO: 68 or a variant thereof, the amino acid sequence of the H-FR3 may include SEQ ID NO: 69 or a variant thereof; the amino acid sequence of the H-FR4 may include SEQ ID NO: 70 or a variant thereof. For example, the antibody or the antigen-binding fragment thereof may include the antibody YN-036 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 33 or a variant thereof; and the amino acid sequence of the heavy chain variable region may include SEQ ID NO: 35 or a variant thereof. For example, the reference antibody may include the antibody YN-036 or an antibody having the same light chain variable region and heavy chain variable region therewith. In some embodiments, the reference antibody may include a light chain and a heavy chain, the amino acid sequence of the light chain may be shown in SEQ ID NO: 34 and the heavy chain amino acid sequence may be shown in SEQ ID NO: 36. For example, the reference antibody may include the antibody YN-036 or have the same light chain and heavy chain therewith.

In some embodiments, the amino acid sequence of the LCDR1 of the antibody, the antigen binding fragment or the variant thereof of the present application may include SEQ ID NO: 56 or a variant thereof; the amino acid sequence of the LCDR2 may include SEQ ID NO: 61 or a variant thereof, the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. For example, the antibody, the antigen binding fragment or the variant thereof may include the antibody YN-037 or an antibody with the same LCDR 1-3 and HCDR1-3 therewith. In some cases, the amino acid sequence of the L-FR1 of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include the antibody YN-037 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 37 or a variant thereof; and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-037 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 38 and the amino acid sequence of the heavy chain is shown in SEQ ID NO: 36. For example, the antibody, the antigen binding fragment or the variant thereof may include the antibody YN-037 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 56 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof, and the amino acid sequence of the HCDR3 may include SEQ ID NO: 52 or a variant thereof. In some embodiments, the reference antibody can include the antibody YN-037 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof, the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody or the antigen-binding fragment thereof may include the antibody YN-037 or an antibody with the same LCDR1-3, HCDR1-3, L-FR1-4 and H-FR1-4 therewith.

In some embodiments, the reference antibody may include a light chain variable region and a heavy chain variable region, the amino acid sequence of the light chain variable region may include SEQ ID NO: 37 or a variant thereof; and the amino acid sequence of the heavy chain variable region may include SEQ ID NO: 35 or a variant thereof. For example, the reference antibody may include the antibody YN-037 or an antibody having the same light chain variable region and heavy chain variable region therewith. In some embodiments, the reference antibody may include a light chain and a heavy chain, the amino acid sequence of the light chain may be shown in SEQ ID NO: 38 and the heavy chain amino acid sequence may be shown in SEQ ID NO: 36. For example, the reference antibody may include the antibody YN-037 or have the same light chain and heavy chain therewith.

In some embodiments, the amino acid sequence of the LCDR1 of the antibody, the antigen binding fragment or the variant thereof of the present application may include SEQ ID NO: 57 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. For example, the antibody, the antigen binding fragment or the variant thereof can include the antibody YN-038 or an antibody with the same LCDR1-3 and HCDR1-3 therewith. In some cases, the amino acid sequence of the L-FR1 of the antibody, the antigen binding fragment or the variant thereof may include SEQ ID NO: 71 or a variant thereof the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof can include the antibody YN-038 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 39 or a variant thereof; and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-038 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 40 and the amino acid sequence of the heavy chain is shown in SEQ ID NO: 36. For example, the antibody, the antigen binding fragment or the variant thereof may include the antibody YN-038 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 57 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. In some embodiments, the reference antibody can include the antibody YN-038 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO:

69 or a variant thereof; and the amino acid sequence of the H-FR4 may include SEQ ID NO: 70 or a variant thereof. For example, the antibody or the antigen binding fragment thereof can include the antibody YN-038 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 39 or a variant thereof; and the amino acid sequence of the heavy chain variable region may include SEQ ID NO: 35 or a variant thereof. For example, the reference antibody can include the antibody YN-038 or an antibody having the same light chain variable region and heavy chain variable region therewith. In some embodiments, the reference antibody may include a light chain and a heavy chain, the amino acid sequence of the light chain may be shown in SEQ ID NO: 40 and the heavy chain amino acid sequence may be shown in SEQ ID NO: 36. For example, the reference antibody can include the antibody YN-038 or have the same light chain and heavy chain therewith.

In some embodiments, the amino acid sequence of the LCDR1 of the antibody, the antigen binding fragment or the variant thereof of the present application may include SEQ ID NO: 58 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. For example, the antibody, the antigen binding fragment or the variant thereof may include the antibody YN-039 or an antibody with the same LCDR 1-3 and HCDR1-3 therewith. In some cases, the amino acid sequence of the L-FR1 of the antibody, the antigen binding fragment or the variant thereof may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody, the antigen binding fragment or the variant thereof may include the antibody YN-039 or an antibody with the same LCDR1-3, HCDR1-3, L-FR1-4 and H-FR1-4 therewith. In some embodiments, the light chain of the antibody, the antigen binding fragment or the variant thereof of the present application may include a light chain variable region, the amino acid sequence of the light chain variable region may include SEQ ID NO: 41 or a variant thereof; and wherein the heavy chain may include a heavy chain variable region, and the amino acid sequence of the heavy chain variable region may include SEQ ID NO: 35 or a variant thereof. For example, the antibody, the antigen binding fragment or the variant thereof may include the antibody YN-039 or an antibody having the same light chain variable region and heavy chain variable region therewith. In some embodiments, the antibody, the antigen binding fragment or the variant thereof of the present application may include a light chain and a heavy chain, the amino acid sequence of the light chain is shown in SEQ ID NO: 42 and the amino acid sequence of the heavy chain is shown in SEQ ID NO: 36. For example, the antibody, the antigen binding fragment or the variant thereof may include the antibody YN-039 or have the same light chain and heavy chain therewith.

In some embodiments, the antibody, the antigen binding fragment or the variant thereof of the present application competes with a reference antibody to bind to PD-L1 protein (e.g., human PD-L1 protein). The reference antibody may include LCDR1-3 and HCDR1-3, and the amino acid sequence of the LCDR1 may include SEQ ID NO: 58 or a variant thereof; the amino acid sequence of the LCDR2 may include SEQ ID NO: 61 or a variant thereof; the amino acid sequence of the LCDR3 may include SEQ ID NO: 64 or a variant thereof; and the amino acid sequence of the HCDR1 may include SEQ ID NO: 47 or a variant thereof; the amino acid sequence of the HCDR2 may include SEQ ID NO: 48 or a variant thereof; and the amino acid sequence of the HCDR3 may include SEQ ID NO: 52 or a variant thereof. In some embodiments, the reference antibody may include the antibody YN-039 or an antibody with the same LCDR1-3 and HCDR1-3 therewith. In some embodiments, the reference antibody includes L-FR1-4 and H-FR1-4, and the amino acid sequence of the L-FR1 may include SEQ ID NO: 71 or a variant thereof; the amino acid sequence of the L-FR2 may include SEQ ID NO: 72 or a variant thereof; the amino acid sequence of the L-FR3 may include SEQ ID NO: 75 or a variant thereof; the amino acid sequence of the L-FR4 may include SEQ ID NO: 76 or a variant thereof; and the amino acid sequence of the H-FR1 may include SEQ ID NO: 67 or a variant thereof; the amino acid sequence of the H-FR2 may include SEQ ID NO: 68 or a variant thereof; the amino acid sequence of the H-FR3 may include SEQ ID NO: 69 or a variant thereof; and the amino acid sequence of the H-FR4 may include SEQ ID NO: 70 or a variant thereof. For example, the antibody or an antigen-binding fragment thereof may include the antibody YN-039 or an antibody with the same LCDR1-3, HCDR1-3, L-FR1-4 and H-FR1-4 therewith. In some embodiments, the reference antibody may include a light chain variable region and a heavy chain variable region, the amino acid sequence of the light chain variable region may include SEQ ID NO: 41 or a variant thereof; and the amino acid sequence of the heavy chain variable region may include SEQ ID NO: 35 or a variant thereof. For example, the reference antibody may include the antibody YN-039 or an antibody having the same light chain variable region and heavy chain variable region therewith. In some embodiments, the reference antibody may include a light chain and a heavy chain, the amino acid sequence of the light chain may be shown in SEQ ID NO: 42 and the heavy chain amino acid sequence may be shown in SEQ ID NO: 36. For example, the reference antibody may include the antibody YN-039 or have the same light chain and heavy chain therewith.

In the present application, the PD-L1 protein is selected from the group consisting of human PD-L1 protein, monkey PD-L1 protein and murine PD-L1 protein.

In another aspect, the present application further provides an antibody, an antigen binding fragment or a variant thereof which binds to a CD137 protein with a $K_D$ of lower than $5\times10^{-9}$ M (e.g., a $K_D$ of not higher than about $5\times10^{-9}$ M, not higher than about $4\times10^{-9}$ M, not higher than about $3\times10^{-9}$ M, not higher than about $2\times10^{-9}$ M, not higher than about $1\times10^{-9}$ M or not higher than about $1\times10^{-10}$ M or less). For example, it binds to a CD137 protein with a $K_D$ of lower than $3\times10^{-9}$ M.

The antibody, the antigen binding fragment or the variant thereof of the present application may relieve or treat tumors. For example, the tumor may include colon cancer.

In the present application, the antibody may be selected from the group consisting of monoclonal antibody, single-strand antibody, chimeric antibody, humanized antibody and fully human antibody.

In the present application, the antigen-binding fragment may be selected from the group consisting of Fab, Fab', $F(ab)_2$ and Fv fragment.

In the present application, the variant may be an amino acid sequence which has substantially the same function (e.g., a capacity of specifically binding to the CD137), and has at least 85% or more (e.g., at least about 85%, about 90%, about 91%, about 92%, about 93%, about 94%, about 95%, about 96%, about 97%, about 98%, about 99% or more) sequence identity thereto. In some embodiments, the variant of the amino acid sequence is an amino acid sequence which bas substantially the same function (e.g., a capacity of specifically binding to CD137), and on the basis further includes the addition, deletion or substitution of one or more (e.g., 1-2, 1-3, 1-4, 1-5, 1-6, 1-7, 1-8, 1-9, 1-10 or more) amino acids.

In some embodiments, the antibody may include an antibody light chain or a fragment thereof. For example, the antibody light chain or the fragment thereof may include LCDR1, and the LCDR1 may include the following amino acid sequence or a variant thereof. SEQ ID NO: 80. For example, the antibody light chain or the fragment thereof can include LCDR2 including the following amino acid sequence or a variant thereof; SEQ ID NO: 81. For another example, the antibody light chain or the fragment thereof includes LCDR3 or a variant thereof, and the LCDR3 can include an amino acid sequence shown in SEQ ID NO: 82.

In some embodiments, as to the antibody, the antigen binding fragment or the variant thereof, the antibody light chain or the fragment thereof further includes framework regions L-FR1, L-FR2, L-FR3 and L-FR4. For example, the C-terminus of the L-FR1 is directly or indirectly linked to the N-terminus of the LCDR1, and the L-FR1 can include an amino acid sequence shown in SEQ ID NO: 89. The L-FR2 is located between the LCDR1 and the LCDR2, and the L-FR2 may include an amino acid sequence shown in SEQ ID NO: 90. The L-FR3 is located between the LCDR2 and the LCDR3, and the L-FR3 may include an amino acid sequence shown in SEQ ID NO: 91. The N-terminus of the L-FR4 is directly or indirectly linked to the C-terminus of the LCDR3, and the L-FR4 may include an amino acid sequence shown in SEQ ID NO: 92.

In some embodiments, as to the antibody, the antigen binding fragment or the variant thereof, the antibody light chain or a fragment thereof includes a light chain variable region VL, and the light chain variable region VL may include the following amino acid sequence or a variant thereof; SEQ ID NO: 20.

In the present application, the antibody light chain or a fragment thereof may further include a human constant region, and the human constant region includes a human Igλ constant region.

In the present application, the light chain or the fragment thereof of the antibody may include an amino acid sequence shown in SEQ ID NO: 23.

In some embodiments, the antibody may include an antibody heavy chain or a fragment thereof. The antibody heavy chain or the fragment thereof includes HCDR1, and the HCDR1 may include the following amino acid sequence or a variant thereof; SEQ ID NO: 77. The antibody heavy chain or the fragment thereof includes HCDR2, and the HCDR2 may include the following amino acid sequence or a variant thereof; SEQ ID NO: 78. The antibody heavy chain or the fragment thereof includes HCDR3, and the HCDR3 may include the following amino acid sequence or a variant thereof; SEQ ID NO: 79.

In some embodiments, the antibody heavy chain or the fragment thereof may further include framework regions H-FR1, H-FR2, H-FR3 and H-FR4. The C-terminus of H-FR1 is directly or indirectly linked to the N-terminus of HCDR1, and the H-FR1 may include an amino acid sequence shown in SEQ ID NO: 84-85. The H-FR2 is located between the HCDR1 and the HCDR2, and the H-FR2 may include an amino acid sequence shown in SEQ ID NO: 86. The H-FR3 is located between the HCDR2 and the HCDR3, and the H-FR3 may include an amino acid sequence shown in SEQ ID NO: 87. The N-terminus of H-FR4 is directly or indirectly linked to the C-terminus of HCDR3, and the H-FR4 may include an amino acid sequence shown in SEQ ID NO: 88.

The antibody heavy chain or the fragment thereof of the present application includes a heavy chain variable region VH, and the heavy chain variable region VH may include an amino acid sequence or a variant thereof selected from the group consisting of SEQ ID NO: 18 or SEQ ID NO: 25.

In the antibody, the antigen binding fragment or the variant thereof of the present application, the antibody heavy chain or the fragment thereof may further include a human constant region. For example, the human constant region may include a human IgG constant region. For example, the human IgG constant region may include a human IgG1 constant region.

In the present application, the antibody heavy chain or the fragment thereof may include an amino acid sequence or a variant thereof selected from the group consisting of SEQ ID NO: 21 or SEQ ID NO: 27.

In some embodiments, the amino acid sequence of the LCDR1 of the antibody, the antigen binding fragment or the variant thereof of the present application may include SEQ ID NO: 80 or a variant thereof, the amino acid sequence of the LCDR2 may include SEQ ID NO: 81 or a variant thereof; the amino acid sequence of the LCDR3 may include SEQ ID NO: 82 or a variant thereof; and the amino acid sequence of the HCDR1 may include SEQ ID NO: 77 or a variant thereof; the amino acid sequence of the HCDR2 may include SEQ ID NO: 78 or a variant thereof; and the amino acid sequence of the HCDR3 may include SEQ ID NO: 79 or a variant thereof. For example, the antibody, the antigen binding fragment or the variant thereof may include the antibody YN-005 or an antibody with the same LCDR1-3 and HCDR1-3 therewith. In some embodiments, the amino acid sequence of the light chain variable region of the antibody, the antigen binding fragment or the variant thereof of the present application may include SEQ ID NO: 20 or a variant thereof; and the amino acid sequence of the heavy chain variable region may include SEQ ID NO: 18 or a variant thereof. For example, the antibody, the antigen binding fragment or the variant thereof can include the antibody YN-005 or an antibody having the same light chain variable region and heavy chain variable region therewith. In some embodiments, the antibody, the antigen binding fragment or the variant thereof of the present application may include a light chain and a heavy chain, the amino acid sequence of the light chain may be shown in SEQ ID NO: 23 and the heavy chain amino acid sequence may be shown in SEQ ID NO: 21. For example, the antibody, the antigen binding fragment or the variant thereof may include the antibody YN-005 or have the same light chain and heavy chain therewith.

In some embodiments, the antibody, the antigen binding fragment or the variant thereof of the present application competes with a reference antibody to bind to CD137 protein (e.g., human CD137 protein). The reference antibody may include LCDR1-3 and HCDR1-3, and the amino acid sequence of the LCDR1 may include SEQ ID NO: 80 or a variant thereof; the amino acid sequence of the LCDR2 may include SEQ ID NO: 81 or a variant thereof; the amino acid sequence of the LCDR3 may include SEQ ID NO: 82 or a variant thereof; and the amino acid sequence of the HCDR1 may include SEQ ID NO: 77 or a variant thereof; the amino acid sequence of the HCDR2 may include SEQ ID NO: 78 or a variant thereof; and the amino acid sequence of the HCDR3 may include SEQ ID NO: 79 or a variant thereof. In some embodiments, the reference antibody may include the antibody YN-005 or an antibody with the same LCDR1-3 and HCDR1-3 therewith. In some embodiments, the reference antibody may include a light chain variable region and a heavy chain variable region, the amino acid sequence of the light chain variable region may include SEQ ID NO: 20 or a variant thereof; and the amino acid sequence of the heavy chain variable region may include SEQ ID NO: 18 or a variant thereof. For example, the reference antibody may include the antibody YN-005 or an antibody having the same light chain variable region and heavy chain variable region therewith. In some embodiments, the reference antibody may include a light chain and a heavy chain, the amino acid sequence of the light chain may be shown in SEQ ID NO: 23 and the amino acid sequence of the heavy chain may be shown in SEQ ID NO: 21. For example, the reference antibody may include the antibody YN-005 or have the same light chain and heavy chain therewith.

In some embodiments, the amino acid sequence of the LCDR1 of the antibody, the antigen binding fragment or the variant thereof of the present application may include SEQ ID NO: 80 or a variant thereof, the amino acid sequence of the LCDR2 may include SEQ ID NO: 81 or a variant thereof the amino acid sequence of the LCDR3 may include SEQ ID NO: 82 or a variant thereof; and the amino acid sequence of the HCDR1 may include SEQ ID NO: 77 or a variant thereof, the amino acid sequence of the HCDR2 may include SEQ ID NO: 78 or a variant thereof; and the amino acid sequence of the HCDR3 may include SEQ ID NO: 79 or a variant thereof. For example, the antibody, the antigen binding fragment or the variant thereof may include the antibody YN-006 or an antibody with the same LCDR 1-3 and HCDR1-3 therewith. In some embodiments, the amino acid sequence of the light chain variable region of the antibody, the antigen binding fragment or the variant thereof of the present application may include SEQ ID NO: 20 or a variant thereof; and the amino acid sequence of the heavy chain variable region may include SEQ ID NO: 25 or a variant thereof. For example, the antibody, the antigen binding fragment or the variant thereof may include the antibody YN-006 or an antibody having the same light chain variable region and heavy chain variable region therewith. In some embodiments, the antibody, the antigen binding fragment or the variant thereof of the present application may include a light chain and a heavy chain, the amino acid sequence of the light chain may be shown in SEQ ID NO: 23 and the heavy chain amino acid sequence may be shown in SEQ ID NO: 27. For example, the antibody, the antigen binding fragment or the variant thereof can include the antibody YN-006 or have the same light chain and heavy chain therewith.

In some embodiments, the antibody, the antigen binding fragment or the variant thereof of the present application competes with a reference antibody to bind to CD137 protein (e.g., human CD137 protein). The reference antibody may include LCDR1-3 and HCDR1-3, and the amino acid sequence of the LCDR1 may include SEQ ID NO: 80 or a variant thereof; the amino acid sequence of the LCDR2 may include SEQ ID NO: 81 or a variant thereof; the amino acid sequence of the LCDR3 may include SEQ ID NO: 82 or a variant thereof; and the amino acid sequence of the HCDR1 may include SEQ ID NO: 77 or a variant thereof; the amino acid sequence of the HCDR2 may include SEQ ID NO: 78 or a variant thereof; and the amino acid sequence of the HCDR3 may include SEQ ID NO: 79 or a variant thereof. In some embodiments, the reference antibody may include the antibody YN-006 or an antibody with the same LCDR1-3 and HCDR1-3 therewith. In some embodiments, the reference antibody may include a light chain variable region and a heavy chain variable region, the amino acid sequence of the light chain variable region may include SEQ ID NO: 20 or a variant thereof; and the amino acid sequence of the heavy chain variable region may include SEQ ID NO: 25 or a variant thereof. For example, the reference antibody may include the antibody YN-006 or an antibody having the same light chain variable region and heavy chain variable region therewith. In some embodiments, the reference antibody may include a light chain and a heavy chain, the amino acid sequence of the light chain may be shown in SEQ ID NO: 23 and the amino acid sequence of the heavy chain may be shown in SEQ ID NO: 27. For example, the reference antibody may include the antibody YN-006 or have the same light chain and heavy chain therewith.

In the present application, the CD137 protein may include a human CD137 protein.

In another aspect, the present application further provides a bispecific antibody which binds to a PD-L1 protein at a $K_D$ of lower than $2\times10^{-9}$ M (e.g., a $K_D$ of not higher than about $2\times10^{-9}$ M, not higher than about $1\times10^{-9}$ M, not higher than about $1\times10^{-10}$ M or not higher than about 8×10 M or less), and binds to a CD137 protein with a $K_D$ of lower than $8\times10^{-9}$ M (e.g., a $K_D$ of not higher than about $8\times10^{-9}$ M, not higher than about $7\times10^{-9}$ M, not higher than about $6\times10^{-9}$ M, not higher than about $5\times10^{-9}$ M, not higher than about $4\times10^{-9}$ M, not higher than about $3\times10^{-9}$ M, not higher than about $2\times10^{-9}$ M, not higher than about $1\times10^{-9}$ M or not higher than about $1\times10^{-10}$ M or less).

In the present application, the PD-L1 protein is selected from the group consisting of human PD-L1 protein, monkey PD-L1 protein and murine PD-L1 protein; and the CD137 protein includes a human CD137 protein.

In the present application, the bispecific antibody includes a first targeting moiety that specifically binds to the PD-L1 protein, wherein the first targeting moiety may include the antibody, the antigen binding fragment or the variant thereof which binds to the PD-L1.

For example, the antigen-binding fragment in the first targeting moiety may be selected from the group consisting of Fab, Fab', $F(ab)_2$ and Fv fragment. For another example, the variant in the first targeting moiety may be selected from the group consisting of a protein or polypeptide which undergoes the substitution, deletion or addition of one or more amino acids in the antibody or an antigen-binding fragment thereof; and a protein or polypeptide having 85% or more (e.g., at least about 85%, about 90%, about 91%, about 92%, about 93%, about 94%, about 95%, about 96%, about 97%, about 98%, about 99% or more) sequence identity with the antibody or the antigen-binding fragment thereof. The antibody, the antigen binding fragment or the variant thereof may be the antibody, the antigen binding fragment or the variant thereof which binds to the PD-L1 protein.

In some embodiments, the antibody which binds to the PD-L1 protein in the bispecific antibody may include a light chain or a fragment thereof. For example, the light chain or the fragment thereof includes LCDR1-3, and the amino acid sequence of the LCDR1 is SEQ ID NO: 54-58; the amino acid sequence of the LCDR2 is SEQ ID NO: 60-61; and the amino acid sequence of the LCDR3 is selected from the group consisting of SEQ ID NO: 63-64. In some embodiments, the light chain or the fragment thereof may include a light chain variable region, and the amino acid sequence of the light chain variable region may be selected from the group consisting of SEQ ID NO: 4, SEQ ID NO: 11, SEQ ID NO: 33, SEQ ID NO: 37, SEQ ID NO: 39 and SEQ ID NO: 41. In some embodiments, the light chain or the fragment thereof of the antibody may include a human constant region, and the human constant region includes a human Igλ constant region.

In some embodiments, the light chain or the fragment thereof may include an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

In some embodiments, the antibody binding to the PD-L1 protein may include a heavy chain or a fragment thereof. For example, the heavy chain or the fragment thereof includes HCDR1-3, and the amino acid sequence of the HCDR1 is selected from the group consisting of SEQ ID NO: 46-47; the amino acid sequence of the HCDR2 is SEQ ID NO: 48; and the amino acid sequence of the HCDR3 is SEQ ID NO: 50-52.

In some embodiments, the heavy chain or the fragment thereof may include a heavy chain variable region, and the amino acid sequence of the heavy chain variable region may be selected from the group consisting of SEQ ID NO: 2, SEQ ID NO: 9, SEQ ID NO: 31 and SEQ ID NO: 35.

In some embodiments, the heavy chain or the fragment thereof may further include a human constant region, and the human constant region may include a human IgG constant region. For example, the human IgG constant region is human IgG1 constant region.

In some embodiments, the heavy chain or the fragment thereof may include an amino acid sequence selected from the group consisting of SEQ ID NO: 6, SEQ ID NO:13, SEQ ID NO: 32 and SEQ ID NO: 36.

In some embodiments, the bispecific antibody includes a second targeting moiety that specifically binds to the CD137 protein, wherein the second targeting moiety can include an antibody, the antigen binding fragment or the variant thereof which binds to the CD137 protein. In some embodiments, the antigen-binding fragment is selected from the group consisting of Fab, Fab', $F(ab)_2$ and Fv fragment. In some embodiments, the variant is selected from the group consisting of a protein or polypeptide which undergoes the substitution, deletion or addition of one or more amino acids in the antibody or the antigen-binding fragment thereof; and a protein or polypeptide having 85% or more (e.g., at least about 85%, about 90%, about 91%, about 92%, about 93%, about 94%, about 95%, about 96%, about 97%, about 98%, about 99% or more) sequence identity with the antibody or the antigen-binding fragment thereof.

In some embodiments, the antibody that binds to the CD137 protein may include a light chain or a fragment thereof. For example, the light chain or the fragment thereof includes LCDR1-3, and the amino acid sequences of the LCDR1-3 can be sequentially SEQ ID NO: 80, SEQ ID NO: 81 and SEQ ID NO: 82. In some embodiments, the light chain of the fragment thereof may include a light chain variable region, and the light chain variable region includes an amino acid sequence shown in SEQ ID NO: 20.

In some embodiments, the antibody that binds to the CD137 protein may include a heavy chain or a fragment thereof. In some embodiments, the heavy chain or the fragment thereof of the antibody may include HCDR1-3, and the amino acid sequences of the HCDR1-3 may be sequentially SEQ ID NO: 77, SEQ ID NO: 78 and SEQ ID NO: 79. In some embodiments, the heavy chain or the fragment thereof of the antibody may include a heavy chain variable region, and the amino acid sequence of the heavy chain variable region may be selected from the group consisting of SEQ ID NO: 18 and SEQ ID NO: 25.

In some embodiments, the antibody that binds to the CD137 protein may include a scFv, and the scFv may include an amino acid sequence shown in SEQ ID NO: 83.

In the present application, the bispecific antibody may include a first polypeptide chain and a second polypeptide chain, wherein the first polypeptide chain may include the heavy chain variable region of the antibody that binds to the PD-L1 protein, the heavy chain variable region of the antibody that binds to the CD137 protein, and the light chain variable region of the antibody that binds to the CD137 protein; and the second polypeptide chain may include the light chain variable region of the antibody that binds to the PD-L1 protein.

For example, in the first polypeptide chain, the heavy chain variable region of the antibody that binds to the PD-L1 protein may be located at the N-terminus of the heavy chain variable region of the antibody that binds to the CD137 protein, and the heavy chain variable region of the antibody that binds to the CD137 protein may be located at the N-terminus of the light chain variable region of the antibody that binds to the CD137 protein. For another example. in the first polypeptide chain, the heavy chain variable region of the antibody that binds to the PD-L1 protein may be located at the N-terminus of the light chain variable region of the antibody that binds to the CD137 protein, and the light chain variable region of the antibody that binds to the CD137 protein may be located at the N-terminus of the heavy chain variable region of the antibody that binds to the CD137 protein.

For example, in the first polypeptide chain, the light chain variable region of the antibody that binds to the CD137 protein and the heavy chain variable region of the antibody that binds to the CD137 protein constitute scFv. For example, the scFv can include an amino acid sequence shown in SEQ ID NO: 83.

The first polypeptide chain may further include a human IgG constant region. For example, the human IgG constant region may be a human IgG1 constant region, In some embodiments, the human IgG constant region may be located at the C-terminus of the heavy chain variable region of the antibody that binds to the PD-L1 protein and may be located at the N-terminus of the light chain variable region of the antibody that binds to the CD137 protein; alternatively, the human IgG constant region may be located at the C-terminus of the heavy chain variable region of the antibody that binds to the PD-L1 protein and may be located at the N-terminus of the heavy chain variable region of the antibody that binds to the CD137 protein.

In some embodiments, the first polypeptide chain may include an amino acid sequence shown in SEQ ID NO: 30, SEQ ID NO: 43 and SEQ ID NO: 44.

In some embodiments, the second polypeptide chain may further include a human Igλ constant region.

In the present application, the second polypeptide chain may include the following amino acid sequences: SEQ ID NO: 15 and SEQ ID NO: 34.

For example, in the first targeting moiety of the bispecific antibody of the present application, the amino acid sequence of the LCDR1 may be selected from the group consisting of SEQ ID NO: 54, SEQ ID NO: 55, SEQ ID NO: 56, SEQ ID NO: 57 and SEQ ID NO: 58 or a variant thereof; the amino acid sequence of the LCDR2 may be selected from the group consisting of SEQ ID NO: 60 and SEQ ID NO: 61 or a variant thereof; the amino acid sequence of the LCDR3 may be selected from the group consisting of SEQ ID NO: 63 and SEQ ID NO: 64 or a variant thereof; and the amino acid sequence of the HCDR1 may be selected from the group consisting of SEQ ID NO: 46 and SEQ ID NO: 47 or a variant thereof; the amino acid sequence of the HCDR2 may include SEQ ID NO: 48 or a variant thereof; and the amino acid sequence of the HCDR3 may be selected from the group consisting of SEQ ID NO: 50-52 or a variant thereof. In some embodiments, the amino acid sequence of the light chain variable region of the antibody, the antigen binding fragment or the variant thereof of the present application may be selected from the group consisting of SEQ ID NO: 4, SEQ ID NO: 11, SEQ ID NO: 33, SEQ ID NO: 37, SEQ ID NO: 39 and SEQ ID NO: 41 or a variant thereof; and the amino acid sequence of the heavy chain variable region may be selected from the group consisting of SEQ ID NO: 2, SEQ ID NO: 9, SEQ ID NO: 31 and SEQ ID NO: 35 or a variant thereof. In some embodiments, the antibody, the antigen binding fragment or the variant thereof of the present application may include a light chain and a heavy chain, the amino acid sequence of the light chain may be an amino acid sequence selected from the group consisting of SEQ ID NO: 8, SEQ ID NO: 15, SEQ ID NO: 34, SEQ ID NO: 38, SEQ ID NO: 40 and SEQ ID NO: 42, and the heavy chain amino acid sequence may be an amino acid sequence selected from the group consisting of SEQ ID NO: 6, SEQ ID NO: 13, SEQ ID NO: 32 and SEQ ID NO: 36.

For example, in the second targeting moiety of the bispecific antibody of the present application, the amino acid sequence of the LCDR1 may include SEQ ID NO: 80 or a variant thereof; the amino acid sequence of the LCDR2 may include SEQ ID NO: 81 or a variant thereof; the amino acid sequence of the LCDR3 may include SEQ ID NO: 82 or a variant thereof; and the amino acid sequence of the HCDR1 may include SEQ ID NO: 77 or a variant thereof; the amino acid sequence of the HCDR2 may include SEQ ID NO: 78 or a variant thereof; and the amino acid sequence of the HCDR3 may include SEQ ID NO: 79 or a variant thereof. In some embodiments, the amino acid sequence of the light chain variable region of the antibody, the antigen binding fragment or the variant thereof of the present application may include SEQ ID NO: 20 or a variant thereof; and the amino acid sequence of the heavy chain variable region may be those selected from the group consisting of SEQ ID NO: 18 and SEQ ID NO: 25 or their variants. In some embodiments, the antibody, the antigen binding fragment or the variant thereof of the present application may include a light chain and a heavy chain, the amino acid sequence of the light chain may be shown in SEQ ID NO: 23 and the heavy chain amino acid sequence may be shown in SEQ ID NO: 21 or SEQ ID NO: 27.

For example, in the bispecific antibody of the present application, the first polypeptide may include an amino acid sequence shown in SEQ ID NO: 30, and the second polypeptide may include an amino acid sequence shown in SEQ ID NO: 15. The bispecific antibody may include the antibody YN-007 or an antibody with the same first polypeptide and second polypeptide, wherein, the first polypeptide may include an amino acid sequence shown in SEQ ID NO: 25, an amino acid sequence shown in SEQ ID NO: 20 and an amino acid sequence shown in SEQ ID NO: 13; and the second polypeptide may include an amino acid sequence shown in SEQ ID NO: 15.

For another example, in the bispecific antibody of the present application, the first polypeptide may include an amino acid sequence shown in SEQ ID NO: 43, and the second polypeptide may include an amino acid sequence shown in SEQ ID NO: 34. The bispecific antibody may include the antibody YN-051 or an antibody with the same first polypeptide and second polypeptide. Wherein, the first polypeptide may include an amino acid sequence shown in SEQ ID NO: 25, an amino acid sequence shown in SEQ ID NO: 20 and an amino acid sequence shown in SEQ ID NO: 32; and the second polypeptide may include an amino acid sequence shown in SEQ ID NO: 34.

For another example, in the bispecific antibody of the present application, the first polypeptide may include an amino acid sequence shown in SEQ ID NO: 44, and the second polypeptide may include an amino acid sequence shown in SEQ ID NO: 34. The bispecific antibody may include the antibody YN-052 or an antibody with the same first polypeptide and second polypeptide. Wherein, the first polypeptide may include an amino acid sequence shown in SEQ ID NO: 25, an amino acid sequence shown in SEQ ID NO: 20 and an amino acid sequence shown in SEQ ID NO: 36; and the second polypeptide may include an amino acid sequence shown in SEQ ID NO: 34.

For example, in the bispecific antibody of the present application, the first polypeptide may include an amino acid sequence shown in SEQ ID NO: 30, and the second polypeptide may include an amino acid sequence shown in SEQ ID NO: 15. The bispecific antibody may include the antibody YN-007 or an antibody with the same first polypeptide and second polypeptide. Wherein, the first polypeptide may include an amino acid sequence shown in SEQ ID NO: 27, an amino acid sequence shown in SEQ ID NO: 23 and an amino acid sequence shown in SEQ ID NO: 13; and the second polypeptide may include an amino acid sequence shown in SEQ ID NO: 15.

For another example, in the bispecific antibody of the present application, the first polypeptide may include an amino acid sequence shown in SEQ ID NO: 43, and the second polypeptide may include an amino acid sequence shown in SEQ ID NO: 34. The bispecific antibody can include the antibody YN-051 or an antibody with the same first polypeptide and second polypeptide. Wherein, the first polypeptide may include an amino acid sequence shown in SEQ ID NO: 32, an amino acid sequence shown in SEQ ID NO: 27, an amino acid sequence shown in SEQ ID NO: 23; and the second polypeptide may include an amino acid sequence shown in SEQ ID NO: 34.

For another example, in the bispecific antibody of the present application, the first polypeptide may include an amino acid sequence shown in SEQ ID NO: 44, and the second polypeptide may include an amino acid sequence shown in SEQ ID NO: 34. The bispecific antibody may include the antibody YN-052 or an antibody with the same first polypeptide and second polypeptide. Wherein, the first polypeptide may include an amino acid sequence shown in SEQ ID NO: 36, an amino acid sequence shown in SEQ ID NO: 27, an amino acid sequence shown in SEQ ID NO: 23; and the second polypeptide may include an amino acid sequence shown in SEQ ID NO: 34.

Nucleic Acid, Vector, Host Cell and Preparation Method

In another aspect, the present application further provides one or more isolated nucleic acid molecules which can encode the antibody, the antigen binding fragment or the variant thereof, or the bispecific antibody of the present application. For example, each nucleic acid molecule of the one or more nucleic acid molecules may either encode the whole antibody or an antigen-binding fragment thereof, or encode a portion therein (e.g., one or more of HCDR1-3, LCDR1-3, VL, VH, light chain or heavy chain).

The nucleic acid molecule of the present application may be isolated. For example, it may be produced or synthesized by the following methods: (i) in vitro amplification, such as, amplification via a polymerase chain reaction (PCR), (ii) clonal recombination, (iii) purification, such as, fractionation by restriction enzyme digestion and gel electrophoresis, or (iv) synthesis, such as, by chemical synthesis. In some embodiments, the isolated nucleic acid is a nucleic acid molecule prepared by the recombinant DNA technology.

In the present application, the nucleic acid encoding the antibody or the antigen-binding fragment thereof may be prepared by a variety of methods known in the art, including but not limited to, overlap extension PCR by using restriction fragment operation or synthetic oligonucleotides. For specific operations, please refer to Sambrook et al., Molecular Cloning, A Laboratory Manual, Cold Spring Harbor Laboratory Press, Cold Spring Harbor, N.Y., 1989; and Ausabe, et al., Current Protocols in Molecular Biology, Greene Publishing and Wiley-Interscience, New York N.Y., 1993.

In another aspect, the present application provides one or more vectors, and includes the one or more nucleic acid molecules of the present application. Each vector may include one or more of the nucleic acid molecules. Moreover, the vector may further include other genes, such as, marker genes that allow selecting this vector in an appropriate host cell and under appropriate conditions. Moreover, the vector may further include an expression control element that allows the coding region to be correctly expressed in an appropriate host cell. Such control elements are well known by persons skilled in the art, e.g., they may include promoters, ribosome binding sites, enhancers and other control elements for regulating gene transcription or mRNA translation, etc. In some embodiments, the expression control sequence is a regulatory element. The specific structure of the expression control sequence may vary depending on the function of the species or cell types, but usually includes 5'non-transcribed sequence and 5' and 3'non-translated sequence involved in transcription and translation initiation, such as, TATA box, capped sequence, CAAT sequence, etc. For example, 5'non-transcribed expression control sequence may include the promoter region that may include a promoter sequence for transcriptional control of the functionally linked nucleic acid. One or more nucleic acid molecules described in the present application may be operably linked to the expression control element.

The vector may include, e.g., plasmid, cosmid, virus, phage, or other vectors commonly used in genetic engineering, for example, the vector is an expression vector.

In another aspect, the present application provides a cell, which may include the nucleic acid molecule of the present application and/or the vector described in the present application. The cell may be a host cell. In some embodiments, each host cell may include one nucleic acid molecule or vector described in the present application. In some embodiments, each host cell may include multiple (e.g., two or more) nucleic acid molecules or vectors described in the present application. For example, the vector of the present application may be introduced into the host cell, e.g., a eukaryotic cell, e.g., a plant-derived cell, fungus or yeast cells, etc. The vector of the present application may be introduced into the host cell by methods known in the art, such as electroporation, lipofectine transfection, lipofectamin transfection, and the like.

In another aspect, the present application provides one or more host cells, which include the nucleic acid molecule or the vector.

In another aspect, the present application provides a method for preparing the antibody, the antigen binding fragment or the variant thereof, or the bispecific antibody. The method may include culturing the host cell of the present application under conditions that allow the antibody, the antigen-binding fragment or variant thereof, or the bispecific antibody to be expressed, and optionally harvesting the antibody, antigen-binding fragment or variant thereof. For example, it is possible to use an appropriate medium, an appropriate temperature, a culture time, etc., and these methods are understood by those of ordinary skills in the art.

Pharmaceutical Composition, Use

In another aspect, the present application provides a pharmaceutical composition which may include the antibody, the antigen binding fragment or the variant thereof, or the bispecific antibody, the nucleic acid molecule, the vector and/or the host cell, and optionally a pharmaceutical acceptable adjuvant.

The pharmaceutical acceptable adjuvant may include buffers, antioxidants, preservatives, low molecular weight polypeptides, proteins, hydrophilic polymers, amino acids, sugars, chelators, counter-ions, metal complexes and/or nonionic surfactant and the like.

In the present application, the pharmaceutical composition may be formulated for oral administration, intravenous administration, intramuscular administration, in situ administration at the tumor site, inhalation, rectal administration, vaginal administration, transdermal administration or administration via subcutaneous depot.

In another aspect, the present application provides use of the antibody, the antigen binding fragment or the variant thereof, or the bispecific antibody, the nucleic acid molecule, the vector, the host cell and/or the pharmaceutical composition in manufacture of a drug for relieving or treating tumors. Among others, the tumors include colon cancer.

In another aspect, the present application provides a method of enhancing the function of T cells, including administering the antibody that binds to the PD-L1 protein, the antigen binding fragment or the variant thereof, the antibody that binds to the CD137 protein, the antigen binding fragment or the variant thereof, or the bispecific antibody, the nucleic acid molecule, the vector, the host cell and/or the pharmaceutical composition to a subject in need thereof. Of those, the T cells are tumor associated dysfunctional T cells.

In another aspect, the present application provides a method of inhibiting the binding of PD-L1 protein to PD-1 protein which includes administering the antibody, the antigen binding fragment or the variant thereof, or the bispecific antibody, the nucleic acid molecule, the vector, the host cell and/or the pharmaceutical composition to a subject in need thereof.

In the present application, the position of the antibody CDR may be determined in accordance with the antibody Kabat definition method.

The present application further includes the following embodiments.

1. An antibody, an antigen binding fragment or a variant thereof which binds to a PD-L1 protein with a $K_D$ of $3\times10^{-9}$ M or less.
2. The antibody, the antigen binding fragment or the variant thereof according to embodiment 1, which binds to a PD-L1 protein with a $K_D$ of $8\times10^{-11}$ M or less.
3. The antibody, the antigen binding fragment or the variant thereof according to any of embodiments 1-2, which inhibits the binding of PD-L1 to PD-1.
4. The antibody, the antigen binding fragment or the variant thereof according to any of embodiments 1-3, is capable of relieving or treating tumor-associated diseases.
5. The antibody, the antigen binding fragment or the variant thereof according to embodiment 4, wherein the tumor includes colon cancer.
6. The antibody, the antigen binding fragment or the variant thereof according to any of embodiments 1-5, wherein the antibody is selected from the group consisting of monoclonal antibody, single-strand antibody, chimeric antibody, humanized antibody and fully human antibody.
7. The antibody, the antigen binding fragment or the variant thereof according to any of embodiments 1-6, wherein the antigen-binding fragment is selected from the group consisting of Fab, Fab', $F(ab)_2$ and Fv fragment.
8. The antibody, the antigen binding fragment or the variant thereof according to any of embodiments 1-7, wherein the variant is selected from the group consisting of:
1) a protein or polypeptide obtained by substitution, deletion or addition of one or more amino acids in the antibody or the antigen-binding fragment thereof; and
2) a protein or polypeptide having 90% or more of sequence identity as the antibody or the antigen-binding fragment thereof.
9. The antibody, the antigen binding fragment or the variant thereof according to any of embodiments 1-8, which competes with a reference antibody which binds to the PD-L1 protein, wherein the reference antibody includes a light chain variable region and a heavy chain variable region, the light chain variable region of the reference antibody includes LCDR1-3, the light chain variable region of the reference antibody includes LCDR1-3, and the LCDR1 includes an amino acid sequence selected from the group consisting of SEQ ID NO: 54-58; the LCDR2 includes an amino acid sequence selected from the group consisting of SEQ ID NO: 60-61; and the LCDR3 includes an amino acid sequence selected from the group consisting of SEQ ID NO: 63-64; and the heavy chain variable region of the reference antibody includes HCDR1-3, the HCDR1 includes an amino acid sequence selected from the group consisting of SEQ ID NO: 46-47; the HCDR2 includes an amino acid sequence selected from the group consisting of SEQ ID NO: 48; and the HCDR3 includes an amino acid sequence selected from the group consisting of SEQ ID NO: 50-52.
10. The antibody, the antigen binding fragment or the variant thereof according to embodiment 9, wherein the light chain variable region of the reference antibody includes an amino acid sequence selected from the group consisting of SEQ ID NO: 4, SEQ ID NO: 11, SEQ ID NO: 33, SEQ ID NO: 37, SEQ ID NO: 39 and SEQ ID NO: 41, and the heavy chain variable region of the reference antibody includes an amino acid sequence selected from the group consisting of SEQ ID NO: 2, SEQ ID NO: 9, SEQ ID NO: 31 and SEQ ID NO: 35.
11. The antibody, the antigen binding fragment or the variant thereof according to any of embodiment 9-10, wherein the light chain of the reference antibody includes an amino acid sequence selected from the group consisting of SEQ ID NO: 8, SEQ ID NO: 15, SEQ ID NO: 34, SEQ ID NO: 38, SEQ ID NO: 40 and SEQ ID NO: 42; and the heavy chain of the reference antibody includes an amino acid sequence selected from the group consisting of SEQ ID NO: 6, SEQ ID NO: 13, SEQ ID NO: 32 and SEQ ID NO: 36.
12. The antibody, the antigen binding fragment or the variant thereof according to embodiments 1-11, wherein the antibody includes an antibody light chain or a fragment thereof which includes a LCDR1, and the LCDR1 includes an amino acid sequence shown in SEQ ID NO: 53: $TGTX_1SX_2VGGYX_3X_4VS$; wherein $X_1$ is S, R or V; $X_2$ is D, E or S; $X_3$ is N or R; $X_4$ is Y or E, and wherein the LCDR1 is determined according to the index of the antibody Kabat number.
13. The antibody, the antigen binding fragment or the variant thereof according to embodiment 12, wherein the LCDR1 includes an amino acid sequence selected from the group consisting of SEQ ID NO: 54-58.
14. The antibody, the antigen binding fragment or the variant thereof according to any of embodiments 11-13, wherein the antibody light chain or the fragment thereof includes a LCDR2 including an amino acid sequence shown in SEQ ID NO: 59: $X_1NSX_2RPS$, wherein $X_1$ is G or E; $X_2$ is N or L, and wherein the LCDR2 is determined according to the index of the antibody Kabat number.
15. The antibody, the antigen binding fragment or the variant thereof according to embodiment 14, wherein the LCDR2 includes an amino acid sequence selected from the group consisting of SEQ ID NO: 60-61.
16. The antibody, the antigen binding fragment or the variant thereof according to any of embodiments 11-15, wherein the antibody light chain or the fragment thereof includes a LCDR3 including an amino acid sequence shown in SEQ ID NO: 62: $QSYDSSLSGX_1V$, wherein $X_1$ is S or T, and wherein the LCDR3 is determined according to the index of the antibody Kabat number.
17. The antibody, the antigen binding fragment or the variant thereof according to any of embodiments 11-16, wherein the antibody light chain or the fragment thereof further includes framework regions L-FR1, L-FR2, L-FR3, and L-FR4.
18. The antibody, the antigen binding fragment or the variant thereof according to embodiment 17, wherein the framework regions are selected from the group consisting of human consensus framework sequences and human germline sequences.
19. The antibody, the antigen binding fragment or the variant thereof according to any of embodiments 17-18, wherein the C-terminus of the L-FR1 is directly or indirectly linked to the N-terminus of the LCDR1, and the L-FR1 includes an amino acid sequence selected from the group consisting of SEQ ID NO: 71.

20. The antibody, the antigen binding fragment or the variant thereof according to any of embodiments 17-19, wherein the L-FR2 is located between the LCDR1 and the LCDR2, and the L-FR2 includes an amino acid sequence selected from the group consisting of SEQ ID NO: 72.

21. The antibody, the antigen binding fragment or the variant thereof according to any of embodiments 17-20, wherein the L-FR3 is located between the LCDR2 and the LCDR3, and the L-FR3 includes an amino acid sequence selected from the group consisting of SEQ ID NO: 73-75.

22. The antibody, the antigen binding fragment or the variant thereof according to any of embodiments 17-21, wherein the N-terminus of the L-FR4 is directly or indirectly linked to the C-terminus of the LCDR3, and the L-FR4 includes an amino acid sequence selected from the group consisting of SEQ ID NO: 76.

23. The antibody, the antigen binding fragment or the variant thereof according to any of embodiments 12-22, wherein the antibody light chain or a fragment thereof includes a light chain variable region VL, and the light chain variable region VL includes an amino acid sequence selected from the group consisting of SEQ ID NO: 4, SEQ ID NO: 11, SEQ ID NO: 33, SEQ ID NO: 37, SEQ ID NO: 39 and SEQ ID NO: 41.

24. The antibody, the antigen binding fragment or the variant thereof according to any of embodiments 12-23, wherein the antibody light chain or the fragment thereof further includes a human constant region, and the human constant region includes a human Igλ constant region.

25. The antibody, the antigen binding fragment or the variant thereof according to any of embodiments 12-24, wherein the antibody light chain or the fragment thereof includes an amino acid sequence selected from the group consisting of SEQ ID NO: 8, SEQ ID NO: 15, SEQ ID NO: 34, SEQ ID NO: 38, SEQ ID NO: 40 and SEQ ID NO: 42.

26. The antibody, the antigen binding fragment or the variant thereof according to any of embodiments 1-25, wherein the antibody includes an antibody heavy chain or a fragment thereof which includes HCDR1, and the HCDR1 includes an amino acid sequence selected from the group consisting of those shown in SEQ ID NO: 45: $X_1$YAIS, wherein $X_1$ is S or T, and wherein the HCDR1 is determined according to the index of the antibody Kabat number.

27. The antibody, the antigen binding fragment or the variant thereof according to embodiment 26, wherein the antibody heavy chain or the fragment thereof includes HCDR2, the HCDR2 includes an amino acid sequence shown in SEQ ID NO: 48, and wherein the HCDR2 is determined according to the index of the antibody Kabat number.

28. The antibody, the antigen binding fragment or the variant thereof according to any of embodiments 26-27, wherein the antibody heavy chain or the fragment thereof includes HCDR3, and the HCDR3 includes an amino acid sequence selected from that shown in SEQ ID NO: 49: TM$X_1X_2$Y$X_3X_4$GN$X_5$DY, wherein $X_1$ is D, E or G, $X_2$ is G or E, $X_3$ is S or G, $X_4$ is Y or F, $X_5$ is F or Y, and wherein the HCDR3 is determined according to the index of the antibody Kabat number.

29. The antibody, the antigen binding fragment or the variant thereof according to embodiment 28, wherein the HCDR3 includes an amino acid sequence selected from the group consisting of SEQ ID NO: 50-52.

30. The antibody, the antigen binding fragment or the variant thereof according to any of embodiments 26-29, wherein the antibody heavy chain or the fragment thereof further includes framework regions H-FR1, H-FR2, H-FR3, and H-FR4.

31. The antibody, the antigen binding fragment or the variant thereof according to embodiments 30, wherein the framework regions are selected from the group consisting of human consensus framework sequences and human germline sequences.

32. The antibody, the antigen binding fragment or the variant thereof according to any of embodiments 30-31, wherein the C-terminus of H-FR1 is directly or indirectly linked to the N-terminus of HCDR1, and the H-FR1 includes an amino acid sequence selected from the group consisting of SEQ ID NO: 65-67.

33. The antibody, the antigen binding fragment or the variant thereof according to any of embodiments 30-32, wherein the H-FR2 is located between the HCDR1 and the HCDR2, and the H-FR2 includes an amino acid sequence selected from the group consisting of SEQ ID NO: 68.

34. The antibody, the antigen binding fragment or the variant thereof according to any of embodiments 30-33, wherein the H-FR3 is located between the HCDR2 and the HCDR3, and the H-FR3 includes an amino acid sequence selected from the group consisting of SEQ ID NO: 69.

35. The antibody, the antigen binding fragment or the variant thereof according to any of embodiments 30-34, wherein the N-terminus of H-FR4 is directly or indirectly linked to the C-terminus of HCDR3, and the H-FR4 includes an amino acid sequence selected from the group consisting of SEQ ID NO: 70.

36. The antibody, the antigen binding fragment or the variant thereof according to any of embodiments 26-35, wherein the antibody heavy chain or the fragment thereof includes a heavy chain variable region VH, and the heavy chain variable region VH includes an amino acid sequence selected from the group consisting of SEQ ID NO: 2, SEQ ID NO: 9, SEQ ID NO: 31 and SEQ ID NO: 35.

37. The antibody, the antigen binding fragment or the variant thereof according to any of embodiments 26-36, wherein the antibody heavy chain or the fragment thereof further includes a human constant region, and the human constant region includes a human IgG1 constant region.

38. The antibody, the antigen binding fragment or the variant thereof according to any of embodiments 26-37, wherein the antibody heavy chain or the fragment thereof includes an amino acid sequence selected from the group consisting of SEQ ID NO: 6, SEQ ID NO: 13, SEQ ID NO: 32 and SEQ ID NO: 36.

39. The antibody, the antigen binding fragment or the variant thereof according to any of embodiments 1-38, wherein the PD-L1 protein is selected from the group consisting of human PD-L1 protein, monkey PD-L1 protein and murine PD-L1 protein.

40. An antibody, an antigen binding fragment or a variant thereof which binds to a CD137 protein with a $K_D$ of $5\times10^{-9}$ M or less.
41. The antibody, the antigen binding fragment or the variant thereof according to embodiment 40, which binds to a CD137 protein with a $K_D$ of $3\times10^{-9}$ M or less.
42. The antibody, the antigen binding fragment or the variant thereof according to any of embodiments 40-41, which has a CD137 agonistic activity.
43. The antibody, the antigen binding fragment or the variant thereof according to any of embodiments 40-42, is capable of relieving or treating tumors.
44. The antibody, the antigen binding fragment or the variant thereof according to embodiment 43, wherein the tumor includes colon cancer.
45. The antibody, the antigen binding fragment or the variant thereof according to any of embodiments 40-44, wherein the antibody is selected from the group consisting of monoclonal antibody, single-strand antibody, chimeric antibody, humanized antibody and fully human antibody.
46. The antibody, the antigen binding fragment or the variant thereof according to any of embodiments 40-45, wherein the antigen-binding fragment is selected from the group consisting of Fab, Fab', $F(ab)_2$ and Fv fragment.
47. The antibody, the antigen binding fragment or the variant thereof according to any of embodiments 40-46, wherein the variant is selected from the group consisting of:
1) a protein or polypeptide obtained by substitution, deletion or addition of one or more amino acids in the antibody or the antigen-binding fragment thereof; and
2) a protein or polypeptide having 90% or more of sequence identity as the antibody or the antigen-binding fragment thereof.
48. The antibody, the antigen binding fragment or the variant thereof according to any of embodiments 40-47, which competes with a reference antibody to bind to the CD137 protein, wherein the reference antibody includes a light chain variable region and a heavy chain variable region, the light chain variable region of the reference antibody includes LCDR1-3, and the amino acid sequence of the LCDR1-3 are sequentially shown in SEQ ID NO: 80-82, and the heavy chain variable region of the reference antibody includes HCDR1-3, and the amino acid sequences of the HCDR1-3 are sequentially shown in SEQ ID NO: 77-79.
49. The antibody, the antigen binding fragment or the variant thereof according to embodiment 48, wherein the light chain variable region of the reference antibody includes an amino acid sequence selected from that shown in SEQ ID NO: 20, and the heavy chain variable region of the reference antibody includes an amino acid sequence selected from those shown in SEQ ID NO: 18 and SEQ ID NO: 25
50. The antibody, the antigen binding fragment or the variant thereof according to any of embodiments 48-49, wherein the light chain of the reference antibody includes an amino acid sequence selected from that shown in SEQ ID NO: 23; and the heavy chain of the reference antibody includes an amino acid sequence selected from those shown in SEQ ID NO: 21 and SEQ ID NO: 27.
51. The antibody, the antigen binding fragment or the variant thereof according to any of embodiments 40-50, wherein the antibody includes an antibody light chain or a fragment thereof.
52. The antibody, the antigen binding fragment or the variant thereof according to embodiment 51, wherein the antibody light chain or the fragment thereof includes a LCDR1, and the LCDR1 includes an amino acid sequence selected from that shown in SEQ ID NO: 80.
53. The antibody, the antigen binding fragment or the variant thereof according to any of embodiments 51-52, wherein the antibody light chain or the fragment thereof includes LCDR2, and the LCDR2 includes an amino acid sequence shown in SEQ ID NO: 81.
54. The antibody, the antigen binding fragment or the variant thereof according to any of embodiments 51-53, wherein the antibody light chain or the fragment thereof includes LCDR3, and the LCDR3 includes an amino acid sequence selected from that shown in SEQ ID NO: 82.
55. The antibody, the antigen binding fragment or the variant thereof according to any of embodiments 51-54, wherein the antibody light chain or the fragment thereof further includes framework regions L-FR1, L-FR2, L-FR3 and L-FR4.
56. The antibody, the antigen binding fragment or the variant thereof according to embodiment 55, wherein the framework regions are selected from the group consisting of human consensus framework sequences and human germline sequences.
57. The antibody, the antigen binding fragment or the variant thereof according to any of embodiments 55-56, wherein the C-terminus of the L-FR1 is directly or indirectly linked to the N-terminus of the LCDR1, and the L-FR1 includes an amino acid sequence selected from that shown in SEQ ID NO: 89.
58. The antibody, the antigen binding fragment or the variant thereof according to any of embodiments 55-57, wherein the L-FR2 is located between the LCDR1 and the LCDR2, and the L-FR2 includes an amino acid sequence selected from that shown in SEQ ID NO: 90.
59. The antibody, the antigen binding fragment or the variant thereof according to any of embodiments 55-58, wherein the L-FR3 is located between the LCDR2 and the LCDR3, and the L-FR3 includes an amino acid sequence selected from that shown in SEQ ID NO: 91.
60. The antibody, the antigen binding fragment or the variant thereof according to any of embodiments 55-59, wherein the N-terminus of the L-FR4 is directly or indirectly linked to the C-terminus of the LCDR3, and the L-FR4 includes an amino acid sequence selected from that shown in SEQ ID NO: 92.
61. The antibody, the antigen binding fragment or the variant thereof according to any of embodiments 51-60, wherein the antibody light chain or the fragment thereof includes a light chain variable region VL, and the light chain variable region VL includes an amino acid sequence selected from that shown in SEQ ID NO: 20.
62. The antibody, the antigen binding fragment or the variant thereof according to any of embodiments 51-61, wherein the antibody light chain or the fragment thereof further includes a human constant region and the human constant region includes a human Igλ constant region.

63. The antibody, the antigen binding fragment or the variant thereof according to any of embodiments 51-62, wherein the antibody light chain or the fragment thereof includes an amino acid sequence selected from that shown in SEQ ID NO: 23.
64. The antibody, the antigen binding fragment or the variant thereof according to any of embodiments 40-63, wherein the antibody includes an antibody heavy chain or a fragment thereof.
65. The antibody, the antigen binding fragment or the variant thereof according to embodiment 64, wherein the antibody heavy chain or the fragment thereof includes a HCDR1, and the HCDR1 includes an amino acid sequence selected from that shown in SEQ ID NO: 77.
66. The antibody, the antigen binding fragment or the variant thereof according to any of embodiments 64-65, wherein the antibody heavy chain or the fragment thereof includes a HCDR2, and the HCDR2 includes an amino acid sequence selected from that shown in SEQ ID NO: 78.
67. The antibody, the antigen binding fragment or the variant thereof according to any of embodiments 64-66, wherein the antibody heavy chain or the fragment thereof includes a HCDR3, and the HCDR3 includes an amino acid sequence selected from that shown in SEQ ID NO: 79.
68. The antibody, the antigen binding fragment or the variant thereof according to any of embodiments 64-67, wherein the antibody heavy chain of the fragment thereof further includes framework regions H-FR1, H-FR2, H-FR3 and H-FR4.
69. The antibody, the antigen binding fragment or the variant thereof according to embodiment 68, wherein the framework regions are selected from the group consisting of human consensus framework sequences and human germline sequences.
70. The antibody, the antigen binding fragment or the variant thereof according to any of embodiments 68-69, wherein the C-terminus of H-FR1 is directly or indirectly linked to the N-terminus of HCDR1, and the H-FR1 includes an amino acid sequence selected from that shown in SEQ ID NO: 84-85.
71. The antibody, the antigen binding fragment or the variant thereof according to any of embodiments 68-70, wherein the H-FR2 is located between the HCDR1 and the HCDR2, and the H-FR2 includes an amino acid sequence selected from that shown in SEQ ID NO: 86.
72. The antibody, the antigen binding fragment or the variant thereof according to any of embodiments 68-71, wherein the H-FR3 is located between the HCDR2 and the HCDR3, and the H-FR3 includes an amino acid sequence selected from that shown in SEQ ID NO: 87.
73. The antibody, the antigen binding fragment or the variant thereof according to any of embodiments 68-72, wherein the N-terminus of H-FR4 is directly or indirectly linked to the C-terminus of HCDR3, and the H-FR4 includes an amino acid sequence selected from that shown in SEQ ID NO: 88.
74. The antibody, the antigen binding fragment or the variant thereof according to any of embodiments 68-73, wherein the antibody heavy chain or the fragment thereof includes a heavy chain variable region VH, and the heavy chain variable region VH includes an amino acid sequence selected from that shown in SEQ ID NO: 18 or SEQ ID NO: 25.
75. The antibody, the antigen binding fragment or the variant thereof according to any of embodiments 64-74, wherein the antibody heavy chain or the fragment thereof further includes a human constant region, and the human constant region includes a human IgG constant region.
76. The antibody, the antigen binding fragment or the variant thereof according to embodiment 75, wherein the IgG constant region includes a human IgG1 constant region.
77. The antibody, the antigen binding fragment or the variant thereof according to any of embodiments 64-76, wherein the antibody heavy chain or the fragment thereof includes an amino acid sequence selected from that shown in SEQ ID NO: 21 or SEQ ID NO: 27.
78. The antibody, the antigen binding fragment or the variant thereof according to any of embodiments 40-77, wherein the CD137 protein includes a human CD137 protein.
79. A bispecific antibody which binds to a PD-L1 protein with a $K_D$ of $2\times10^{-9}$ M or less and binds to a CD137 protein at a $K_D$ of $8\times10^{-9}$ M or less.
80. The bispecific antibody according to embodiments 30 which includes a first targeting moiety that specifically binds to the PD-L1 protein, wherein the first targeting moiety includes the antibody, the antigen binding fragment or the variant thereof according to any of embodiments 1-39.
81. The bispecific antibody according to any of embodiments 30-31 which includes a second targeting moiety that specifically binds to the CD137 protein, wherein the second targeting moiety includes the antibody, the antigen binding fragment or the variant thereof according to any of embodiments 40-78.
82. The bispecific antibody according to any of embodiments 79-81 which includes a first polypeptide chain and a second polypeptide chain, wherein the first polypeptide chain includes the heavy chain variable region of the antibody that binds to the PD-L1 protein, the heavy chain variable region of the antibody that binds to the CD137 protein, and the light chain variable region of the antibody that binds to the CD137 protein; and the second polypeptide chain includes the light chain variable region of the antibody that binds to the PD-L1 protein.
83. The bispecific antibody according to embodiment 82, wherein in the first polypeptide chain, the heavy chain variable region of the antibody that binds to the PD-L1 protein is located at the N-terminus of the heavy chain variable region of the antibody that binds to the CD137 protein, and the heavy chain variable region of the antibody that binds to the CD137 protein is located at the N-terminus of the light chain variable region of the antibody that binds to the CD137 protein; alternatively, the heavy chain variable region of the antibody that binds to the PD-L1 protein is located at the N-terminus of the light chain variable region of the antibody that binds to the CD137 protein, and the light chain variable region of the antibody that binds to the CD137 protein is located at the N-terminus of the heavy chain variable region of the antibody that binds to the CD137 protein.
84. The bispecific antibody according to any of embodiments 82-83, wherein the light chain variable region of the antibody that binds to the CD137 protein and the heavy chain variable region of the antibody that binds to the CD137 protein in the first polypeptide chain constitute scFv.

85. The bispecific antibody according to any of embodiments 82-84, wherein the first polypeptide chain further includes a human IgG constant region, and the human IgG constant region is located at the C-terminus of the heavy chain variable region of the antibody that binds to the PD-L1 protein and located at the N-terminus of the light chain variable region of the antibody that binds to the CD137 protein; alternatively, the human IgG constant region is located at the C-terminus of the heavy chain variable region of the antibody that binds to the PD-L1 protein and located at the N-terminus of the heavy chain variable region of the antibody that binds to the CD137 protein.
86. The bispecific antibody according to any of embodiments 82-85, wherein the first polypeptide chain includes an amino acid sequence selected from the group consisting of SEQ ID NO: 30, SEQ ID NO: 43 and SEQ ID NO: 44.
87. The bispecific antibody according to any of embodiments 82-86, wherein the second polypeptide chain includes an amino acid sequence selected from the group consisting of SEQ ID NO: 15 and SEQ ID NO: 34.
88. One or more isolated nucleic acid molecules which encode the antibody, the antigen binding fragment or the variant thereof of any of embodiments 1-39, the antibody, the antigen binding fragment or the variant thereof of any of embodiments 40-78, or the bispecific antibody of any of embodiments 79-87.
89. A vector which includes the nucleic acid molecule according to embodiment 88.
90. A cell which includes the nucleic acid molecule according to embodiment 88 or the vector according to embodiment 89.
91. A method of preparing the antibody, the antigen binding fragment or the variant thereof of any of embodiments 1-39, the antibody, the antigen binding fragment or the variant thereof of any of embodiments 40-78, or the bispecific antibody of any of embodiments 79-87, including culturing the cell according to embodiment 90 under conditions that allow expression of the antibody, the antigen binding fragment or the variant thereof of any of embodiments 1-39, the antibody, the antigen binding fragment or the variant thereof of any of embodiments 40-78, or the bispecific antibody of any of embodiments 79-87.
92. A pharmaceutical composition which includes the antibody, the antigen binding fragment or the variant thereof of any of embodiments 1-39, the antibody, the antigen binding fragment or the variant thereof of any of embodiments 40-78, or the bispecific antibody of any of embodiments 79-87, the nucleic acid molecule of embodiment 88, the vector of embodiment 89 and/or the cell of embodiments 90, and optionally a pharmaceutical acceptable adjuvant.
93. Use of the antibody, the antigen binding fragment or the variant thereof of any of embodiments 1-39, the antibody, the antigen binding fragment or the variant thereof of any of embodiments 40-78, or the bispecific antibody of any of embodiments 79-87, the nucleic acid molecule of embodiment 88, the vector of embodiment 89, the cell of embodiment 90 and/or the pharmaceutical composition of embodiment 92 in manufacture of a drug for relieving or treating tumors.
94. Use according to embodiment 93, wherein the tumor includes colon cancer.
95. A method of inhibiting the binding of PD-L1 protein to PD-1 protein, including administering the antibody, the antigen binding fragment or the variant thereof of any of embodiments 1-39, the antibody, the antigen binding fragment or the variant thereof of any of embodiments 40-78, or the bispecific antibody of any of embodiments 79-87, the nucleic acid molecule of embodiment 88, the vector of embodiment 89, the cell of embodiment 90 and/or the pharmaceutical composition of embodiments 92.
96. A method of enhancing the function of T cells, including administering the antibody, the antigen binding fragment or the variant thereof of any of embodiments 1-39, the antibody, the antigen binding fragment of the variant thereof of any of embodiments 40-78, of the bispecific antibody of any of embodiments 79-87, the nucleic acid molecule of embodiment 88, the vector of embodiment 89, the cell of embodiment 90 and/or the pharmaceutical composition of embodiment 92.

Not to be limited by any theory, the following examples are only to illustrate the working methods of the apparatus, method and system of the present application, but not to limit the scope of the present application invention.

EXAMPLES

Example 1. Screening of Anti-PD-L1 Antibody by Use of Phage Antibody Library Human PD-L1-Fc protein (Origincell Therapeutics Co., Ltd.) as antigen was used to sort the phage natural human antibody library (Origincell Therapeutics Co., Ltd.). The ELISA tube was coated with a CBS buffer containing 20 μg/ml (the first and the second rounds) or 10 μg/ml (the third and the fourth rounds) of PD-L1 protein at 4° C. overnight. The tube was then washed with a PBS buffer. 10% skimmed milk powder was added to block the ELISA tube, and then 1 ml of blocked phage was added and incubated at room temperature (20±5° C.) for 1 hour. After washing thoroughly with PBST, 800 μl of a Gly-HCl buffer solution at pH 2.2 was added for elution, and then 400 μl of a Tris-HCl buffer solution at pH 8.0 was added immediately for neutralization. Then, the mixture was added to 20 ml of *E. coli* SS320 in the logarithmic growth phase with an OD value of about 0.8, mixed well and stood at 37° C. for 1 hour. 500 μl of microbial solution was taken for measuring the phage titer and glycerin was used to protect the microbials, and the remaining microbial solution was used to coat the plate and cultivated at 37° C. overnight. On the next day, the bacteria on the plate were proportionally inoculated to 80 ml of 2YT-Amp medium, so that the microbial solution has an OD value of 0.2, and cultured for several hours. When the OD value reached 0.8, 160 μl of helper phage was added, mixed well, and stood at 37° C. for 1 hour. Then, IPTG and Kan antibiotics were added and cultured with shaking at 250 rpm at 30° C. overnight. Subsequently, the supernatant was collected for precipitation of the phage by PEG/NaCl solution, which was re-suspended in 1.5 ml of PBS buffer for enrichment screening.

96-well ELISA plates were coated with solutions containing 1 μg/ml of human PD-L1-Fc protein (Origincell Therapeutics Co., Ltd.) and mouse PD-L1-Fc protein (M5251, purchased from ACROBiosystems Inc.) at 4° C. overnight. The plate was then blocked with 10% skimmed milk powder at non-specific binding sites. After thorough washing, the monoclonal phage supernatant was taken and added to the 96-well plates and incubated at 37° C. for 2 hours. After thorough washing, HRP-labeled anti-M13 antibody (27-9421-01, GE healthcare) was added to each well, and reacted at 37° C. for 45 minutes. After washing thoroughly, TMB was added to each well for color development. After reacting at room temperature (20±5° C.) for 5-10 minutes, sulfuric acid was added to each well to stop the reaction. A microplate reader is used to measure the OD value of each well at 450 nm.

A phage antibody clone 1B10 which could specifically bind to both human PD-L1 and mouse PD-L1 was identified by ELISA. Sequencing results show that the nucleotide sequence encoding the heavy chain variable region VH of the phage antibody 1B10 is shown in SEQ ID NO: 1, and the amino acid sequence of the heavy chain variable region VH of the phage antibody 1B10 is shown in SEQ ID NO: 2; the nucleotide sequence encoding the light chain variable region VL of the phage antibody 1B10 is shown in SEQ ID NO: 3, and the amino acid sequence of the light chain variable region VL of the phage antibody 1B10 is shown in SEQ ID NO: 4.

Example 2. Expression and Purification of Anti-PD-L1 Fully Human Intact Antibody A primer was designed for PCR amplification of the VH of the phage antibody 1B10, and the PCR product was cloned by recombination into the pCMV-IgG1NDL vector which was double digested with AgeI and SalI. A design primer was designed for PCR amplification of the VL of the phage antibody 1B10, and the PCR product was cloned by recombination into a pCMV-λ vector which was double digested with AgeI and BsiWI. After sequencing exactly, the heavy chain and the light chain expression vectors were co-transfected into 293F cells for transient expression, and purified by ProteinA column to obtain an intact IgG1λ antibody of the phage antibody 1B10. This anti-PD-L1 fully human antibody was named YN-002.

The sequencing results show that the nucleotide sequence of the VH encoding the antibody YN-002 is shown in SEQ ID NO: 1, and the amino acid sequence of VH of the antibody YN-002 is shown in SEQ ID NO: 2. The nucleotide sequence of VL encoding the antibody YN-002 is shown in SEQ ID NO: 3, and the amino acid sequence of VL of the antibody YN-002 is shown in SEQ ID NO: 4. The nucleotide sequence of the heavy chain encoding the antibody YN-002 is shown in SEQ ID NO: 5, and the amino acid sequence of the heavy chain of YN-002 is shown in SEQ ID NO: 6. The nucleotide sequence encoding the light chain of the antibody YN-002 is shown in SEQ ID NO: 7, and the amino acid sequence of light chain of the antibody YN-002 is shown in SEQ ID NO: 8.

Example 3. Germline Version of Anti-PD-L1 Fully Human Antibody YN-002

By comparing the antibody YN-002 heavy chain immunoglobulin sequence with the known human germline immunoglobulin heavy chain sequence, it was confirmed that the antibody YN-002 heavy chain used the VH segment from human germline IGHV1-69*09, the D segment from human germline IGHD5-18*01, and JH segment from human germline IGHJ4*02.

By comparing the light chain immunoglobulin sequence of the antibody YN-002 with the known human germline immunoglobulin light chain sequence, it was confirmed that the light chain of the antibody YN-002 used the VL segment from human germline IGLV2-14*01, and JL segment from human germline IGLJ2*01.

The sequence of the CDR region of the antibody YN-002 was analyzed by the Kabat system (see FIG. 1).

The sequencing results show that the amino acid sequences of LCDR1-3 of the antibody YN-002 are shown in SEQ ID NO: 54, SEQ ID NO: 60 and SEQ ID NO: 63, respectively; and the amino acid sequences of HCDR1-3 are shown in SEQ ID NO: 46, SEQ ID NO: 48 and SEQ ID NO: 50, respectively.

To minimize the immunogenicity of the antibody YN-002, some amino acid residues could be mutated back to the germline sequence. The antibody YN-003 is a germline version of the antibody YN-002, which is prepared by mutating one amino acid in the FR1 region of the YN-002 heavy chain variable region back to the germline sequence, and mutating 1 amino acid in the FR2 region and 6 amino acids in the FR3 region in the YN-002 light chain variable region back to the germline sequence (see FIG. 1). The heavy chain expression vector of the anti-PD-L1 fully human antibody YN-003 is obtained by site-directed mutagenesis using a mutation kit (Tiangen Point Mutation Kit, KM101) based on the above-constructed YN-002 heavy chain expression plasmid. The YN-003 light chain expression vector is obtained by site-directed mutagenesis using a mutation kit (Tiangen Point Mutation Kit, KM101) based on the YN-002 light chain expression plasmid.

The amino acid sequence of the antibody YN-003 VH is shown in SEQ ID NO: 9, which can be obtained by mutating one amino acid residue in the amino acid sequence of the antibody YN-002 VH. The nucleotide sequence encoding YN-003 VH is shown in SEQ ID NO: 10. The amino acid sequence of the antibody YN-003 VL is shown in SEQ ID NO: 11, which can be obtained by mutating 7 amino acid residues in the amino acid sequence of the antibody YN-002 VL, and the nucleotide sequence corresponding to YN-003VL is shown in SEQ ID NO: 12. The amino acid sequence of the heavy chain of the antibody YN-003 is shown in SEQ ID NO: 13; the nucleotide sequence encoding the heavy chain of YN-003 is shown in SEQ ID NO: 14; the amino acid sequence of the light chain of the antibody YN-003 is shown in SEQ ID NO: 15; and the nucleotide sequence encoding the light chain of the antibody YN-003 is shown in SEQ ID NO: 16.

For the expression and purification of the YN-003 antibody, please refer to the steps of expressing and purifying the YN-002 antibody in Example 2.

Example 4. Test of Binding Affinity of Anti-PD-L1 Antibody

The binding affinity of the antibody YN-002 and the antibody YN-003 to the recombinant human, Macaca fascicularis, mouse, and canine PD-L1 proteins was measured by a molecular interaction analyzer (Octet RED384, purchased from Pall ForteBio Analytics Co., Ltd.). The following proteins were labeled with biotin (EZ-Link Sulfo-NHS-LC-Biotin, Pierce, 21327): recombinant human PD-L1-Fc, recombinant Macaca fascicularis PD-L1-Fc (90251-C02H, purchased from Sino Biological Inc.), recombinant mouse PD-L1-Fc (M5251, purchased from ACROBiosystems Inc.), recombinant dog PD-L1-Fc (70110-D02H, purchased from Sino Biological Inc.). The antigen-antibody binding kinetics were analyzed by a biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. A biotin-coupled antigen protein with a concentration of 50 nM was fixed with the SA sensor (Pall ForteBio Analytics Co., Ltd.), and bound at 1500 rpm for 10 minutes; then it was bound with the double-diluted antibody solution at 1500 rpm for 10 minutes; and finally dissociated at 1500 rpm for 10 minutes. The obtained results would be analyzed by Octet Data Analysis 9.0 software (Pall ForetBio Analytics Co., Ltd.) to give the $K_D$, $K_{on}$ (1/Ms) and $K_{off}$ (1/s).

The results of the measured binding affinity of the anti-PD-L1 antibodies YN-002 to YN-3 are shown in Tables 1-4.

TABLE 1

Binding Affinity of PD-L1 Antibody to Human PD-L1-Fc

| | Human PD-L1-Fc-Biotin | | |
|---|---|---|---|
| Antibody | $k_{on}$ (1/Ms) | $k_{off}$ (1/s) | $K_D$ (M) |
| YN-002 | $6.69 \times 10^5$ | $5.94 \times 10^{-4}$ | $8.88 \times 10^{-10}$ |
| YN-003 | $1.50 \times 10^6$ | $6.11 \times 10^{-4}$ | $4.08 \times 10^{-10}$ |

TABLE 2

Binding Affinity of PD-L1 Antibody to Mouse PD-L1-Fc

| | Mouse PD-L1-Fc-Biotin | | |
|---|---|---|---|
| Antibody | $k_{on}$ (1/Ms) | $k_{off}$ (1/s) | $K_D$ (M) |
| YN-002 | $9.77 \times 10^5$ | $1.68 \times 10^{-3}$ | $1.72 \times 10^{-9}$ |
| YN-003 | $1.03 \times 10^6$ | $9.97 \times 10^{-4}$ | $9.96 \times 10^{-10}$ |

TABLE 3

Binding Affinity of PD-L1 Antibody to Macaca Fascicularis PD-L1-Fc

| | Macaca Fascicularis PD-L1-Fc-Biotin | | |
|---|---|---|---|
| Antibody | $k_{on}$ (1/Ms) | $k_{off}$ (1/s) | $K_D$ (M) |
| YN-002 | $1.77 \times 10^6$ | $1.90 \times 10^{-3}$ | $1.07 \times 10^{-9}$ |
| YN-003 | $2.08 \times 10^6$ | $1.36 \times 10^{-3}$ | $6.54 \times 10^{-10}$ |

TABLE 4

Binding Affinity of PD-L1 Antibody to Dog PD-L1-Fc

| | Dog PD-L1-Fc-Biotin | | |
|---|---|---|---|
| Antibody | $k_{on}$ (1/Ms) | $k_{off}$ (1/s) | $K_D$ (M) |
| YN-002 | $1.02 \times 10^6$ | $7.59 \times 10^{-4}$ | $7.43 \times 10^{-10}$ |
| YN-003 | $8.64 \times 10^5$ | $5.14 \times 10^{-4}$ | $5.94 \times 10^{-10}$ |

Example 5. PD-L1 Antibody Inhibits the Binding of Human PD-L1 and Human PD-1

The human PD-1-Fc protein (ACROBiosystems Inc., H5257) was labeled with biotin (EZ-Link Sulfo-NHS-LC-Biotin, Pierce, 21327). The human PD-1-Fc labeled with a subsaturated concentration of biotin was added into $1\times10^6$/ml of the CHO cells that stably expressed human PD-L1, and then each antibody diluted in five-fold ratio was added, mixed well and incubated (4° C. 1 hr). After cell washing, Streptavidin R-PE Conjugate (life technology. SA10041) was added and incubated (4° C., 30 min). After cell washing, the fluorescence intensity was detected by a flow cytometer (Intellicyt iQue Screener). The results are shown in FIG. 2: both YN-002 and YN-003 can effectively inhibit the binding of human PD-1 to CHO cells expressing human PD-L1.

Example 6. PD-L1 Antibody Inhibits the Binding of Macaca Fascicularis PD-L1 to Macaca Fascicularis PD-1

The capacity of anti-PD-L1 antibodies YN-002 and YN-003 for blocking the binding of Macaca fascicularis PD-L1-Fc (Sino Biological Inc., 90251-C02H) to Macaca fascicularis PD-1-Fc (Sino Biological Inc., 90311-C02H) was assessed by the Octet RED384 instrument ((Pall ForteBio Analytics Co., Ltd.). First, the Macaca fascicularis PD-1-Fc was labeled with biotin (EZ-Link Sulfo-NHS-LC-Biotin, Pierce, 21327). The binding kinetic analysis of PD-L1 antibody for inhibiting the binding of Macaca fascicularis PD-L1 to Macaca fascicularis PD-1 was performed by the biofilm interference (BLI) technology, using the fortebio octet RED384 instrument (PALL) molecular interaction analyzer (both the antigen and the antibody were diluted with 0.1% BSA and 0.02% Tween 20 in a PBS buffer). A 100 nM biotin-coupled recombinant human PD-1-Fc was fixed with the SA sensor at 1500 rpm/min and bound for 10 min. The Macaca fascicularis PD-L1 at a final concentration of 75 nM was mixed with a three-fold diluted antibody solution, incubated for 60 minutes and then combined on the machine for 10 minutes at 1500 rpm/min, and finally dissociated for 10 minutes at 1500 rpm/min. The obtained results will be subject to data analysis by Octet Data Analysis 9.0 software (Pall ForteBio Analytics Co., Ltd.). The results are shown in FIG. 3: both YN-002 and YN-003 can effectively inhibit the binding of Macaca fascicularis PD-L1-Fc to Macaca fascicularis PD-1-Fc.

Example 7. PD-L1 Antibody Inhibiting the Binding of Mouse PD-L1 to Mouse PD-1

Figure 4:
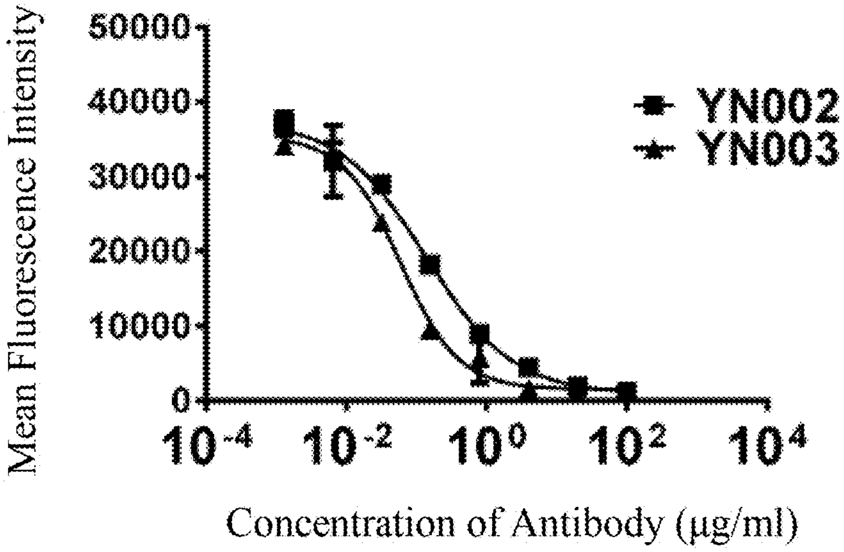
FIG. 4 shows the results of the PD-L1 antibody of the present application inhibiting the binding of the mouse PD-L1 to the mouse PD-1.

Mouse PD-1-Fc (ACROBiosystems Inc., M5259) was labeled with biotin (EZ-Link Sulfo-NHS-LC-Biotin, Pierce, 21327), mouse PD-1-Fc labeled with a subsaturated concentration of biotin was added into $1\times10^6$/ml of CHO cells that stably expressed mouse PD-L1, and then each antibody diluted in five-fold ratio was added, mixed well and incubated (4° C., 1 hr). After cell washing. Streptavidin R-PE Conjugate (life technology, SA10041) was added and incubated (4° C. 30 min). After cell washing, the fluorescence intensity was detected by flow cytometer (Intellicyt iQue Screener). The results are shown in FIG. 4: both YN-002 and YN-003 can effectively inhibit the binding of mouse PD-1 to the CHO cells expressing mouse PD-L1.

Example 8. Studies of Antitumor Effect of Anti-PD-L1 Monoclonal Antibody in Colon Cancer-Bearing Mice On Day 0, 6-8 week old C57BL/6 female mice were subcutaneously inoculated with $3\times10^6$ MC38 mouse colorectal cancer cells (Shanghai Linyuan Biological Technology Co., Ltd.). On Day 3, the mice were evenly divided into 7 groups with 8-9 mice in each group. The tumor-bearing mice in each group were intraperitoneally injected with the human antibody IgG-Fc protein (10) mg/kg, twice per week, two weeks in total). YN-003 antibody (10 mg/kg, twice per week, two weeks in total), Atezolizumab (10 mg/kg, twice per week, two weeks in total), respectively. The mice in each group were regularly observed for the change of body weight and tumor size. The experimental results show: as compared with the control IgG1-Fc, both YN-003 and Atezolizumab can effectively inhibit the tumor growth, wherein the antitumor effect of YN-003 is more significant (FIG. 5).

Example 9. Screening Anti-CD137 Antibody by Phage Antibody Library

The CD137 protein (purchased from Sino Biological Inc.) was used as an antigen to sort the phage natural human antibody library (Origincell Therapeutics Co., Ltd.). The ELISA tube was coated with a CBS buffer containing 20 μg/ml (the first and the second rounds) or 10 μg/ml (the third and the fourth rounds) of CD137 protein at 4° C. overnight. The tube was then washed with a PBS buffer. 10% skimmed milk powder was added to block the ELISA tube, and then 1 ml of blocked phage was added and incubated at room temperature (20±5° C.) for 1 hour. After washing thoroughly with PBST, 800 μl of a Gly-HCl buffer solution at pH 2.2 was added for elution, and then 400 μl of a Tris-HCl buffer solution at pH 8.0 was added immediately for neutralization. Then, the mixture was added to 20 ml of *E. coli* SS320 in the logarithmic growth phase with an OD value of about 0.8, mixed well and stood at 37° C. for 1 hour. 500 μl of microbial solution was taken for measuring the phage titer and glycerin was used to protect the microbials, and the remaining microbial solution was used to coat the plate and cultivated at 37° C. overnight. On the next day, the bacteria on the plate were proportionally inoculated to 80 ml of 2YT-Amp medium, so that the microbial solution has an OD value of 0.2, and cultured for several hours. When the OD value reached 0.8, 160 μl of helper phage was added, mixed well, and stood at 37° C. for 1 hour. Then, IPTG and Kan antibiotics were added and cultured with shaking at 250 rpm at 30° C. overnight. Subsequently, the supernatant was collected for precipitation of the phage by PEG/NaCl solution, which was re-suspended in 1.5 ml of PBS buffer for enrichment screening.

96-well ELISA plates were coated with solutions containing 1 μg/ml of human CD137 protein at 4° C. overnight. The plate was then blocked with 10% skimmed milk powder at non-specific binding sites. After thorough washing, the monoclonal phage supernatant was taken and added to the 96-well plates and incubated at 37° C. for 2 hours. After thorough washing, HRP-labeled anti-M13 antibody (27-9421-01, GE healthcare) was added to each well, and reacted at 37° C. for 45 minutes. After washing thoroughly, TMB was added to each well for color development. After reacting at room temperature (20±5° C.) for 5-10 minutes, sulfuric acid was added to each well to stop the reaction. A microplate reader is used to measure the OD value of each well at 450 nm.

A phage antibody clone 1A6 which could specifically bind to human CD137 was identified by ELISA, and the VH and VL gene sequences were obtained by sequencing. The sequencing results showed that the nucleotide sequence encoding the VH of the phage antibody 1A6 is shown in SEQ ID NO: 17, the amino acid sequence of the VH of the phage antibody 1A6 is shown in SEQ ID NO: 18; the nucleoside acid sequence encoding the VL of the phage antibody 1A6 is shown in SEQ ID NO: 19, and the amino acid sequence of VL of the phage antibody 1A6 is shown in SEQ ID NO: 20.

Example 10. Expression and Purification of Anti-CD137 Fully Human Intact Antibody A primer was designed for the PCR amplification of the VH of phage antibody 1A6. The PCR product was cloned by recombination into the pCMV-IgG2 vector double digested with AgeI and SalI. A primer was designed for the PCR amplification of the VL of phage antibody 1A6, and the PCR product was cloned by recombination into pCMV-λ vector digested with AgeI and BsiWI. After correct sequencing, the heavy chain and the light chain expression vectors were co-transfected into 293F cells for transient expression, and purified by ProteinA column. The intact IgG2, λ antibody of 1A6, the anti-CD137 fully human antibody, was named YN-005.

The sequencing results showed that the amino acid sequence of the antibody YN-005 VH is shown in SEQ ID NO: 18, the nucleotide sequence encoding the antibody YN-005 VH is shown in SEQ ID NO: 17; and the amino acid sequence of the antibody YN-005 VL is shown in SEQ ID NO: 20, and the nucleotide sequence encoding the antibody YN-005 VL is shown in SEQ ID NO: 19. The amino acid sequence of the heavy chain of the antibody YN-005 is shown in SEQ ID NO: 21, the nucleotide sequence encoding the heavy chain of the antibody YN-005 is shown in SEQ ID NO: 22; the amino acid sequence of the light chain of the antibody YN-005 is shown in SEQ ID NO: 23, and the nucleotide sequence encoding the light chain of the antibody YN-005 is shown in SEQ ID NO: 24.

Example 11. Germline Version of Anti-CD137 Fully Human Antibody YN-005

By comparing the antibody YN-005 heavy chain immunoglobulin sequence with the known human germline immunoglobulin heavy chain sequence, it was confirmed that the antibody YN-005 heavy chain utilized the VH segment from human germline IGHV3-23*04, the D segment from human germline IGHD7-27*01 and the JH segment from human germline IGHJ3*02.

By comparing the YN-005 light chain immunoglobulin sequence with the known human germline immunoglobulin light chain sequence, it was confirmed that the antibody YN-005 light chain utilized the VL segment from human germline IGLV1-44*01 and the JL segment from human germline IGLJ1*01.

The Kabat system was used to analyze the sequence of the CDR region of the antibody YN-005 (see FIG. 6), and the sequencing results show that the amino acid sequence of HCDR1-3 of the antibody YN-005 is shown in SEQ ID NO: 77. SEQ ID NO: 78 and SEQ ID NO: 79, respectively. The amino acid sequence of the LCDR1-3 of the antibody YN-005 is shown in SEQ ID NO: 80, SEQ ID NO: 81 and SEQ ID NO: 82, respectively.

In order to minimize the immunogenicity of the antibody YN-005, some amino acid residues can be mutated back to the germline sequence. The antibody YN-006 is a germline version of the antibody YN-005, which is prepared by mutating one amino acid in the FR1 region in the YN-005 heavy chain variable region back to the germline sequence (see FIG. 6). The heavy chain expression vector of the anti-CD137 fully human antibody YN-006 is obtained by site-directed mutagenesis using a mutation kit (Tiangen Point Mutation Kit, KM101) based on the above-constructed heavy chain express plasmid of YN-005.

Sequencing shows that the amino acid sequence of the antibody YN-006 VH is shown in SEQ ID NO: 25, and the nucleotide sequence encoding the YN-006 VH is shown in SEQ ID NO: 26. The amino acid sequence of the antibody YN-006 VL is shown in SEQ ID NO: 20, and the nucleotide sequence encoding the YN-006 VL is shown in SEQ ID NO: 19. The amino acid sequence of the antibody YN-006 heavy chain is shown in SEQ ID NO: 27; the nucleotide sequence encoding the antibody YN-006 heavy chain is shown in SEQ ID NO: 28; and the amino acid sequence of the antibody YN-006 light chain is shown in SEQ ID NO: 23, and the nucleotide sequence encoding the YN-006 light chain is shown in SEQ ID NO: 24.

For the expression and purification of the YN-006 antibody, please refer to the specific steps of expressing and purifying YN-005 antibody in Example 9.

Example 12. Determination of Binding Affinity of Anti-CD137 Antibody

The binding affinity of the antibody YN-005 and the antibody YN-006 to the recombinant human CD137-His protein (Origincell Therapeutics Co., Ltd.) was measured by a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted recombinant CD137-His protein antigen solution (100, 50, 25, 12.5, 6.25, 3.125, 1.56 nM) at 1500 rpm for 5 minutes; and finally dissociated at 1500 rpm for 10 minutes. The AHC sensor is regenerated by glycine pulses and then reused. The obtained results would be analyzed by Octet Data Analysis 9.0 software (Pall ForteBio Analytics Co., Ltd.) to give the $K_D$, $K_{on}$ (1/Ms) and $K_{off}$ (1/s). The measured results of the binding affinity of the CD137 antibodies YN-005 and YN-006 are shown in Table 5.

TABLE 5

Affinity of CD137 Antibody to Human CD137-His

| | CD137-His | | |
|---|---|---|---|
| Antibody | $K_{on}$ (1/Ms) | $K_{off}$ (1/s) | $K_D$ (M) |
| YN-005 | $9.38 \times 10^4$ | $4.55 \times 10^{-5}$ | $4.85 \times 10^{-10}$ |
| YN-006 | $9.68 \times 10^4$ | $1.33 \times 10^{-5}$ | $1.37 \times 10^{-10}$ |

Figure 7:
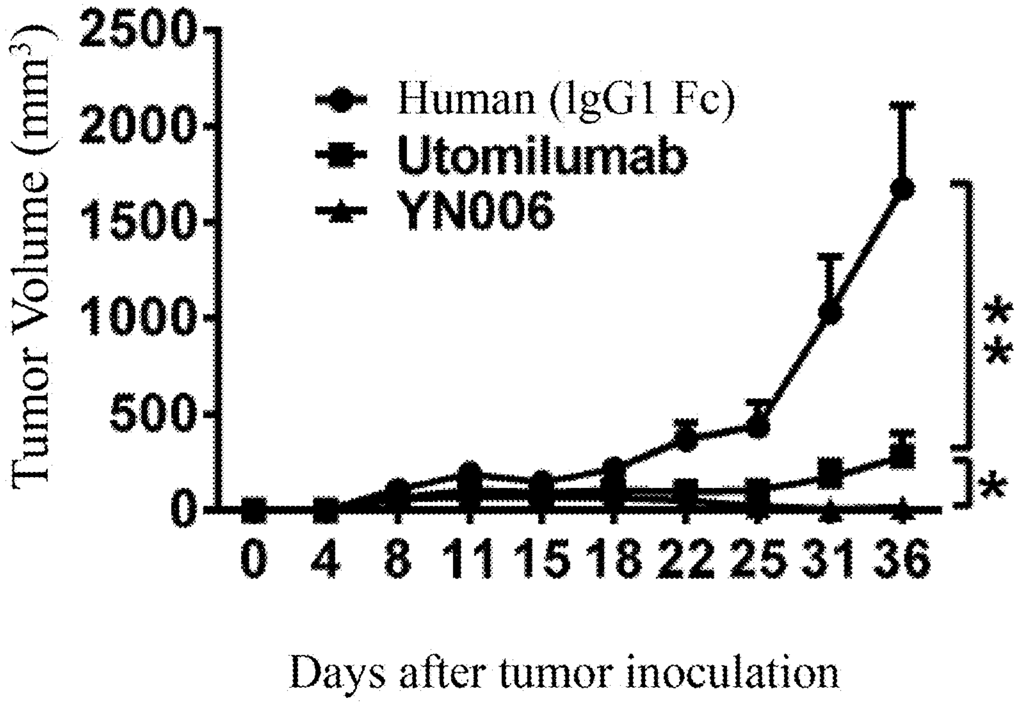
FIG. 7 shows the effect of the CD137 antibody of the present application on the MC38 tumor growth in C57BL/6 female mouse with human CD137 gene knocked-in (*, P<0.05; **, P<0.01; Unpaired t-est).

Example 13. Studies of Antitumor Effect of CD137 Monoclonal Antibody in Colon Cancer-Bearing Mice On Day 0, 6-8 week old C57BL/6 female mice with human CD137 gene (B-hTNFRSF9) (4-1BB) mice, purchased from Beijing BioCytogen Co., Ltd.) were subcutaneously inoculated with $1.5\times10^6$ MC38 mouse colorectal cancer. On Day 3, the mice were evenly divided into 3 groups with 7 mice in each group. The tumor-bearing mice in each group were intraperitoneally injected with the human antibody IgG-Fc protein (3 mg/kg, twice per week, two weeks in total), CD137 antibody YN-006 antibody (3 mg/kg, twice per week, two weeks in total), and CD137 antibody Utomilumab (3 mg/kg, twice per week, two weeks in total), respectively. The mice in each group were regularly observed for the change of body weight and tumor size. The experimental results show: as compared with the control IgG1-Fc, both YN-006 and Utomilumab can effectively inhibit the tumor growth, and it is worth noting that the antitumor effect of YN-006 is more significant than Utomilumab (e.g., as shown in FIG. 7).

Example 14. Construction of Anti-PD-L1/CD137 Bispecific Antibody YN-007

The first polypeptide gene of the anti-PD-L1/CD137 bispecific antibody YN-007 was constructed by a molecular cloning method, such as, Overlap PCR, Site-directed Mutation, or the like using the heavy chain gene of the anti-PD-L1 antibody YN-003 and the heavy chain and the light chain genes of the anti-human CD137 antibody YN-006, and cloned by combination into the pCMV-IgG1AEM vector double digested with AgeI and BamHI to construct the expression vector of the first polypeptide of YN-007.

The second polypeptide gene of YN-007 is the same as that of the light chain gene of YN-003. The expression vector of the second polypeptide of YN-007 is the above-constructed expression vector of the light chain of YN-003.

After correct sequencing, the expression vectors of the first polypeptide and the second polypeptide were co-transfected into 293F cells for transient expression, and purified by Protein A Column to obtain the anti-PD-L1/CD137 bispecific antibody YN-007.

The nucleotide sequence encoding the first polypeptide of the antibody YN-007 is shown in SEQ ID NO: 29, and the amino acid sequence of the first polypeptide of the antibody YN-007 is shown in SEQ ID NO: 30; the nucleotide sequence encoding the second polypeptide of the antibody YN-007 is shown in SEQ ID NO: 16, and the amino acid sequence of the second polypeptide of the antibody YN-007 is shown in SEQ ID NO: 15.

Example 15. Determination of Binding Affinity of Anti-PD-L1/CD137 Bispecific Antibody YN-007

The binding affinity of the anti-PD-L1/CDI37 bispecific antibody YN-007 to the recombinant human PD-L1-Fc protein and the recombinant mouse PD-L1-Fc was measured by a molecular interaction analyzer (Octet RED384, purchased from Pall ForteBio Analytics Co., Ltd.). The recombinant human PD-L1-Fc protein and the recombinant mouse PD-L1-Fc were labeled with biotin (EZ-Link Sulfo-NHS-LC-Biotin, Pierce, 21327). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. A biotin-coupled antigen protein with a concentration of 50 nM was fixed with the SA sensor (Pall ForteBio Analytics Co., Ltd.), and bound at 1500 rpm for 10 minutes; then it was bound with the double-diluted YN-007 antibody solution at 1500 rpm for 10 minutes; and finally dissociated at 1500 rpm for 10 minutes. The obtained results would be analyzed by Octet Data Analysis 9.0 software (Pall ForteBio Analytics Co., Ltd.) to give the $K_D$, $K_{on}$ (1/Ms) and $K_{off}$ (1/s).

The measured results of the binding affinity of YN-007 to human PD-L1-Fc are shown in Table 6.

The measured results of the binding affinity of YN-007 to mouse PD-L1-Fc were shown in Table 7.

TABLE 6

| Binding Affinity of Anti-PD-L1/CD137 Bispecific Antibody YN-007 to Human PD-L1-Fc. | | | |
|---|---|---|---|
| | Human PD-L1-Fc-Biotin | | |
| Antibody | $k_{on}$ (1/Ms) | $k_{off}$ (1/s) | $K_D$ (M) |
| YN-007 | $1.13 \times 10^6$ | $5.92 \times 10^{-4}$ | $5.25 \times 10^{-10}$ |

TABLE 7

| Binding Affinity of Anti-PD-L1/CD137 Bispecific Antibody YN-007 to Mouse PD-L1-Fc | | | |
|---|---|---|---|
| | Mouse PD-L1-Fc-Biotin | | |
| Antibody | $k_{on}$ (1/Ms) | $k_{off}$ (1/s) | $K_D$ (M) |
| YN-007 | $8.1 \times 10^5$ | $1.09 \times 10^{-3}$ | $1.34 \times 10^{-9}$ |

The binding affinity of the anti-PD-L1/CD137 bispecific antibody YN-007 to the recombinant human CD137-His protein was measured by a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted recombinant human CD137-His protein antigen solution (100, 50, 25, 12.5, 6.25, 3.125, 1.56 nM) at 1500 rpm for 5 minutes; and finally dissociated at 1500 rpm for 10 minutes. The AHC sensor was regenerated by glycine pulses and then reused. The obtained results would be analyzed by Octet Data Analysis 9.0 software (Pall ForteBio Analytics Co., Ltd.) to calculate the binding strength between the antigen and the antibody, to give the $K_D$, $K_{on}$ (1/Ms) and $K_{off}$ (1/s).

The measured results of the binding affinity of anti-PD-L1/CD137 bispecific antibody YN-007 to human CD137 are shown in Table 8.

TABLE 8

| Binding Affinity of Anti-PD-L1/CD137 Bispecific Antibody YN-007 to Human CD137-His | | | |
|---|---|---|---|
| | Human CD137-His | | |
| Antibody | $K_{on}$ (1/Ms) | $K_{off}$ (1/s) | $K_D$ (M) |
| YN-007 | $8.96 \times 10^4$ | $9.83 \times 10^{-5}$ | $1.1 \times 10^{-9}$ |

Example 16. Affinity Maturation of PD-L1 Antibody YN-003

A primer was designed to construct the single-chain antibody (ScFv) gene of the PD-L1 antibody YN-003 by overlapping PCR, and cloned into the pDF phagemid vector, and denoted as PDF-YN-003 ScFv. The pDF-YN-003 ScFv was used as a template to design a degenerate primer to randomize 6 CDR regions (including some amino acid residues in the CDR regions and individual amino acid residues in the FR regions adjacent to the CDR regions) of the antibody YN-003 by overlapping PCR, respectively (as shown in FIG. 8).

The CDR region-randomized scFv gene fragments obtained by overlapping PCR were double digested with BssHII and NheI, and then ligated with the pDF phagemid vector double digested by BssHII and NheI. 1 μg of the ligation product was electroporated into TG1 electro-competent cells, and coated onto a 2YT+AG plate after multiple dilutions. On the next day, the lawn was scraped from the plate, and expanded to 300 ml of 2YT+Amp medium. It was cultured at 37° C. to an OD of about 0.8. The helper phage was added and mixed well, stood for 1 hour, and IPTG with a final concentration of 1 mM and 50 μg/ml of Kana were added and shaken at 30° C. overnight. On the next day, the supernatant was collected by centrifugation, and filtered with 0.45 filter. ⅕ volume of PEG-NaCl was added to precipitate phage, and centrifuged to collect the precipitate. ⅒ volume of PBS was used to resuspend the precipitate, and OD260 was measured to calculate the phage pfu. The product was stored at 4° C. The phage antibody library can be used directly for later panning.

The human PD-L1-His protein (Origincell Therapeutics Co., Ltd.) as the antigen was used to sort the above phage antibody library. In ELISA tubes, a CBS buffer was used to coat the antigen PD-L1 (1 ml) with a concentration of 100 nM (the first and the second rounds) or 5 nM (the third round) at 4° C. overnight. On the next day, 2 ml of PBS buffer containing 10% skimmed milk powder was used to block the tube. 1 ml of the blocked phage was added into the tube and incubated for 1 hr at room temperature; washed with PBST for 20 times (the first round), 50 times (the second round) or 100 times (the third round). 800 μl of Gly-HCl buffer (pH 2.2) was added for elution, and 400 μl of Tris-HCl buffer (pH 8.0) was immediately added for neutralization. It was added to 20 ml of *E. coli* TG1 with logarithmic growth phase OD of about 0.8, mixed well and stood at 37° C. for 1 hr. 500 μl was taken for determining the phage titer and glycerol was used to protect the microbials. The remaining microbial liquid was spread on the plate and incubated at 37° C. in the incubator overnight. On the next day, the microbials on the plate were scraped and inoculated in 80 ml of 2YT-Amp medium at a certain proportion to allow the OD to be 0.2. The mixture were incubated for several hours until the OD reached 0.8. 160 μl of helper phage was added, mixed well and stood at 37° C. for 1 h. IPTG and Kan antibiotics were added, and incubated under shaking at 250 rpm at 30° C. overnight. The supernatant was collected and treated with PEG/NaCl solution for precipitating the phages, which were resuspended in 1.5 ml of PBS buffer. The resuspended phage was used for the next round of enrichment screening. After 3 rounds of sorting, a significant enrichment was observed. The sorted phage antibody clones were identified by ELISA: human PD-L1-His protein was coated on a 96-well ELISA plate at a concentration of 1 μg/ml at 4° C. overnight. Then, the non-specific binding sites were blocked with 10% skimmed milk powder. After sufficient washing, the monoclonal phage supernatant was added to a 96-well plate and incubated at 37° C. for 2 hours. After thorough washing, HRP-labeled anti-M13 antibody (GE healthcare, 27-9421-01) was added and reacted at 37° C. for 45 minutes. After thorough washing, TMB was added to develop color and reacted at room temperature for 5-10 minutes. Finally, the reaction was stopped with sulfuric acid. The OD value of each well was measured at 450 nm, and the phage antibody clone with higher OD450 value was selected for sequencing. After obtaining the heavy chain and the light chain variable region gene sequences of each phage antibody clone, each phage antibody was re-designed as a full-length IgG1,λ antibody: a primer was designed to perform PCR amplification of the VH of each phage antibody clone, and the PCR product was cloned by recombination to the pCMV-IgG1NDL antibody heavy chain expression vector double digested with AgeI and SalI. A primer was designed for PCR amplification of the VL of each phage antibody clone, and the PCR product was cloned into the pCMV-λ antibody light chain expression vector doubled digested with AgeI and BsiWI. After correct sequencing, the heavy chain and the light chain expression vectors of each antibody were co-transfected into 293F cells for transient expression. After 7 days of culture in serum-free medium, the cell culture supernatant was collected and purified by ProteinA column to obtain antibody protein. Purified antibody was dialyzed with PBS, and finally quantified with BCA Protein Assay Kit (Pierce, 23225). The binding affinity of the above full-length antibody against the recombinant human PD-L1-His protein (Origincell Therapeutics Co., Ltd.) by using a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then bounded with the double-diluted antigen solution (50, 25, 12.5, 6.25, 3.125, 1.56 nM) with 7 concentration gradients at 1500 rpm for 5 minutes, and finally dissociated at 1500 rpm for 10 minutes. The AHC sensor was regenerated by glycine pulses and then reused. The results obtained will be analyzed by Octet Data Analysis 9.0 software (Pall ForteBio Analytics Co., Ltd.) to obtain the $K_D$, $K_{on}$ (1/Ms) and $K_{off}$ (1/s). After screening the obtained mutant clones with increased affinity, the amino acid mutation points with increased affinity in different CDR regions were combined by using methods such as Overlapping PCR, and then the antibody protein was expressed and purified according to the above method and the affinity was determined. After multiple rounds of screening and combination, the top 5 YN-003 antibody mutant clones with high affinity were named YN-035 antibody, YN-036 antibody, YN-037 antibody, YN-038 antibody, and YN-039 antibody, respectively. The affinity values of the 5 antibodies obtained by the above method are shown in Table 9. The results show that the affinity of YN-035 antibody, YN-036 antibody, YN-037 antibody, YN-038 antibody, and YN-039 antibody were all higher than the anti-PD-L1 antibodies Atezolizumab and Avelumab.

TABLE 9

Binding Affinity of PD-L1 Antibody to Human PD-L1-His

| | Human PD-L1-His | | | | | | |
|---|---|---|---|---|---|---|---|
| Antibody | $K_D$ (M) | $K_D$ Error | $K_{on}$ (1/Ms) | $K_{on}$ Error | $K_{off}$(1/s) | $K_{off}$ Error | Full R^2 |
| Atezolizumab | $9.16 \times 10^{-10}$ | $8.79 \times 10^{-12}$ | $3.78 \times 10^{5}$ | $1.95 \times 10^{3}$ | $3.46 \times 10^{-4}$ | $2.80 \times 10^{-6}$ | 0.9984 |
| Avelumab | $1.03 \times 10^{-9}$ | $9.20 \times 10^{-12}$ | $2.96 \times 10^{5}$ | $1.31 \times 10^{3}$ | $3.05 \times 10^{-4}$ | $2.37 \times 10^{-6}$ | 0.9991 |
| YN-035 | $4.52 \times 10^{-10}$ | $3.54 \times 10^{-12}$ | $4.27 \times 10^{5}$ | $1.16 \times 10^{3}$ | $1.93 \times 10^{-4}$ | $1.42 \times 10^{-6}$ | 0.9995 |
| YN-036 | $4.74 \times 10^{-10}$ | $4.95 \times 10^{-12}$ | $3.69 \times 10^{5}$ | $1.22 \times 10^{3}$ | $1.75 \times 10^{-4}$ | $1.73 \times 10^{-6}$ | 0.9994 |
| YN-037 | $3.82 \times 10^{-10}$ | $5.66 \times 10^{-12}$ | $3.55 \times 10^{5}$ | $1.36 \times 10^{3}$ | $1.36 \times 10^{-4}$ | $1.94 \times 10^{-6}$ | 0.9991 |
| YN-038 | $4.47 \times 10^{-10}$ | $4.61 \times 10^{-12}$ | $3.50 \times 10^{5}$ | $1.05 \times 10^{3}$ | $1.56 \times 10^{-4}$ | $1.54 \times 10^{-6}$ | 0.9995 |
| YN-039 | $4.85 \times 10^{-10}$ | $4.41 \times 10^{-12}$ | $3.56 \times 10^{5}$ | $1.02 \times 10^{3}$ | $1.73 \times 10^{-4}$ | $1.49 \times 10^{-6}$ | 0.9995 |

The amino acid sequence of the YN-035 antibody heavy chain variable region (YN-035 VH) is shown in SEQ ID NO: 31, the amino acid sequence of the YN-035 antibody heavy chain is shown in SEQ ID NO: 32, the amino acid sequence of the YN-035 antibody light chain variable region (YN-035 VL) is shown in SEQ ID NO: 33, and the amino acid sequence of the YN-035 antibody light chain is shown in SEQ ID NO: 34.

The amino acid sequence of the YN-036 antibody heavy chain variable region (YN-036 VH) is shown in SEQ ID NO: 35, the amino acid sequence of the YN-036 antibody heavy chain is shown in SEQ ID NO: 36, The amino acid sequence of the YN-036 antibody light chain variable region (YN-036VL) is shown in SEQ ID NO: 33, and the amino acid sequence of the YN-036 antibody light chain is shown in SEQ ID NO: 34.

The amino acid sequence of the YN-037 antibody heavy chain variable region (YN-037 VH) is shown in SEQ ID NO: 35, the amino acid sequence of the YN-037 antibody heavy chain is shown in SEQ ID NO: 36, the amino acid sequence of the YN-037 antibody light chain variable region (YN-037VL) is shown in SEQ ID NO: 37, and the amino acid sequence of the YN-037 antibody light chain is shown in SEQ ID NO: 38.

The amino acid sequence of the YN-038 antibody heavy chain variable region (YN-038 VH) is shown in SEQ ID NO: 35, the amino acid sequence of the YN-038 antibody heavy chain is shown in SEQ ID NO: 36, the amino acid sequence of the YN-038 antibody light chain variable region (YN-038VL) is shown in SEQ ID NO: 39, and the amino acid sequence of the YN-038 antibody light chain is shown in SEQ ID NO: 40.

The amino acid sequence of the YN-039 antibody heavy chain variable region (YN-039VH) is shown in SEQ ID NO: 35, the amino acid sequence of the YN-039 antibody heavy chain is shown in SEQ ID NO: 36, the amino acid sequence of the YN-039 antibody light chain variable region (YN-039 VL) is shown in SEQ ID NO: 41, and the amino acid sequence of the YN-039 antibody light chain is shown in SEQ ID NO: 42.

Figure 9:
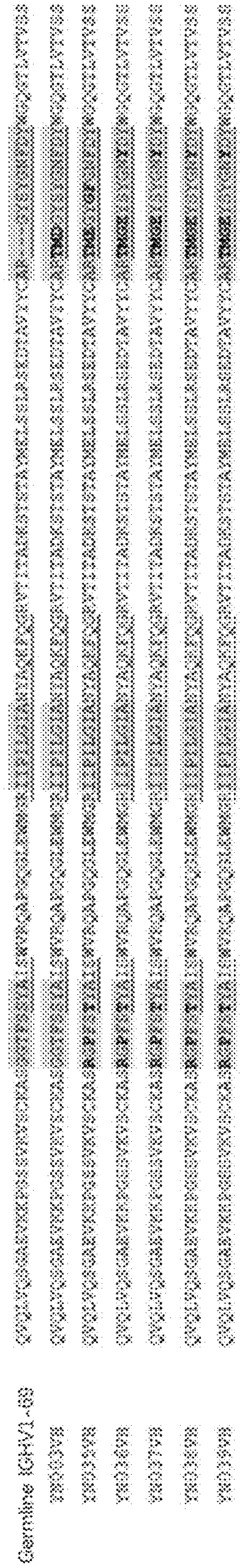
FIG. 9 shows the alignment of the amino acid sequences of the heavy chain variable regions (YN-003VH(SEQ ID NO: 9); YN-035VH(SEQ ID NO: 31); YN-036VH(SEQ ID NO: 35); YN-037VH(SEQ ID NO: 35); YN-038VH(SEQ ID NO: 35); YN-039VH(SEQ ID NO: 35 of the PD-L1 antibody of the present application with the related germline sequences (Germline IGHV 1-69(SEQ ID NO: 93)). The underlined are the CDRs determined according to the Kabat definition method, and the shaded parts are the CDRs determined according to the IMGT definition method.
Figure 10:
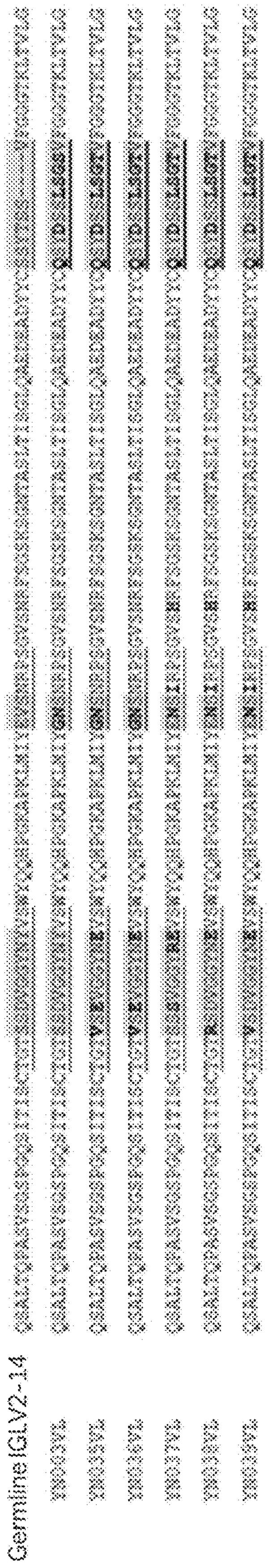
FIG. 10 shows the alignment of the amino acid sequences of the light chain variable regions (YN-003VL(SEQ ID NO: 11); YN-035VL(SEQ ID NO: 33); YN-036VL(SEQ ID NO: 33); YN-037VL(SEQ ID NO: 37); YN-038VL(SEQ ID NO: 39); YN-039VL(SEQ ID NO: 41) of the PD-L1 antibody of the present application with the related germline sequences (Germline IGLV 2-14(SEQ ID NO: 94)). The underlined are the CDRs determined according to the Kabat definition method, and the shaded parts are the CDRs determined according to the IMGT definition method.

FIG. 9 shows the amino acid sequence alignment of the heavy chain variable regions and related germline sequences of the antibodies YN-003, and YN-035 to YN-039, wherein the underlined are the CDRs determined according to the Kabat definition method. FIG. 10 shows the amino acid sequence alignment of the light chain variable regions and related germline sequences of the antibodies YN-003 and YN-035 to YN-039, wherein the underlined are the CDRs determined according to the Kabat definition. Of those, the amino acid sequence of HCDR1 of the antibody YN-003 is shown in SEQ ID NO: 46, the amino acid sequence of HCDR1 of YN-035 to YN-039 is shown in SEQ ID NO: 47; the amino acid sequence of HCDR2 of the antibody YN-003 and the amino acid sequence of HCDR2 of the antibodies YN-035 to YN-039 is shown in SEQ ID NO: 48; the amino acid sequence of HCDR3 of YN-003 is shown in SEQ ID NO: 50; the amino acid sequence of HCDR3 of YN-035 is shown in SEQ ID NO: 51; and the amino acid sequence of HCDR3 of the antibodies YN-036 to YN-039 is shown in SEQ ID NO: 52.

The amino acid sequence of LCDR1 of the antibody YN-003 is shown in SEQ ID NO: 54, the amino acid sequence of LCDR1 of the antibodies YN-035 and YN-036 is shown in SEQ ID NO: 55, the amino acid sequence of LCDR1 of the antibody YN-037 is shown in SEQ ID NO: 56, the amino acid sequence of LCDR1 of the antibody YN-038 is shown in SEQ ID NO: 57, the amino acid sequence of LCDR1 of the antibody YN-039 is shown in SEQ ID NO: 58; the amino acid sequence of LCDR2 of the antibody YN-003 and the antibodies YN-035 to YN-036 is shown in SEQ ID NO: 60, the amino acid sequence of LCDR2 of the antibodies YN-037 to YN-039 is shown in SEQ ID NO: 61; the amino acid sequence of LCDR3 of the antibody YN-003 is shown in SEQ ID NO: 63; and the amino acid sequence of LCDR3 of antibodies YN-035 to YN-039 is shown in SEQ ID NO: 64.

Figure 11:
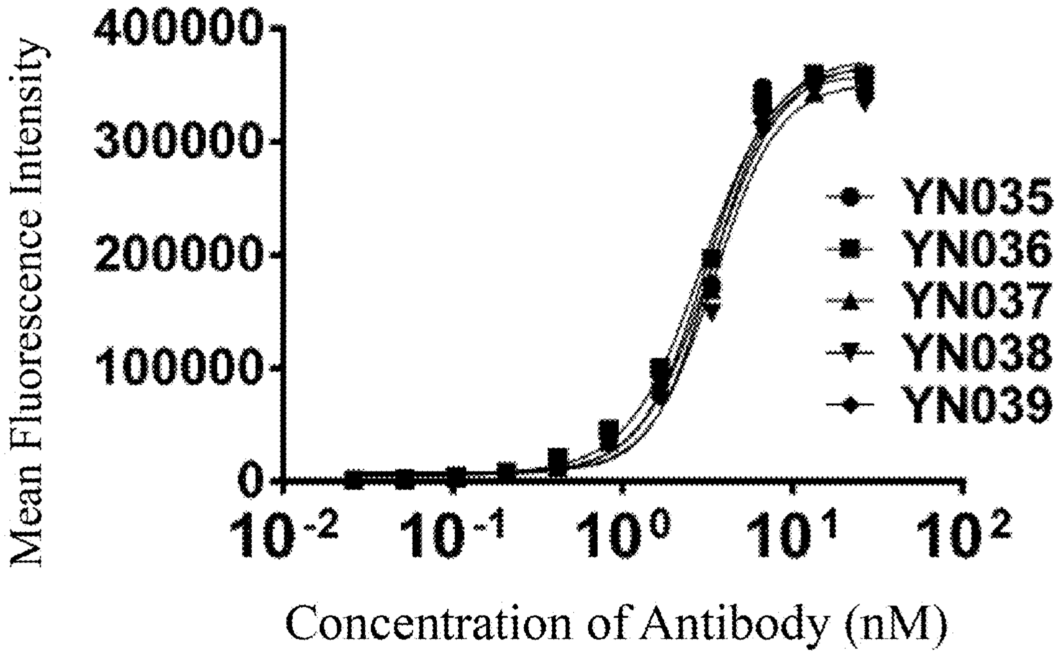
FIG. 11 shows the binding of the PD-L1 antibody of the present application to the CHO cells that stably expresses the human PD-L1.

The binding activity of the PD-L1 antibodies YN-035, YN-036, YN-037, YN-038, YN-039 to human PD-L1 was detected by flow cytometry: to $1\times10^6$/ml of the CHO cells that stably expressed human PD-L1 was added individual double-diluted PD-L1 antibodies. The mixture was mixed well and incubated at 4° C. for 1 hr. After cell washing, Goat $F(ab')_2$ Anti-Human IgG-Fc (DyLight 650) (ab98593, Abcam) was added and incubated at 4° C. for 30 min. After cell washing, the fluorescence intensity was detected by a flow cytometer (Intellicyt iQue Screener). The experimental results are shown in FIG. 11: YN-035, YN-036, YN-037, YN-038, YN-039 all can effectively bind to CHO cells expressing human PD-L1.

Figure 12:
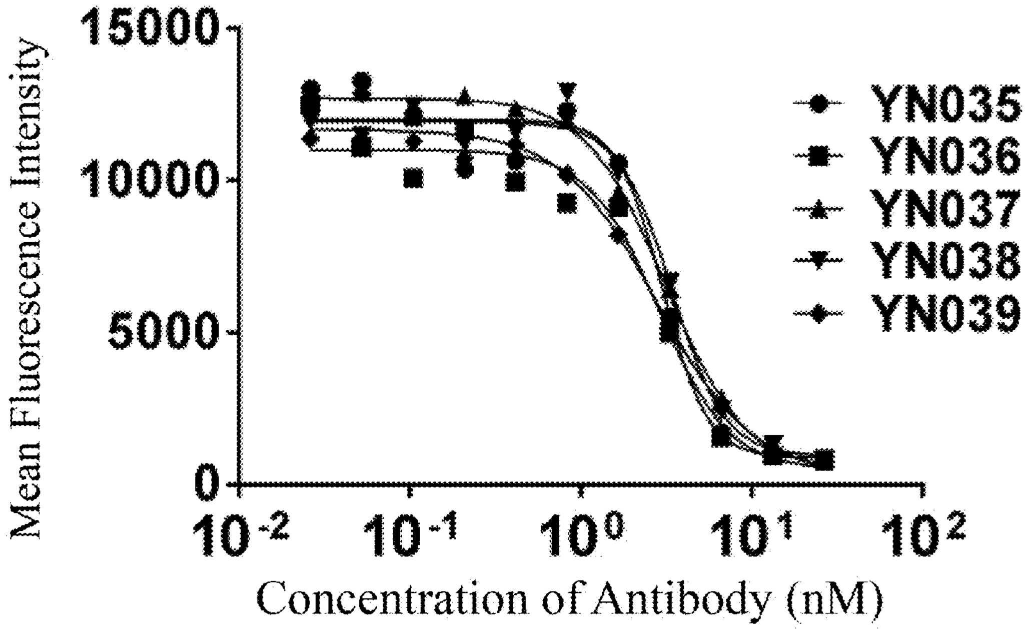
FIG. 12 shows the status that the PD-L1 antibody of the present application inhibits the binding of human PD-1 to human PD-L1.

The inhibitory capacity of the PD-L1 antibodies YN-035, YN-036, YN-037, YN-038, YN-039 to human PD-L1/human PD-1 was detected by flow cytometry: the human PD-1-Fc protein (Origincell Therapeutics Co., Ltd.) was labeled with biotin (EZ-Link Sulfo-NHS-LC-Biotin, Pierce, 21327). The human PD-1-Fc labeled with a subsaturated concentration of biotin was added into $1\times10^6$/ml of the CHO cells that stably expressed human PD-L1, and then individual double-diluted antibodies were immediately added, mixed well and incubated (4° C. 1 hr). After cell washing, Streptavidin R-PE Conjugate (life technology, SA10041) was added and incubated (4° C., 30 min). After cell washing, the fluorescence intensity was detected by a flow cytometer (Intellicyt iQue Screener). The experimental results are shown in FIG. 12: the PD-L1 antibodies YN-035, YN-036. YN-037, YN-038, YN-039 all can effectively inhibit the binding of human PD-1 to CHO cells expressing human PD-L1.

Figure 13:
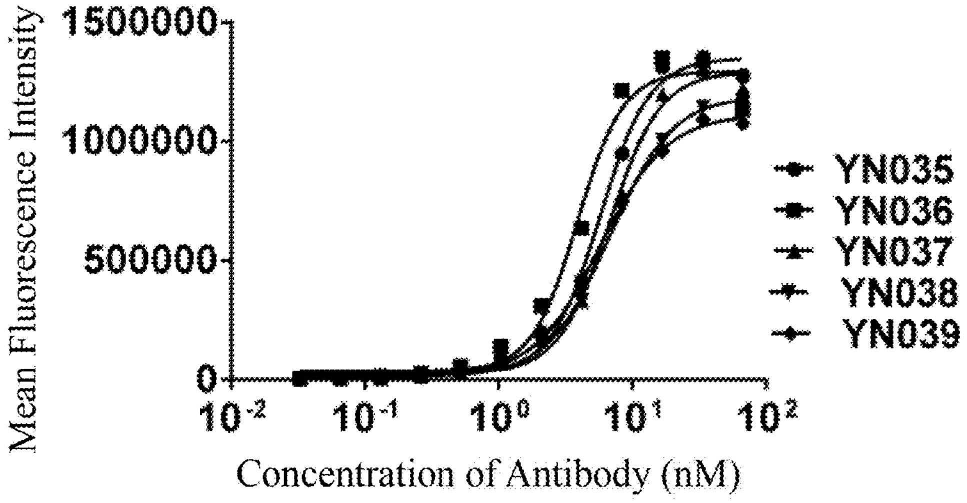
FIG. 13 shows the status that the PD-L1 antibody of the present application binds to the CHO cells that stably expresses mouse PD-L1.

The binding activity of the PD-L1 antibodies YN-035, YN-036, YN-037, YN-038, YN-039 to mouse PD-L1 was detected by flow cytometry: to $1\times10^6$/ml CHO cells that stably expressed mouse PD-L1 were added individual double diluted PD-L1 antibodies. The mixture was mixed well and incubated at 4° C. for 1 hr. After cell washing, Goat $F(ab')_2$ Anti-Human IgG-Fc (DyLight 650) (ab98593) was added and incubated at 4° C. for 30 min. After cell washing, the fluorescence intensity was detected by a flow cytometer (Intellicyt iQue Screener). The experimental results are shown in FIG. 13: YN-035, YN-036, YN-037, YN-038, YN-039 all can effectively bind to the CHO cells expressing mouse PD-L1.

Figure 14:
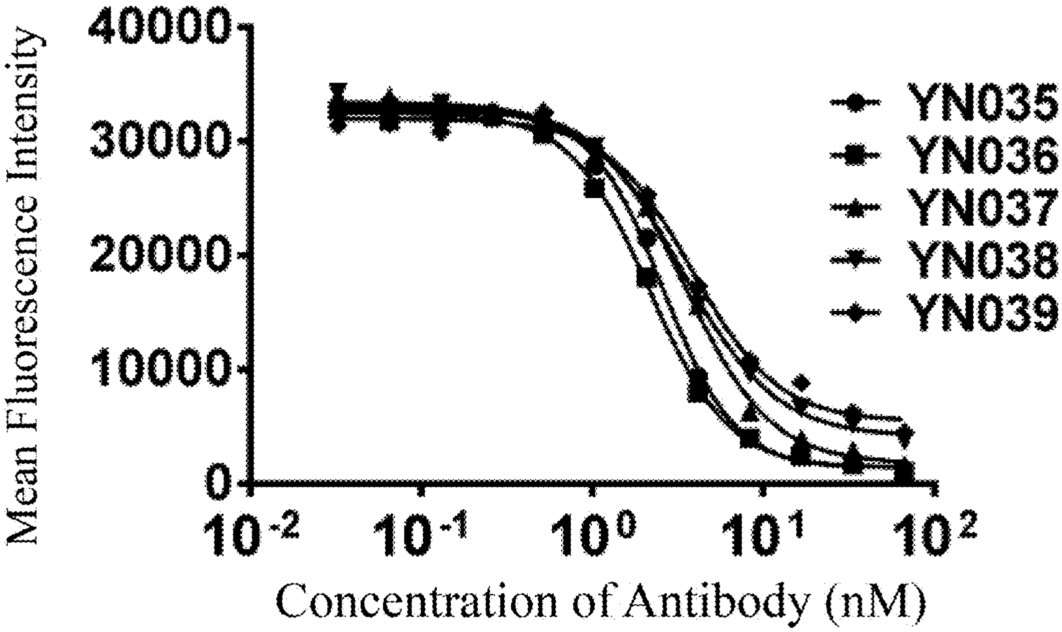
FIG. 14 shows the status that the PD-L1 antibody of the present application inhibits the binding of mouse PD-1 to mouse PD-L1.

The inhibitory capacity of the PD-L1 antibodies YN-035, YN-036, YN-037, YN-038, YN-039 to mouse PD-L1/mouse PD-1 was detected by flow cytometry: mouse PD-1-Fc (Origincell Therapeutics Co., Ltd.) was labeled with biotin (EZ-Link Sulfo-NHS-LC-Biotin, Pierce, 21327). The mouse PD-1-Fc labeled with a subsaturated concentration of biotin was added into $1\times10^6$/ml of the CHO cells that stably expressed mouse PD-L1, and then individual double-diluted antibodies were immediately added, mixed well and incubated (4° C., 1 hr). After cell washing, Streptavidin R-PE Conjugate (life technology, SA10041) was added and incubated (4° C., 30 min). After cell washing, the fluorescence intensity was detected by a flow cytometer (Intellicyt iQue Screener). The results are shown in FIG. 14: the PD-L1 antibodies YN-035. YN-036, YN-037, YN-038, YN-039 all can effectively inhibit the binding of mouse PD-1 to the CHO cells that stably expressed mouse PD-L1.

Example 17. Construction and Identification of Anti-PD-L1/CD137 Bispecific Antibodies YN-051 and YN-052

The first polypeptide gene of anti-PD-L1/CD137 bispecific antibody YN-051 was constructed by molecular cloning method, such as, Overlap PCR, Site-directed Mutation, or the like, using the heavy chain gene of the anti-PD-L1 antibody YN-035 and the heavy chain and the light chain genes of the anti-human CD137 antibody YN-006, and cloned by recombination into the pCMV-IgG1AEM vector double digested with AgeI and BamHI, so as to construct the first polypeptide expression vector of YN-051. The second polypeptide gene of YN-051 is the same as the light chain gene of YN-035. The second polypeptide expression vector of YN-035 is the light chain expression vector of YN-035.

After correct sequencing, the first polypeptide and the second polypeptide expression vectors of the anti-PD-L1/CD137 bispecific antibody YN-051 were co-transfected into 293F cell for transient expression. After culturing in serum-free medium for 7 days, the cell culture supernatant was collected and purified by Protein A column to obtain the antibody protein. The purified antibody was dailyzed with PBS, and finally quantified with BCA Protein Assay Kit (Pierce, 23225).

The amino acid sequence of the first polypeptide of YN-051 is shown in SEQ ID NO: 43, and the amino acid sequence of the second polypeptide of YN-051 is shown in SEQ ID NO: 34.

The first polypeptide gene of anti-PD-L1/CD137 bispecific antibody YN-052 was constructed by molecular cloning method, such as, Overlap PCR, Site-directed Mutation, or the like, using the heavy chain gene of the anti-PD-L1 antibody YN-036 and the heavy chain and the light chain genes of the anti-human CD137 antibody YN-006, and cloned by recombination into the pCMV-IgG1AEM vector double digested with AgeI and BamHI, so as to construct the first polypeptide expression vector of YN-052. The second polypeptide gene of YN-052 is the same as the light chain gene of YN-036. The second polypeptide expression vector of YN-052 is the light chain expression vector of YN-036.

After correct sequencing, the first polypeptide and the second polypeptide expression vectors of the anti-PD-L1/CD137 bispecific antibody YN-052 were co-transfected into 293F cell for transient expression. After culturing in serum-free medium for 7 days, the cell culture supernatant was collected and purified by Protein A column to obtain the antibody protein. The purified antibody was dialyzed with PBS, and finally quantified with BCA Protein Assay Kit (Pierce, 23225).

The amino acid sequence of the first polypeptide of YN-052 is shown in SEQ ID NO: 44, and the amino acid sequence of the second polypeptide of YN-052 is shown in SEQ ID NO: 34.

The binding affinity of the anti-PD-L1/CD137 bispecific antibodies YN-051 and YN-051 to the recombinant human PD-L1-His protein (Origincell Therapeutics Co., Ltd.) was measured by a molecular interaction analyzer (Octet RED384, purchased from Pall ForteBio Analytics Co., Ltd.).

The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted antigen solution (50, 25, 12.5, 6.25, 3.125, 1.56 nM) with 7 concentration gradients at 1500 rpm for 5 minutes; and finally dissociated at 1500 rpm for 10 minutes. The AHC sensor was regenerated by glycine pulses and then reused. The obtained results would be analyzed by Octet Data Analysis 9.0 software (Pall ForteBio Analytics Co., Ltd.) to give the $K_D$, $K_{on}$ (1/Ms) and $K_{off}$ (1/s). The measured results of the binding affinity of YN-007 to human PD-L1-Fc are shown in Table 10.

TABLE 10

Binding Affinity of Anti-PD-L1/CD137 Bispecific Antibody to Human PD-L1-His

| | Human PD-L1-His | | | | | | |
|---|---|---|---|---|---|---|---|
| Antibody | $K_D$ (M) | $K_D$ Error | $K_{on}$ (1/Ms) | $K_{on}$ Error | $K_{off}$ (1/s) | $K_{off}$ Error | Full R^2 |
| YN-051 | $5.17 \times 10^{-10}$ | $4.97 \times 10^{-12}$ | $5.32 \times 10^{5}$ | $2.54 \times 10^{3}$ | $2.75 \times 10^{-4}$ | $2.29 \times 10^{-6}$ | 0.9981 |
| YN-052 | $5.72 \times 10^{-10}$ | $5.69 \times 10^{-12}$ | $4.48 \times 10^{5}$ | $2.06 \times 10^{3}$ | $2.57 \times 10^{-4}$ | $2.26 \times 10^{-6}$ | 0.9984 |

The binding affinity of the anti-PD-L1/CD137 bispecific antibodies YN-051 and YN-052 to the recombinant human CD137-His protein (Origincell Therapeutics Co., Ltd.) was measured by a molecular interaction analyzer (Octet RED384, purchased from Pall ForteBio Analytics Co., Ltd.). The antigen-antibody binding kinetics were analyzed by the biofilm interference (BLI) technology, using a molecular interaction analyzer (Octet RED384, purchased from Pall ForteBio Analytics Co., Ltd.) and using a PBS buffer containing 0.1% BSA and 0.02% Tween 20. The antibody with a concentration of 50 nM was fixed with the AHC sensor, and bound at 1500 rpm for 5 minutes; then it was bound with the double-diluted recombinant human CD137-His protein antigen solution (100, 50, 25, 12.5, 6.25, 3.125, 1.56 nM) at 1500 rpm for 5 minutes; and finally dissociated at 1500 rpm for 10 minutes. The AHC sensor was regenerated by glycine pulses and then reused. The obtained results would be analyzed by Octet Data Analysis 9.0 software (Pall ForteBio Analytics Co., Ltd.) to give the $K_D$, $K_{on}$ (1/Ms) and $K_{off}$ (1/s).

The measured results of the binding affinity of anti-PD-L1/CD137 bispecific antibodies YN-051 and YN-052 to human CD137 are shown in Table 11.

TABLE 11

Binding Affinity of Anti-PD-L1/CD137 Bispecific Antibody to Human CD137-His

| | Human 4-1BB-His | | | | | | |
|---|---|---|---|---|---|---|---|
| Antibody | $K_D$ (M) | $K_D$ Error | kon (1/Ms) | kon Error | kdis (1/s) | kdis Error | Full R^2 |
| YN-051 | $1.64 \times 10^{-9}$ | $3.93 \times 10^{-11}$ | $8.99 \times 10^{4}$ | $7.25 \times 10^{2}$ | $1.47 \times 10^{-4}$ | $3.33 \times 10^{-6}$ | 0.9981 |
| YN-052 | $2.08 \times 10^{-9}$ | $4.36 \times 10^{-11}$ | $8.37 \times 10^{4}$ | $6.93 \times 10^{2}$ | $1.74 \times 10^{-4}$ | $3.35 \times 10^{-6}$ | 0.9982 |

Figure 15:
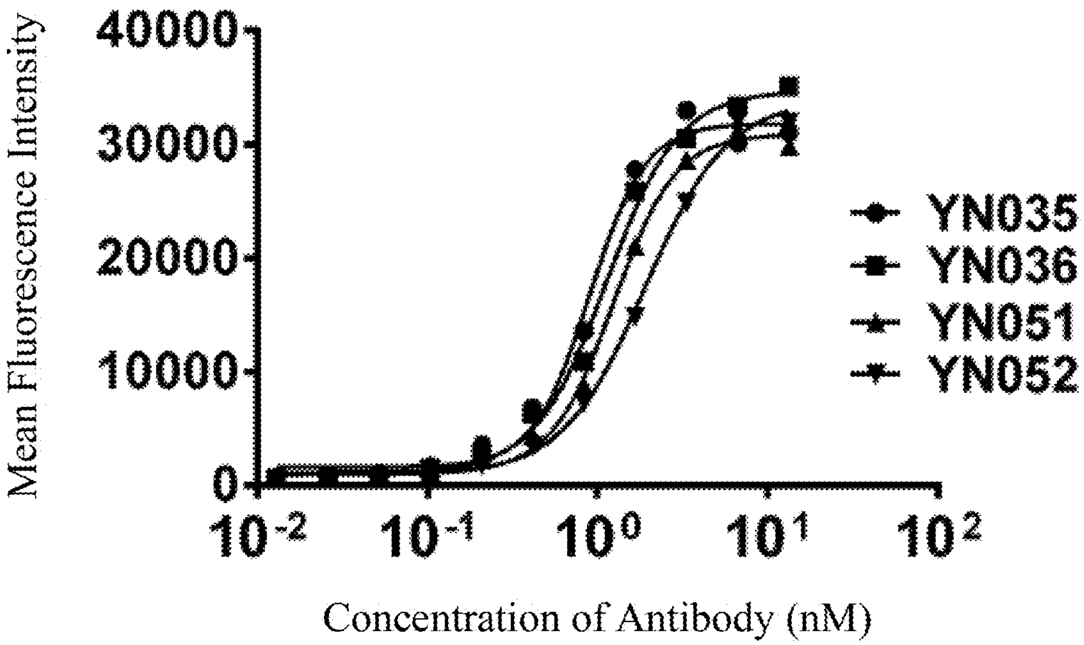
FIG. 15 shows the status that the PD-L1 antibody of the present application binds to MDA-MB-231 cells.

Human breast cell strain MDA-MB-231 (Shanghai Chinese Academy of Sciences Cell Library) highly expresses the human PD-L1 molecule. The binding of the PD-1 antibodies YN-035, YN-036 and the anti-PD-L1/CD137 bispecific antibodies YN-051 and YN-052 to MDA-MB-231 cells was detected by flow cytometry: to $1\times10^6$/ml of MDA-MB-231 cells was added individual double-diluted antibodies, respectively, mixed well and incubated at 4° C. for 1 hr. After cell washing. Goat $F(ab')_2$ Anti-Human IgG-Fc (DyLight 650)) (ab98593, abcam) was added and incubated at 4° C. for 30 min. After cell washing, the fluorescence intensity was detected by a flow cytometer (Intellicyt iQue Screener). The experimental results are shown in FIG. 15: YN-035, YN-036, YN-051 and YN-052 all can effectively bind to MDA-MB-231 cells.

Figure 16:
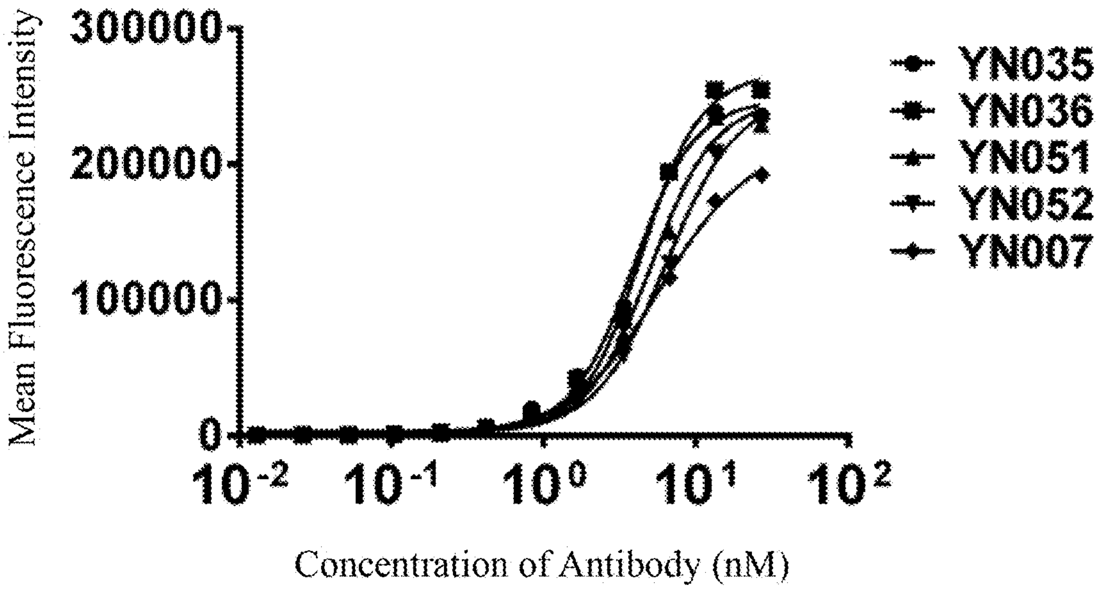
FIG. 16 shows the status that the PD-L1 antibody and the PD-L1/CD137 bispecific antibody of the present application bind to the CHO cells which stably express human PD-L1.

The binding activity of the PD-1 antibodies YN-035, YN-036 and the anti-PD-L1/CD137 bispecific antibodies YN-051 and YN-052 to human PD-L1 was detected by flow cytometry: to $1\times10^6$/ml of the CHO cells that stably expressed human PD-L1 was added individual double-diluted antibodies, respectively, mixed well and incubated at 4° C. for 1 hr. After cell washing. Goat $F(ab')_2$ Anti-Human IgG-Fc (DyLight 650) (ab98593, abcam) was added and incubated at 4° C. for 30 min. After cell washing, the fluorescence intensity was detected by a flow cytometer (Intellicyt iQue Screener). The experimental results are shown in FIG. 16: YN-035, YN-036, YN-051, YN-052, YN-007 all can effectively bind to CHO cells expressing human PD-L1.

Figure 17:
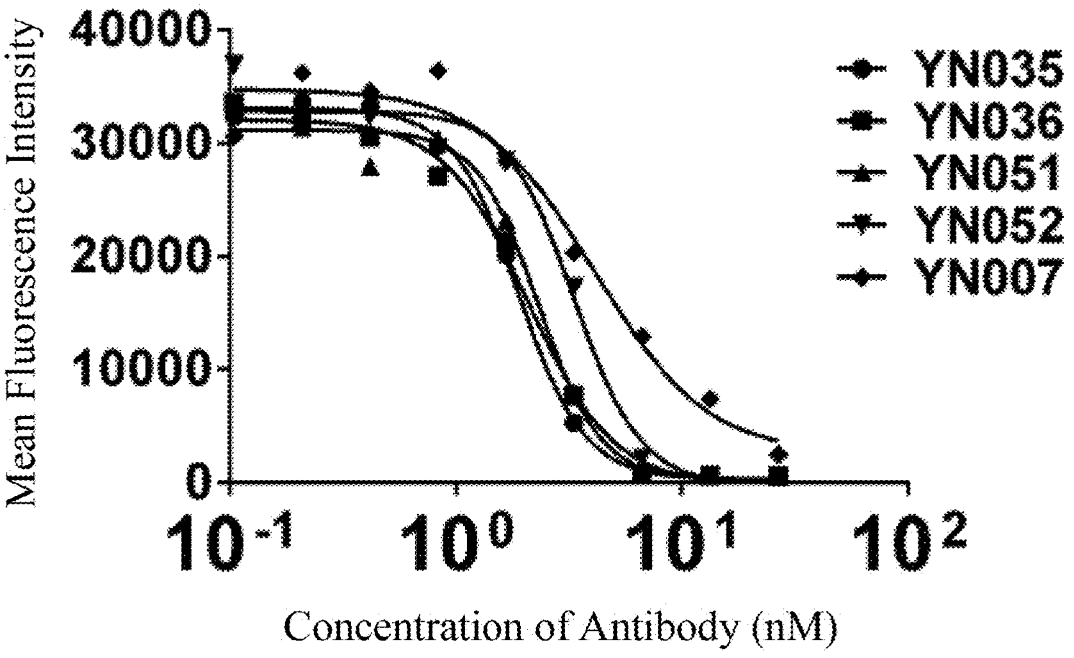
FIG. 17 shows the status that the PD-L1 antibody and PD-L1/CD137 bispecific antibody of the present application inhibit the binding of human PD-1 to human PD-L1.

The inhibitory capacity of the PD-1 antibodies YN-035, YN-036 and the anti-PD-L1/CD137 bispecific antibodies YN-051, YN-052, YN-007 to human PD-L1/human PD-1 was detected by flow cytometry: the human PD-1-Fc protein was labeled with biotin (EZ-Link Sulfo-NHS-LC-Biotin, Pierce, 21327). The human PD-1-Fc labeled with a subsaturated concentration of biotin was added into $1\times10^6$/ml of the CHO cells that stably expressed human PD-L1, and then individual double-diluted antibodies were immediately added, mixed well and incubated (4° C., 1 hr). After cell washing. Streptavidin R-PE Conjugate (life technology, SA10041) was added and incubated (4° C., 30 min). After cell washing, the fluorescence intensity was detected by a flow cytometer (Intellicyt iQue Screener). The experimental results are shown in FIG. 17: the PD-L1 antibodies YN-035, YN-036, YN-051, YN-052, YN-007 all can effectively inhibit the binding of human PD-1 to the CHO cells expressing human PD-L1.

Figure 18:
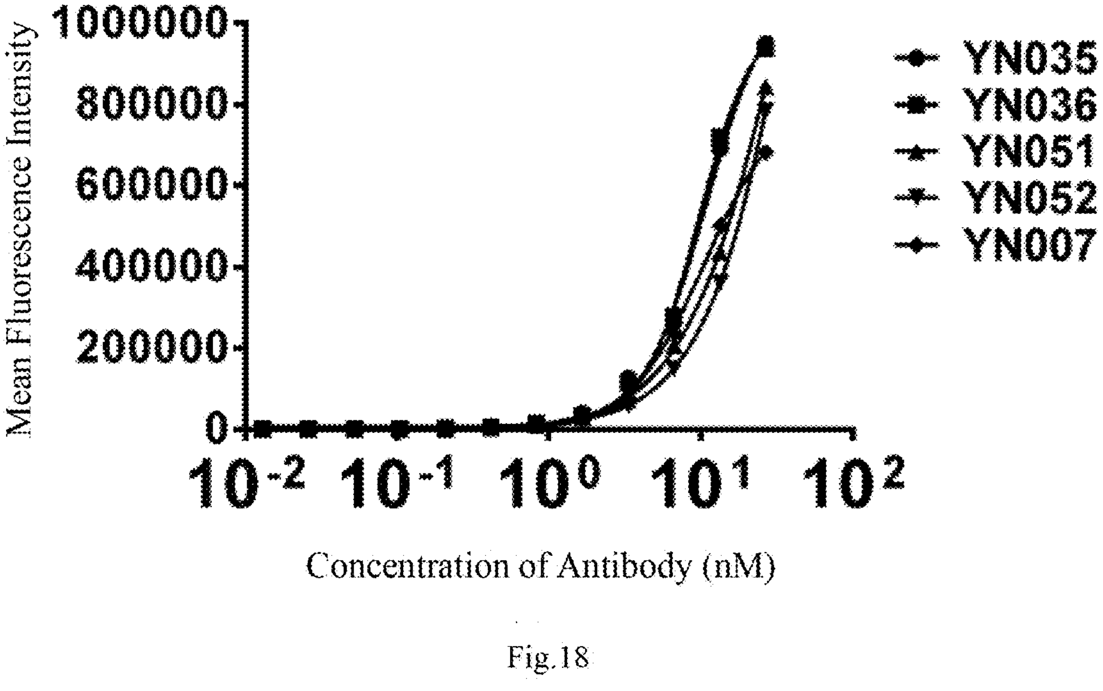
FIG. 18 shows the status that the PD-L1 antibody and PD-L1/CD137 bispecific antibody of the present application bind to the CHO cells which stably express mouse PD-L1.

The binding activity of the PD-1 antibodies YN-035, YN-036 and the anti-PD-L1/CD137 bispecific antibodies YN-007, YN-051 and YN-052 to mouse PD-L1 was detected by flow cytometry: to $1\times10^6$/ml of the CHO cells that stably expressed mouse PD-L1 was added individual double-diluted antibodies, respectively, mixed well and incubated at 4° C. for 1 hr. After cell washing. Goat $F(ab')_2$ Anti-Human IgG-Fc (DyLight 650) (ab98593, abcam) was added and incubated at 4° C. for 30 min. After cell washing, the fluorescence intensity was detected by a flow cytometer (Intellicyt iQue Screener). The experimental results are shown in FIG. 18: YN-035, YN-036, YN-051, YN-052, YN007 all can effectively bind to the CHO cells expressing mouse PD-L1.

Figure 19:
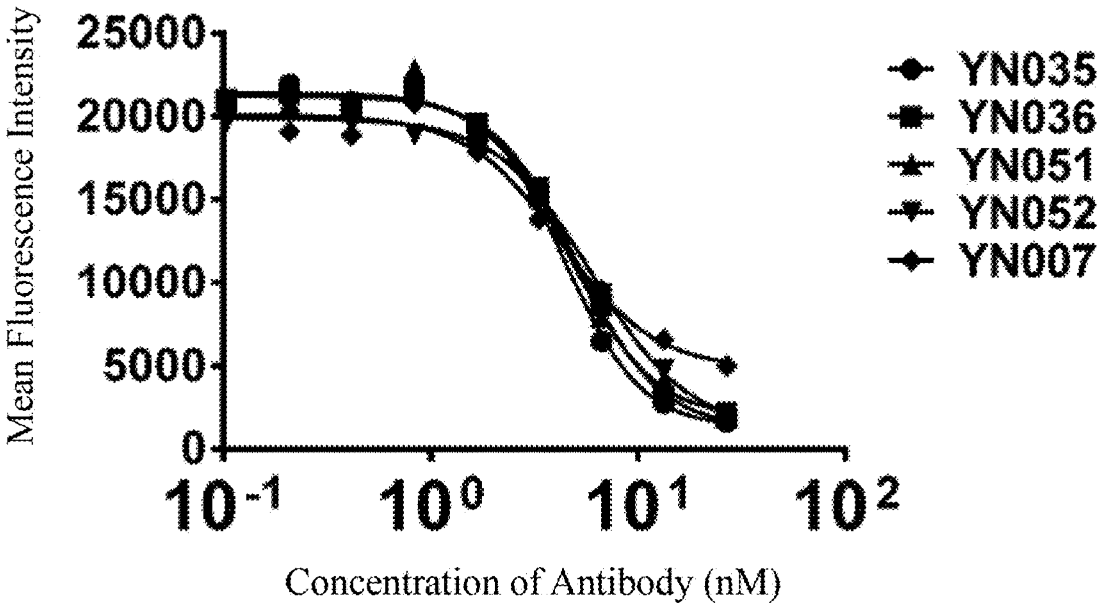
FIG. 19 shows the status that the PD-L1 antibody and PD-L1/CD137 bispecific antibody of the present application inhibit the binding of mouse PD-1 to mouse PD-L1.

The inhibitory capacity of the PD-1 antibodies YN-035, YN-036 and the anti-PD-L1/CD137 bispecific antibodies YN-007, YN-051 and YN-052 to mouse PD-L1/mouse PD-1 was detected by flow cytometry: the mouse PD-1-Fc labeled with biotin (EZ-Link Sulfo-NHS-LC-Biotin, Pierce, 21327). The mouse PD-1-Fc labeled with a subsaturated concentration of biotin was added into $1\times10^6$/ml of CHO cells stably expressing mouse PD-L1, and then individual double-diluted antibodies were immediately added, mixed well and incubated (4° C., 1 hr). After cell washing, Streptavidin R-PE Conjugate (life technology, SA10041) was added and incubated (4° C. 30 min). After cell washing, the fluorescence intensity was detected by a flow cytometer (Intellicyt iQue Screener). The results are shown in FIG. 19: the PD-L1 antibodies YN-035, YN-036, YN-051, YN-052, YN-007 all can effectively inhibit the binding of mouse PD-1 to the CHO cells expressing mouse PD-L1.

Figure 20:
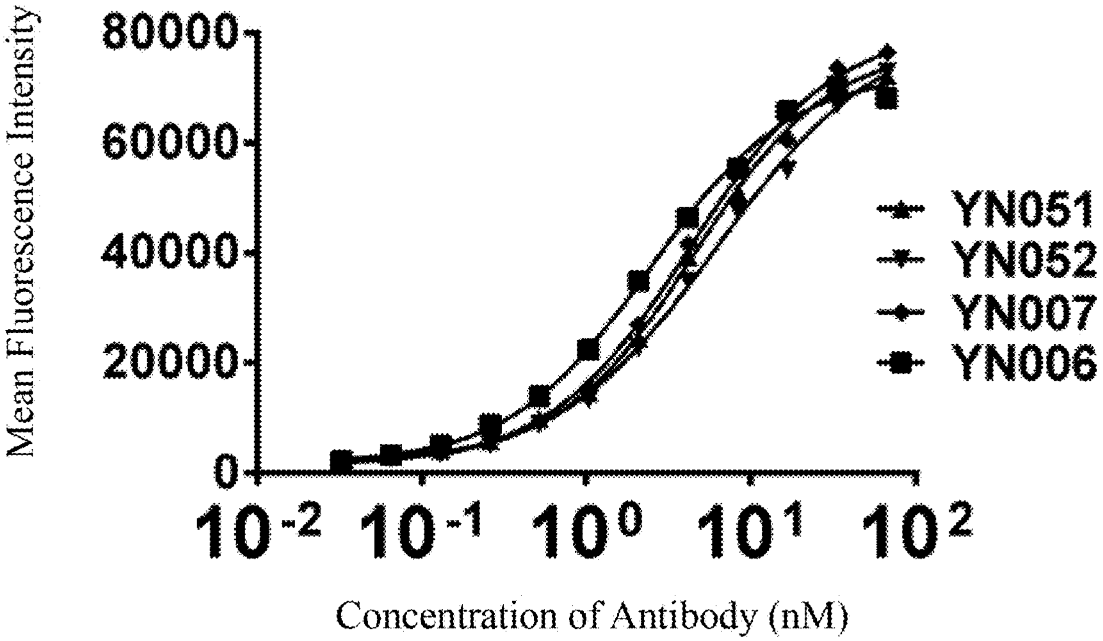
FIG. 20 shows the status that the CD137 antibody and PD-L1/CD137 bispecific antibody of the present application bind to the 293T cells which stably express human CD137.

The binding activity of the CD137 antibody YN-006 and the anti-PD-L1/CD137 bispecific antibodies YN-007, YN-051 and YN-052 to human CD137 was detected by flow cytometry: to $1\times10^6$/ml of 293T cells that stably express human CD137 was added individual double-diluted antibodies, respectively, mixed well and incubated at 4° C. for 1 hr. After cell washing, Goat $F(ab')_2$ Anti-Human IgG-Fc (DyLight 650) (ab98593, abcam) was added and incubated at 4° C. for 30 min. After cell washing, the fluorescence intensity was detected by a flow cytometer (Intellicyt iQue Screener). The experimental results are shown in FIG. 20: YN-006, YN-007, YN-051 and YN-052 all can effectively bind to the 293T cells expressing human CD137.

Example 18. SDS Polyacrylamide Gel Electrophoresis (SDS-PAGE) Analysis

Figure 21A:
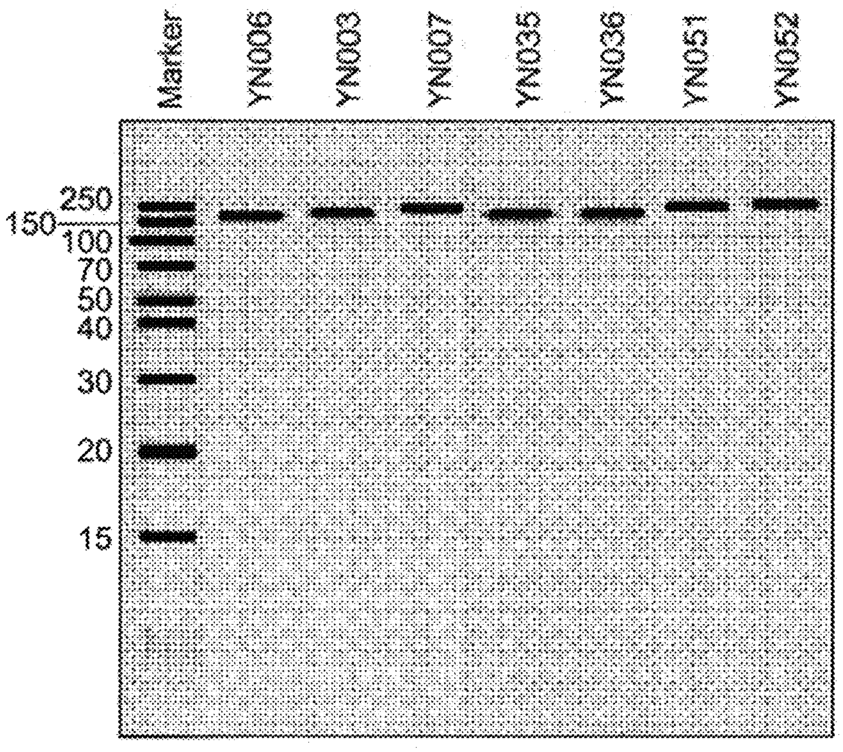
FIGS. 21A and 21B show the status that the molecular weight of the antibody of the present application is analyzed by SDS-PAGE analysis.
Figure 21B:
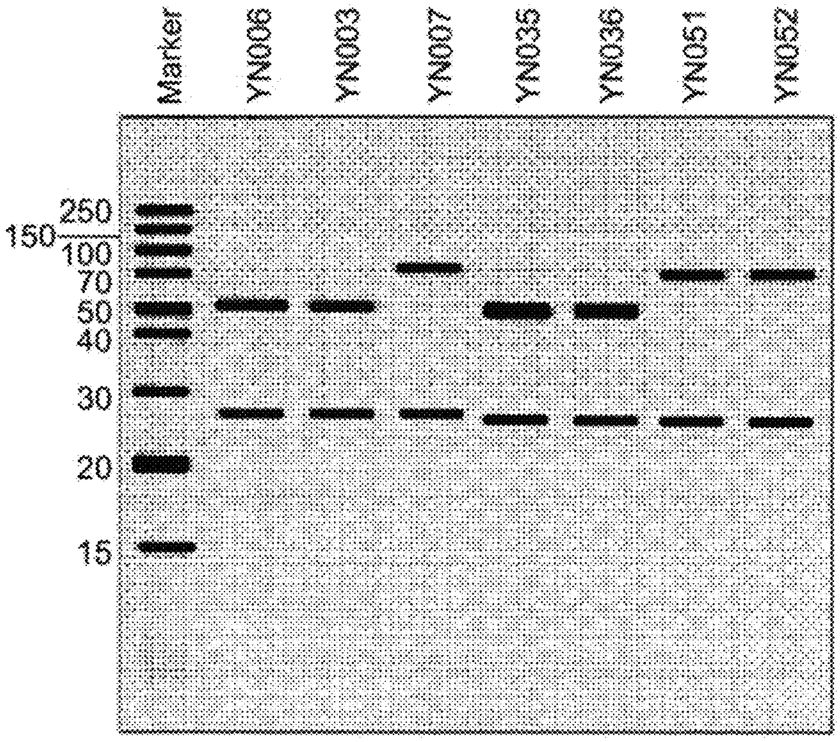

After being purified as above, the antibodies YN-003, YN-006, YN-007, YN-035, YN-036, YN-051, YN-052 were measured by SDS-PAGE under reducing and non-reducing conditions for their molecular weights. The results are shown in FIG. 21: under non-reducing conditions (as shown in FIG. 21*a*), the monoclonal antibodies YN-003, YN006, YN-035, and YN-036 are all presented as a band with a molecular weight of about 150 kDa, while the bispecific antibodies YN-007, YN-051, YN-052 are all presented as a band with a molecular weight of about 200 kDa. Under reducing conditions (as shown in FIG. 21*b*), the monoclonal antibodies YN-003, YN006, YN-035, and YN-036 are all presented as two bands with a molecular weight of about 55 kDa and 25 kDa, while the bispecific antibodies YN-007, YN-051, YN-052 are all presented as two bands with a molecular weight of about 75 kDa and 25 kDa.

Example 19. Agonistic Activity of Anti-PD-L1/CD137 Bispecific Antibody (Luciferase Activity Assay)

Figure 22:
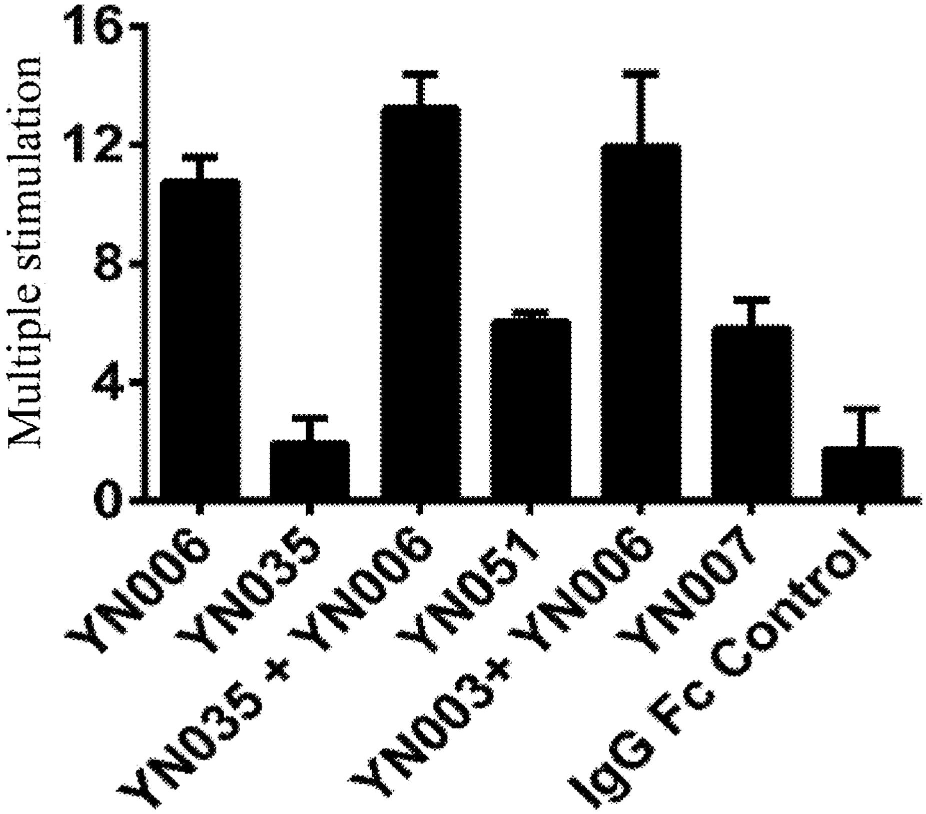
FIG. 22 shows the results of various antibodies of the present application stimulating the luciferase activity of the 293T cells which express the human CD137 and stably integrate luciferase reporter gene.

293T cells expressing human CD137 and stably integrated NFκB luciferase reporter gene were prepared. The cells were harvested, washed and resuspended in complete medium without phenol red (DMEM medium containing 10% fetal bovine serum, HEPES buffer, non-essential amino acids and L-glutamine) at a density of $6\times10^5$ cells/mL. 96-well plates (purchased from PerkinElmer) were plated, and 50 μl of cell suspension was added to each well. A cross-linked antibody (goat anti-human IgG Fc) was added at a ratio of 2.5:1, then YN-006 (10 μg/ml), YN-035 (10 μg/ml), YN-035+YN-006 (10 μg/ml+10 μg/ml), YN-051 (10 μg/ml), YN-003+YN006 (10 μg/ml+10 μg/ml), YN-007 (10 μg/ml), and control antibody IgG Fc (10 μg/ml) were added, respectively, and incubated at 37° C. for 5 hours. Subsequently, 75 μL of Bright-Glo Luciferase reagent (purchased from Promega) was added, and the luciferase activity was measured with a microplate reader (purchased from Tecan). The ratio of the cell fluorescence values of each antibody-treated cell group to the non-antibody-treated group was compared (see FIG. 22). The results show that as compared with the control IgG Fc. YN-006, YN035+YN006, YN003+YN006, YN-007, YN-051 all have an obvious agonistic activity, while the anti-PD-L1 antibody YN-035 does not (see FIG. 22).

Figure 23:
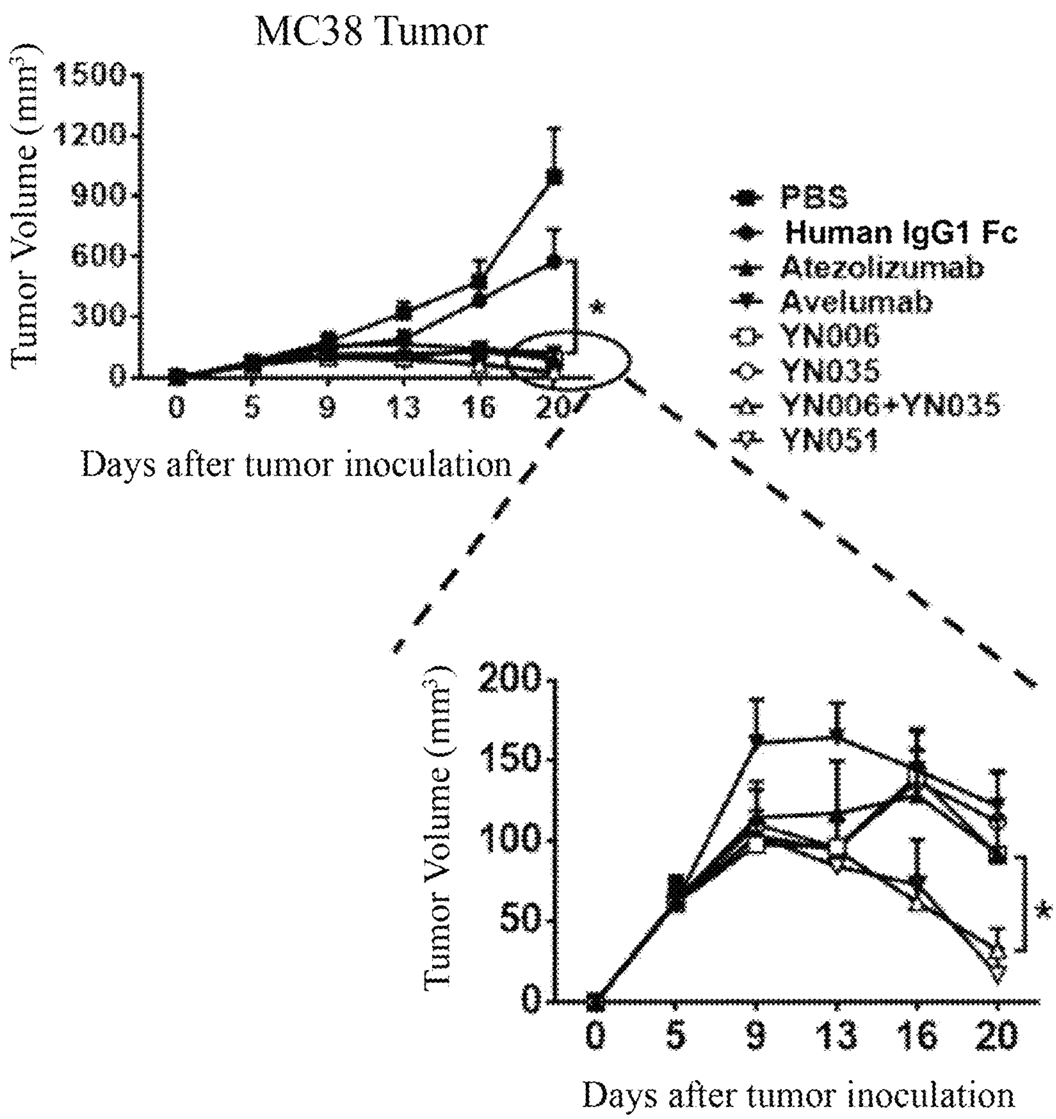
FIG. 23 shows the effect of the antibodies of the present application on the growth of MC38 tumors in CS7BL/6 female mice with human CD137 gene (*, P<0.05; Unpaired t test).

Example 20. Studies of Antitumor Effect of Anti-PD-L1/CD137 Bispecific Antibody in Colon Cancer-Bearing Mice On Day 0, 6-8 week old C57BL/6 female mice with human 4-1BB (B-hTNFRSF9 (4-1BB) mice, purchased from Beijing Biocytogen Co., Ltd.) were subcutaneously inoculated with $3\times10^6$ MC38 mouse colorectal cancer cells (Shanghai Linyuan Biotechnology Co., Ltd.). On Day 6, the mice were evenly divided into 8 groups. The tumor-bearing mice in each group were intraperitoneally injected with PBS (twice per week, two weeks in total), control antibody human IgG-Fc protein (7.5 mg/kg, twice per week, two weeks in total), CD137 antibody YN-006 antibody (3 mg/kg, twice per week, two weeks in total), PD-L1 antibody YN-035 (7.5 mg/kg, twice per week, two weeks in total), CD137 antibody YN-006 antibody (3 mg/kg, twice per week, two weeks in total)+PD-L1 antibody YN-035 (7.5 mg/kg, twice per week, two weeks in total), anti-PD-L1/CD137 bispecific antibody YN-051 (7.5 mg/kg, twice per week, two weeks in total), anti-PD-L1 antibody Atezolizumab (7.5 mg/kg, twice per week, two weeks in total), and anti-PD-L1 antibody Avelumab (7.5 mg/kg, twice per week, two weeks in total), respectively. Except that the PBS group included 5 mice, each of the remainder 7 groups included 6 mice. The mice in each group were regularly observed for the change of body weight and tumor size. The experimental results are shown in FIG. 23 and Table 12. FIG. 23 shows that YN006, YN035, YN006+YN035, YN051, Atezolizumab, and Avelumab all have a significant antitumor activity as compared with the PBS group or the control antibody human IgG-Fc group. Among them, the anti-tumor activities of YN006+YN035 and YN051 are significantly stronger than YN006, YN035, Atezolizumab, and Avelumab. Table 12 shows that at the end of the animal experiment, 5 mice in the YN051 group had tumors completely regressed, while only 1 mouse in the YN006+YN035 group had tumors completely regressed, indicating that the therapeutic effect of YN051 was better than that of YN006+YN035.

TABLE 12

| Number of Mice in Which the Tumors are Completely Eliminated of Each Group | |
|---|---|
| Antibody | Number of mice in which the tumors are completed eliminated/ total number of experiment animals in each group |
| PBS | 0/5 |
| Human IgG1 Fc | 0/6 |
| Atezolizumab | 0/6 |
| Avelumab | 0/6 |
| YN-006 | 0/6 |
| YN-035 | 1/6 |

TABLE 12-continued

| Number of Mice in Which the Tumors are Completely Eliminated of Each Group | |
|---|---|
| Antibody | Number of mice in which the tumors are completed eliminated/ total number of experiment animals in each group |
| YN-006 + YN-035 | 1/6 |
| YN-051 | 5/6 |

The foregoing detailed description is provided by way of explanation and examples, and is not intended to limit the scope of the appended claims. At present, a variety of changes in the embodiments listed herein are obvious to humans of ordinary skills in the art and are within the scope of the appended claims and the equivalent solutions.

The invention claimed is:

1. An antibody or an antigen binding fragment thereof, which is capable of binding to CD137 protein, comprising a light chain variable region VL which comprises LCDR1-3 and a heavy chain variable region VH which comprises HCDR1-3, the amino acid sequences of said LCDR1-3 are sequentially set forth in SEQ ID NO: 80-82, and the amino acid sequences of said HCDR1-3 are sequentially set forth in SEQ ID NO: 77-79.

2. The antibody or the antigen binding fragment thereof according to claim 1, wherein said light chain variable region VL comprises the amino acid sequence as set forth in SEQ ID NO: 20, and said heavy chain variable region VH comprises the amino acid sequence as set forth in SEQ ID NO: 18 or SEQ ID NO: 25.

3. The antibody or the antigen binding fragment thereof according to claim 1, which has a CD137 agonistic activity.

4. The antibody or the antigen binding fragment thereof according to claim 1, wherein said antibody is selected from the group consisting of monoclonal antibody, single-strand antibody, chimeric antibody, humanized antibody and fully human antibody; wherein said antigen-binding fragment is selected from the group consisting of Fab, Fab', F(ab)2 and Fv fragment.

5. The antibody or the antigen binding fragment thereof according to claim 1, which comprises a light chain constant region, wherein the light chain constant region comprises a human Igλ constant region.

6. The antibody or the antigen binding fragment thereof according to claim 1, which comprises a heavy chain constant region, wherein the heavy chain constant region comprises a human IgG constant region.

7. The antibody or the antigen binding fragment thereof according to claim 1, which comprises a light chain and a heavy chain, wherein said light chain comprises the amino acid sequence as set forth in SEQ ID NO: 23, and said heavy chain or its fragment comprises the amino acid sequence as set forth in SEQ ID NO: 21 or SEQ ID NO: 27.

8. One or more isolated nucleic acid molecules which encode the antibody or the antigen binding fragment thereof according to claim 1.

9. A vector which comprises the one or more nucleic acid molecules according to claim 8.

10. A cell which comprises the one or more nucleic acid molecules according to claim 8.

11. A pharmaceutical composition, comprising the antibody or the antigen binding fragment thereof according to claim 1, and a pharmaceutically acceptable adjuvant.

12. A method for treating a tumor, wherein said the tumor is colon cancer, and the method comprising: administering an effective amount of the antibody or the antigen binding fragment thereof according to claim 1 to a subject in need thereof.

* * * * *